US012303562B2

(12) United States Patent
Pinter et al.

(10) Patent No.: US 12,303,562 B2
(45) Date of Patent: May 20, 2025

(54) **ANTI-LAM AND ANTI-PIM6/LAM MONOCLONAL ANTIBODIES FOR DIAGNOSIS AND TREATMENT OF *MYCOBACTERIUM TUBERCULOSIS* INFECTIONS**

(71) Applicant: Rutgers, The State University of New Jersey, New Brunswick, NJ (US)

(72) Inventors: Abraham Pinter, Lakewood, NJ (US); Alok K. Choudhary, Plainsboro, NJ (US); Deendayal Patel, Bloomfield, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 18/335,489

(22) Filed: Jun. 15, 2023

(65) Prior Publication Data

US 2024/0307535 A1 Sep. 19, 2024

Related U.S. Application Data

(60) Continuation of application No. 17/651,523, filed on Feb. 17, 2022, now Pat. No. 11,707,525, which is a continuation of application No. 16/910,621, filed on Jun. 24, 2020, now Pat. No. 11,273,220, which is a division of application No. 16/076,971, filed as application No. PCT/US2017/016058 on Feb. 1, 2017, now Pat. No. 10,729,771.

(60) Provisional application No. 62/293,406, filed on Feb. 10, 2016.

(51) Int. Cl.

| | |
|---|---|
| *A61K 39/40* | (2006.01) |
| *A61K 39/04* | (2006.01) |
| *A61P 31/06* | (2006.01) |
| *C07K 16/12* | (2006.01) |
| *G01N 33/569* | (2006.01) |

(52) U.S. Cl.
CPC .............. *A61K 39/40* (2013.01); *A61K 39/04* (2013.01); *A61P 31/06* (2018.01); *C07K 16/1289* (2013.01); *G01N 33/56933* (2013.01); *G01N 33/5695* (2013.01); *C07K 2317/21* (2013.01); *C07K 2317/622* (2013.01); *C07K 2317/92* (2013.01); *G01N 2333/35* (2013.01); *G01N 2400/02* (2013.01); *G01N 2800/44* (2013.01)

(58) Field of Classification Search
None
See application file for complete search history.

(56) References Cited

U.S. PATENT DOCUMENTS

| | | | |
|---|---|---|---|
| 10,729,771 | B2 | 8/2020 | Pinter et al. |
| 11,273,220 | B2 | 3/2022 | Pinter et al. |
| 2001/0007660 | A1 | 7/2001 | Glatman-Freedman et al. |
| 2011/0002937 | A1 | 1/2011 | Dessain et al. |
| 2012/0122225 | A1 | 5/2012 | Kobayashi et al. |
| 2013/0309237 | A1 | 11/2013 | Macary et al. |
| 2015/0110801 | A1 | 4/2015 | Croll et al. |
| 2016/0083458 | A1 | 3/2016 | Katsuragi et al. |

FOREIGN PATENT DOCUMENTS

| | | | |
|---|---|---|---|
| EA | 200700345 | A1 | 8/2007 |
| EP | 2821415 | A1 | 1/2015 |
| JP | 2008507544 | A | 3/2008 |
| WO | 2010/032059 | A2 | 3/2010 |
| WO | 2012102679 | A1 | 8/2012 |
| WO | 2013129634 | A1 | 9/2013 |

OTHER PUBLICATIONS

Bendig: "Humanization of Rodent Monoclonal Antibodies by CDR Grafting", Methods: A Companion to Methods in Enzymology, 1995, No. 8, pp. 83-93.
Beyene, et al: "Serodiagnosis of Tuberculous Lymphadenitis Using a Combination of Antigens", J. Infect Dev Ctries 2010; 4(2):096-102.
Casset, et al: "A Peptide Mimetic of an Anti-CD4 Monoclonal Antibody by Rational Design", 2003, BBRC, No. 307, pp. 198-205.
Chan et al., "The Diagnositc Targeting of a Carbohydrate Virulence Factor from M. Tuberculosis," Scientific Reports (May 15, 2015); 5(1):1-12.
Chen, et al: "Enhancement and Destruction of Antibody Function by Somatic Mutation: Unequal Occurrence is Controlled by V Gene Combinatorial Associations", 1995, The EMBO Journal, vol. 14, No. 12, pp. 2784-2794.
Chen, et al: "Selection and Analysis of an Optimized Anti-VEGF Antibody: Crystal Structure of an Affinity-Matured Fab in Complex with Antigen", 1999, J. Mol. Bio., No. 293, pp. 865-881.
Choudhary et al., "Characterization of the Antigenic Heterogeneity of Lipoarabinomannan, the Major Surface Glycolipid of *Mycobacterium tuberculosis*, and Complexity of Antibody Specificities toward This Antigen," The Journal of Immunology (2018); 200:3053-3066.
Kussie, et al: "A Single Engineered Amino Acid Substitution Changes Antibody Fine Specificity", 1994, Journal of Immunology, vol. 152, pp. 146-152.

(Continued)

*Primary Examiner* — Jennifer E Graser

(74) *Attorney, Agent, or Firm* — FOX ROTHSCHILD LLP

(57) ABSTRACT

The present invention broadly provides different compositions, kits, vectors, and methods including monoclonal antibodies directed to epitopes found within lipoarabinomannan (LAM) and phosphatidyl-myo-inositol mannoside 6 (PIM6) for the diagnosis and treatment of *Mycobacterium tuberculosis* infections.

11 Claims, 47 Drawing Sheets

Specification includes a Sequence Listing.

(56) References Cited

OTHER PUBLICATIONS

MacCallum et al: "Antibody-Antigen Interactions: Contact Analysis and Binding Site Topography", J. Mol. Biol. 1996, vol. 262, pp. 732-745.
Mikayama et al: "Molecular Cloning and Functional Expression of a cDNA Encoding Glycosylation-Inhibiting Factor", Nov. 1993, Proc. Natl. Acad. Sci, vol. 90, pp. 10056-10060.
Pascalis, et al: "Grating of "Abbreviated" Complementarity-Determining Regions Containing Specificity-Determining Residues Essential for Ligand Contact to Engineer a Less Immunogenic Humanized Monoclonal Antibody", 2002, The Journal of Immunology, No. 169, pp. 3076-3084.
Paul: Fundamental Immunology, 3rd Edition, 1993, Reven Press, pp. 292-295, under the heading "Fv Structure and Diversity in Three Dimensions".
Rademacher et al., "Ligand Specificity of CS-35, a Monoclonal Antibody That Recognizes Mycobacterial Lipoarabinomannan: A Model System for Oligofuranoside—Protein Recognition," J. Am. Chem. Soc. (2007); 129:10489-10502.
Rudikoff, et al: "Single Amino Acid Substitution Altering Antigen-Binding Specificity", Proc. Natl. Acad. Sci., Mar. 1982, vol. 79, pp. 1979-1983.
Torrelles, et al: "Truncated Structural Variants of Lipoarabinomannan in *Mycobacterium leprae* and an Ethambutol-Resistant Strain of *Mycobacterium tuberculosis*", Sep. 24, 2004, The Journal of Biological Chemistry, vol. 279, No. 39, pp. 41227-41239.
Vajdos, et al: "Comprehensive Functional Maps of the Antigen-Binding Site of an Anti-ErbB2 Antibody Obtained with Shotgun Scanning Mutagenesis", 2002, J. Mol. Biol., No. 320, pp. 415-428.
Wu, et al: "Humanization of a Murine Monoclonal Antibody by Simultaneous Optimization of Framework and CDR Residues", 1999, J. Mol. Biol., No. 294, pp. 151-162.
Brown, et al: "Tolerance to single, but not multiple, amino acid replacements in antibody V-H CDR2: A means of minimizing B cell wastage from somatic hypermutation?" J Immunol. May 1, 1996;156(9), pp. 3285-3291.
Tamura, et al: "Structural correlates of an anticarcinoma antibody: identification of specificity-determining residues (SDRs) and development of a minimally immunogenic antibody variant by retention of SDRs only", The Journal of Immunology, Feb. 1, 2000, vol. 164, Issue 3, pp. 1432-1441.
Winkler, et al: Changing the antigen binding specificity by single point mutations of an anti-p24 (HIV-1) antibody, The Journal of Immunology, Oct. 15, 2000, vol. 165, Issue 8, pp. 4505-4514.

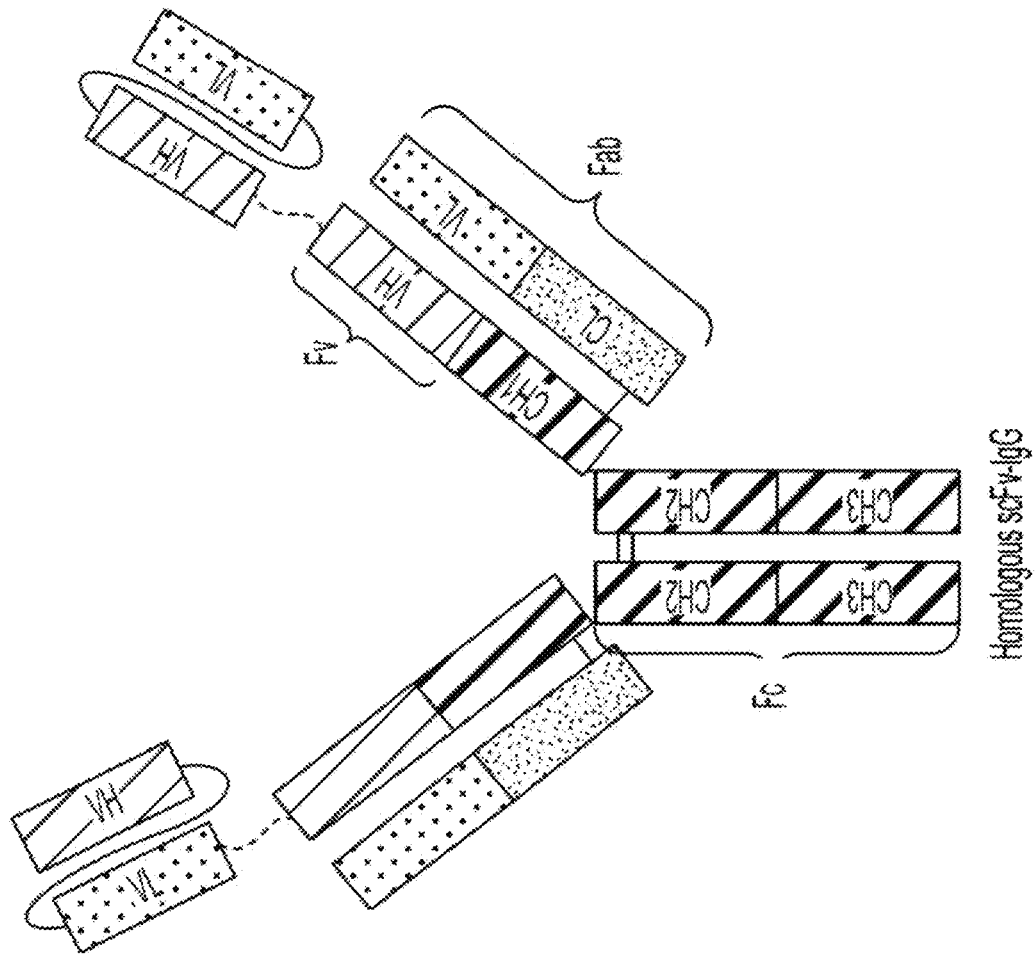

Binding of P30B9-IgM variants vs H37Rv LAM

(Legend: P30B9-IgM (wt); P30B9-IgM-9 pms; P30B9-IgG; Control IgM; P30B9-IgMΔ6aa; Blank)

X-axis: µg/ml mAb; Y-axis: OD 405 (35 min)

FIG. 2A

Binding to H37RV LAM (100 ng/well)

(Legend: P30B9 IgG; P30B9 IgM; P30B9 IgM Δ 6 aa)

X-axis: Antibody Concentration (µg/ml); Y-axis: OD 405 @ 45 min

FIG. 2B

Binding to smeg LAM (100 ng/well)

(Legend: P30B9 IgG; P30B9 IgM; P30B9 IgM Δ 6aa)

X-axis: Antibody Concentration (µg/ml); Y-axis: OD 405 @ 45 min

FIG. 2C

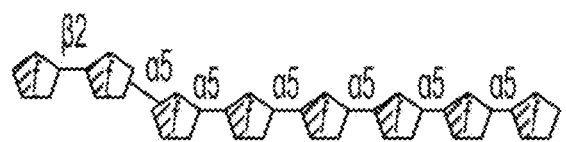
1. YB-8-099
15. YB-BSA-03
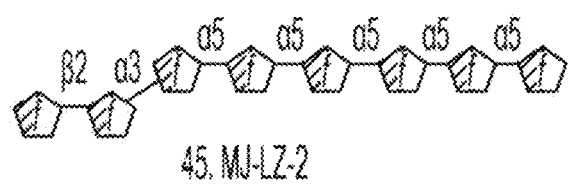
45. MJ-LZ-2
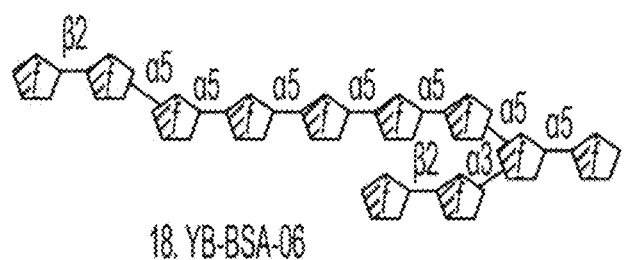
18. YB-BSA-06
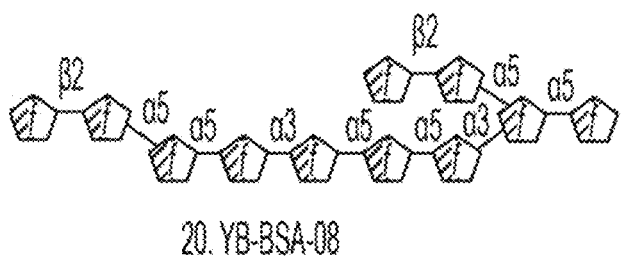
20. YB-BSA-08
FIG. 4A-1

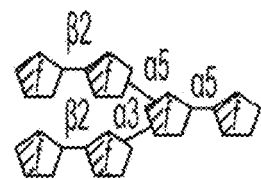
44. MJ-LZ-1
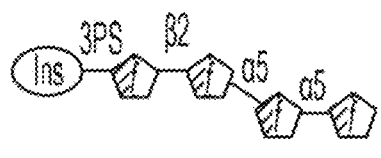
49. YB-BSA-17
MTX  Manp  Araf
5-SCH3
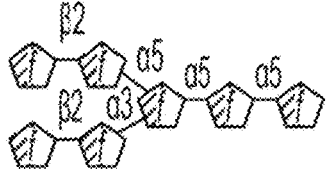
16. YB-BSA-04
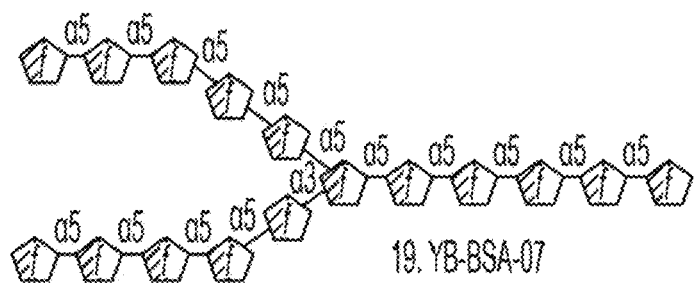
19. YB-BSA-07
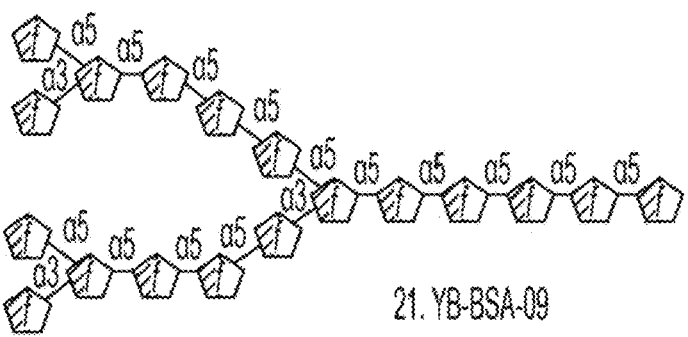
21. YB-BSA-09
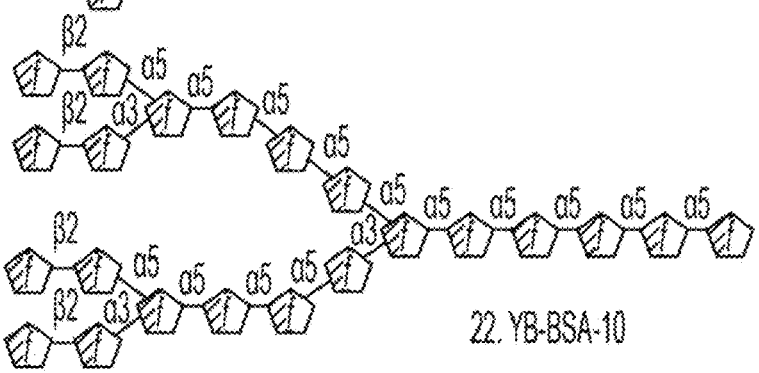
22. YB-BSA-10
FIG. 4A-2

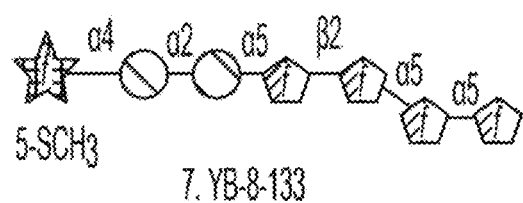
7. YB-8-133
9. YB-8-143
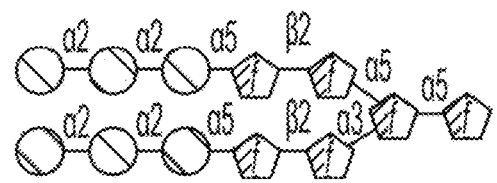
25. YB-BSA-13
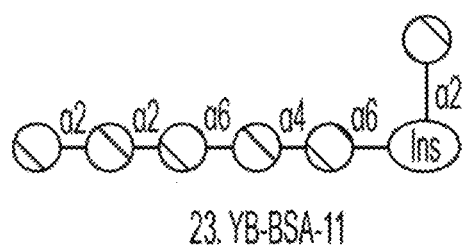
23. YB-BSA-11
FIG. 4A-4

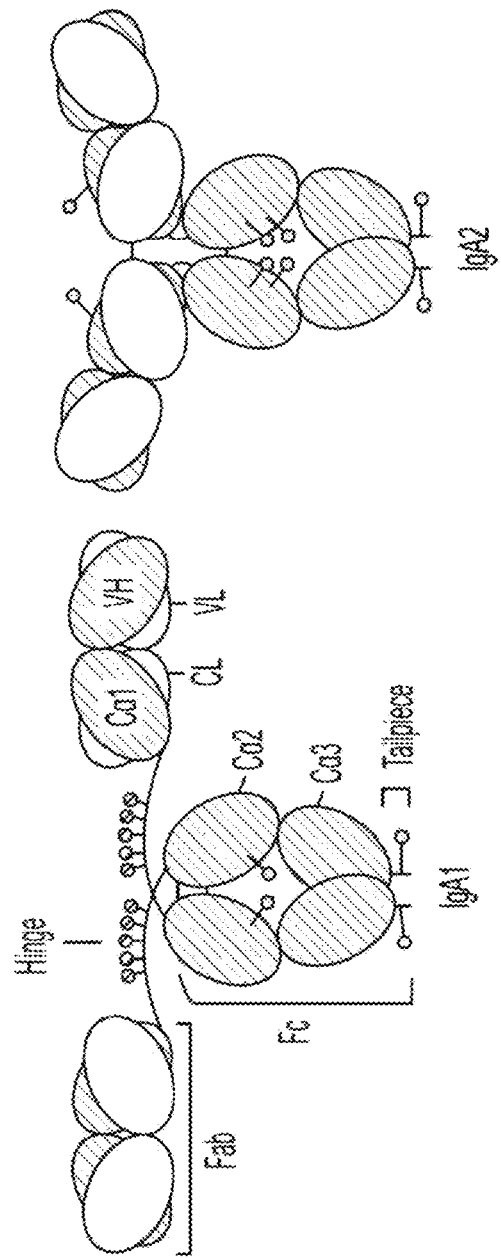
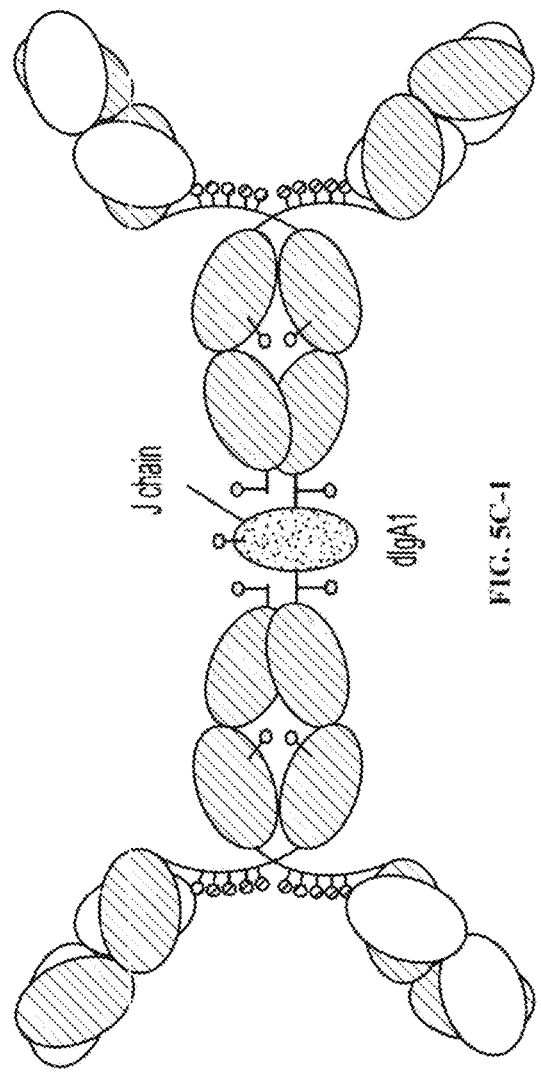
FIG. 5A
FIG. 5B
FIG. 5C-1

FIG. 8- Binding curves of P30B9 to various mannose-capped Ara4 structures, or to tetra- and penta-mannose structures. Preferential binding was seen for structures 3 and 59, which contained the Man-2-a6-Man linkage.

FIG. 8- Binding curves of P30B9 to various mannose-capped Ara4 structures, or to tetra- and penta-mannose structures. Preferential binding was seen for structures 2 and 59, which contained the Man- 2- a6-Man linkage.

FIG. 8- Binding curves of P30B9 to various mannose-capped Ara4 structures, or to tetra- and penta-mannose structures. Preferential binding was seen for structures 2 and 59, which contained the Man- 2- a6-Man linkage.

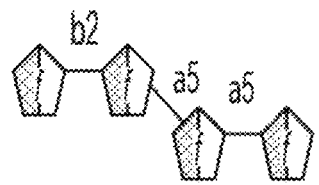
1. YB-8-099
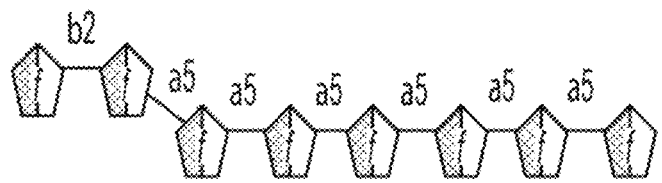
15. YB-BSA-03
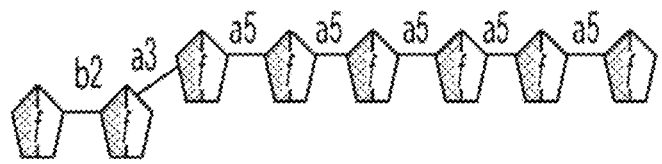
45. MJ-LZ-2
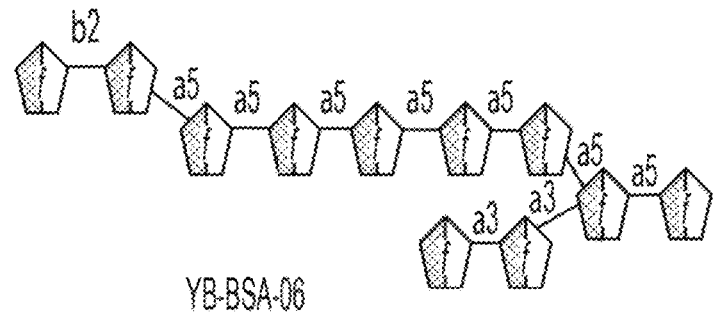
YB-BSA-06
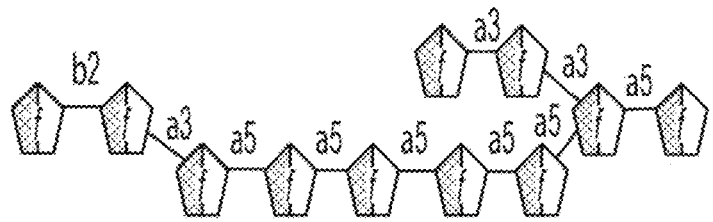
20. YB-BSA-08
FIG. 18C-1

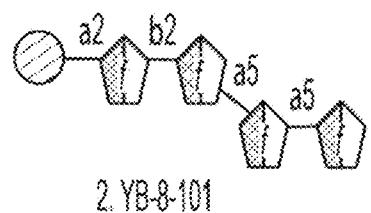
2. YB-8-101
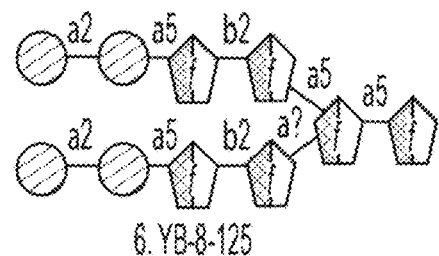
6. YB-8-125
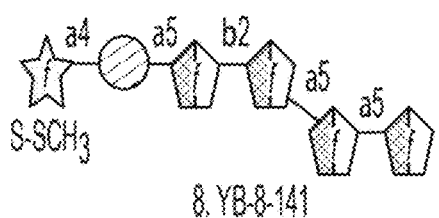
8. YB-8-141
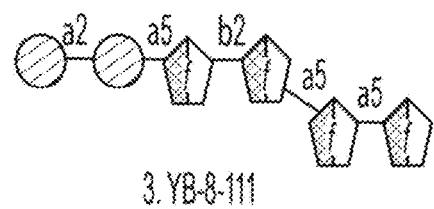
3. YB-8-111
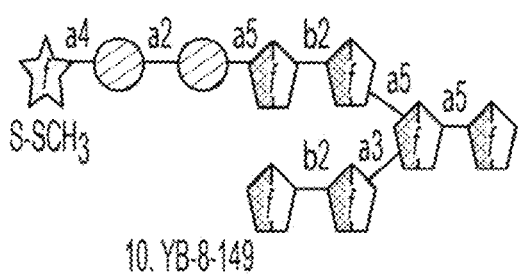
10. YB-8-149
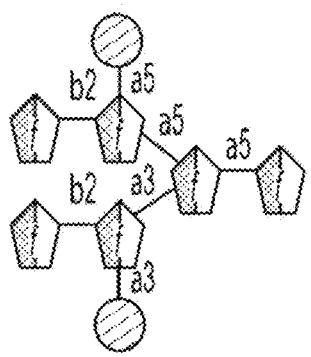
12. YB-11-151
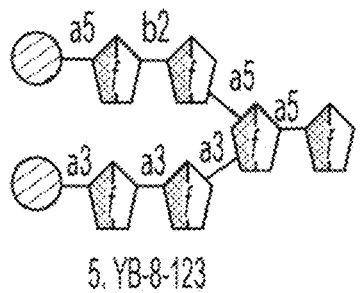
5. YB-8-123
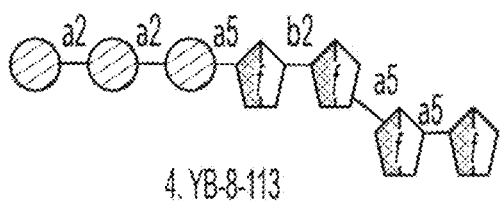
4. YB-8-113
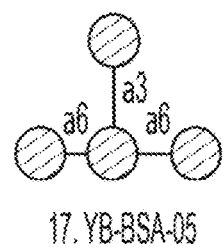
17. YB-BSA-05
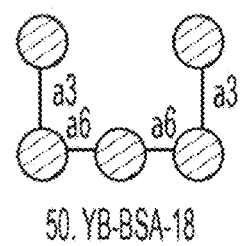
50. YB-BSA-18
FIG. 18C-3

 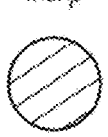 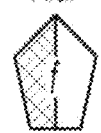
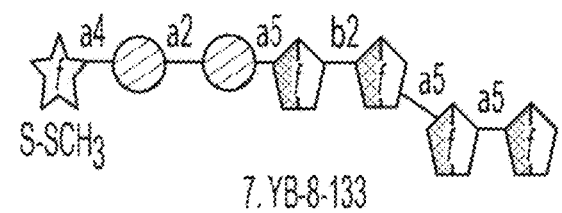
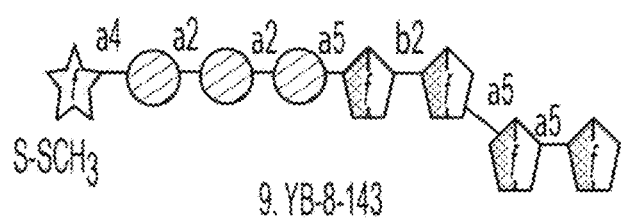
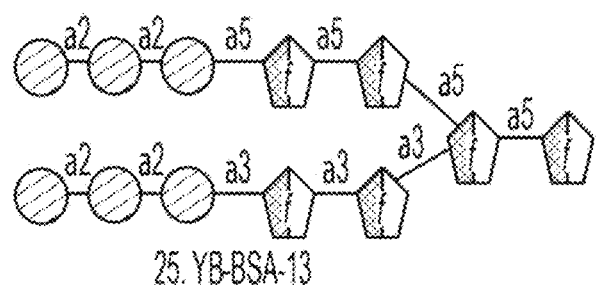
FIG. 18C-4

17

17. YB-BSA-05 (FA-tetra Mann)

50. YB-BSA-18

50. YB-BSA-18 (XL-15-99-PentaMann)

FIG. 23

ANTI-LAM AND ANTI-PIM6/LAM MONOCLONAL ANTIBODIES FOR DIAGNOSIS AND TREATMENT OF *MYCOBACTERIUM TUBERCULOSIS* INFECTIONS

CROSS-REFERENCE TO RELATED APPLICATIONS

This application is a continuation application of U.S. patent application Ser. No. 17/651,523, filed Feb. 17, 2022, now U.S. Pat. No. 11,707,525, which is a continuation of U.S. patent application Ser. No. 16/910,621, filed Jun. 24, 2020, now U.S. Pat. No. 11,273,220, which is a divisional application of U.S. patent application Ser. No. 16/076,971, filed Aug. 9, 2018, now U.S. Pat. No. 10,729,771, which is a 35 U.S.C. 371 National Stage of PCT/US17/16058, filed Feb. 1, 2017, which claims priority to U.S. Provisional Application No. 62/293,406 filed Feb. 10, 2016, all of which are incorporated herein by reference in their entireties.

FIELD OF THE INVENTION

Compositions, kits, vectors, and methods including antibodies directed to epitopes found within lipoarabinomannan (LAM) lipomannan (LM) and phosphatidyl-myo-inositol mannoside 6 (PIM6) for the diagnosis, prevention and treatment of *Mycobacterium tuberculosis* infections are described herein.

SEQUENCE LISTING

The instant application contains a Sequence Listing which has been submitted in XML format and is hereby incorporated by reference in its entirety. Said XML copy, created on Jun. 14, 2023, is named SeqList-096747-00481.xml and is 44.4 kilobytes in size.

BACKGROUND

A. *Mycobacterium Tuberculosis*

Tuberculosis (TB) remains one of the world's deadliest communicable diseases, currently infecting approximately ⅓ of the world's population. According to the WHO Global Tuberculosis Report, 2014: Tuberculosis, in 2013, an estimated 9.0 million people developed TB, and 1.5 million died from the disease. Although there currently are effective drugs available for TB, these require lengthy treatments with multiple antibiotics, and are increasingly compromised by the development of multi-drug resistant (MDR-TB) strains, which currently are responsible for about 3.5% of recent infections. These strains are much harder to treat and have significantly poorer cure rates. Also spreading are extensively drug-resistant TB (XDR-TB) strains, which are even more expensive and difficult to treat than MDR-TB strains, and have now been reported in 100 countries around the world. Consequently, new approaches are needed for the earlier diagnosis and treatment of TB infections.

B. Lipoarabinomannan (LAM)

The glycolipid lipoarabinomannan (LAM) is a major structural and antigenic component of the cell wall of members of the *Mycobacterium tuberculosis*-complex, and it mediates a number of important functions that promote productive infection and disease development. LAM is also an important immunodiagnostic target for detecting active infection with TB, especially in patients co-infected with HIV-1, and a potential vaccine target. Despite the importance of LAM as an immunodiagnostic target and its significant role in the physiology of M. tb infection and pathogenicity, surprisingly little is known about the nature of the human humoral response towards this antigen. Previously available LAM-specific monoclonal antibodies have been derived from mice immunized with LAM purified from either *Mycobacterium leprae* or *Mycobacterium tuberculosis*, and there have been no descriptions of any human monoclonal antibodies against LAM that have been induced in response either to immunization or to infection by *Mycobacterium tuberculosis*.

Lipomannan (LM)—is the immediate precursor to LAM and contain a phosphatidyl-myo-inositol domain modified by a mannan domain comprised of an α(1→6)-linked Manp backbone substituted with short α(1→2)-mannopyranosyl side chains, but with no arabinose side chains.

C. Phosphatidyl-Myo-Inositol Mannoside 6 (PIM6)

PIM6 is a product of PIM2, a common precursor to LM and LAM. The core of these molecules is a myo-inositol structure glycosylated with a Manp unit at positions 2 and 6. In PIM6, the Manp unit at positions 6 is further substituted by two terminal α-Manp(1→2)-linked sugars identical to the mannose cap on ManLAM. These molecules are acylated by as many as 4 fatty acid chains, attached to the inositol head group and to the core Man residue, which non-covalently anchor these molecules to the inner and outer membranes of the cell envelope. PIM6 was reported to bind to C-type lectins and DC-SIGN, the major receptor on dendritic cells, and to be a strong TLR2 agonist and enhancer of HIV-1 replication that possesses potent anti-inflammatory activities.

SUMMARY OF THE INVENTION

Described herein are novel anti-LAM and anti-PIM6/LAM monoclonal antibodies (mAbs) for diagnosis and treatment of *Mycobacterium tuberculosis* infections. The isolation and characterization of these novel human antibodies specific for glycolipids of *Mycobacterium tuberculosis*, including human mAbs specific for LAM epitopes, and a human mAb specific for an epitope shared by LAM and PIM6, are described below.

Accordingly, described herein is a human monoclonal anti-lipoarabinomannan (anti-LAM) antibody, or an antigen-binding portion thereof, that specifically binds to a LAM epitope including an Ara4 structure, an Ara6 structure, or a combination thereof, wherein the anti-LAM antibody includes a CDR1 variable light region having at least 80% identity with SEQ ID NO: 1 or antigenic fragments thereof, a CDR2 variable light region having at least 80% identity with the sequence GAS or antigenic fragments thereof, a CDR3 variable light region having at least 80% identity with SEQ ID NO: 3 or SEQ ID NO: 26 or antigenic fragments thereof, a CDR1 variable heavy region having at least 80% identity with SEQ ID NO: 4 or antigenic fragments thereof, a CDR2 variable heavy region having at least 80% identity with SEQ ID NO: 5 or antigenic fragments thereof, and a CDR3 variable heavy region having at least 80% identity with SEQ ID NO: 6 or SEQ ID NO: 23 or antigenic fragments thereof. The human monoclonal anti-LAM antibody or antigen-binding portion thereof can include a heavy chain variable region including the amino acid sequences of SEQ ID NO:21 and SEQ ID NO:23, and a light chain variable region including the amino acid sequences of SEQ ID NO: 24 and SEQ ID NO:26. The anti-LAM antibody can be an scFv-IgG, and IgGa or an IgM antibody. An example of an ant-LAM antibody is A194.

Also described herein is a human monoclonal anti-LAM antibody or an antigen-binding portion thereof, that specifically binds to a LAM epitope including at least one of: a mannose-capped Ara4 structure and a mannose-capped Ara6 structure. The anti-LAM antibody can include a CDR1 variable light region having at least 80% identity with SEQ ID NO: 7 or antigenic fragments thereof, a CDR2 variable light region having at least 80% identity with SEQ ID NO: 8 or antigenic fragments thereof, a CDR3 variable light region having at least 80% identity with SEQ ID NO: 9 or SEQ ID NO: 32 or antigenic fragments thereof, a CDR1 variable heavy region having at least 80% identity with SEQ ID NO: 10 or antigenic fragments thereof, a CDR2 variable heavy region having at least 80% identity with SEQ ID NO: 11 or antigenic fragments thereof, and a CDR3 variable heavy region having at least 80% identity with SEQ ID NO: 12 or SEQ ID NO: 29 or antigenic fragments thereof. The antibody can include a heavy chain variable region including the amino acid sequence of SEQ ID NO:43 and a light chain variable region including the amino acid sequence of SEQ ID NO:44. The anti-LAM antibody can be, for example, an IgM or IgA antibody. An example of an anti-LAM antibody is P3B09.

Further described herein is a human monoclonal anti-LAM antibody, or an antigen-binding portion thereof, that specifically binds to a LAM epitope including an α-Manp (1→2) linked structure attached at a nonreducing end of Ara4 or Ara6, wherein the anti-LAM antibody includes a CDR1 variable light region having at least 80% identity with SEQ ID NO: 7 or antigenic fragments thereof, a CDR2 variable light region having at least 80% identity with SEQ ID NO: 8 or antigenic fragments thereof, a CDR3 variable light region having at least 80% identity with SEQ ID NO: 9 or antigenic fragments thereof, a CDR1 variable heavy region having at least 80% identity with SEQ ID NO: 10 or antigenic fragments thereof, a CDR2 variable heavy region having at least 80% identity with SEQ ID NO: 11 or antigenic fragments thereof, and a CDR3 variable heavy region having at least 80% identity with SEQ ID NO: 12 or antigenic fragments thereof. The anti-LAM antibody (e.g., P3B09) can be, for example, an IgM or IgA antibody.

Yet further described herein is a human monoclonal anti-PIM6/LAM antibody, or an antigen-binding portion thereof, that specifically binds to an epitope present in LAM and PIM6, the epitope including at least one polymannose structure. The epitope is in the PIM6 mannan domain, and is also present in mycobacterial lipomannan (LM). The anti-PIM6/LAM antibody can include a CDR1 variable light region having at least 80% identity with SEQ ID NO: 13 or antigenic fragments thereof, a CDR2 variable light region having at least 80% identity with the sequence WAS or antigenic fragments thereof, a CDR3 variable light region having at least 80% identity with SEQ ID NO: 15 or antigenic fragments thereof, a CDR1 variable heavy region having at least 80% identity with SEQ ID NO: 16 or antigenic fragments thereof, a CDR2 variable heavy region having at least 80% identity with SEQ ID NO: 17 or antigenic fragments thereof, and a CDR3 variable heavy region having at least 80% identity with SEQ ID NO: 18 or antigenic fragments thereof. The antibody can, for example, include a heavy chain variable region including the amino acid sequence of SEQ ID NO:47 and a light chain variable region including the amino acid sequence of SEQ ID NO:48. The anti-PIM6/LAM antibody can be, for example, an IgM, IgA or IgG antibody. An example of an anti-PIM6/LAM antibody is P95C1.

Also described herein is a kit for detecting at least one LAM epitope. The kit includes (a) at least a first anti-LAM antibody that binds specifically to a LAM epitope; (b) a support to which the at least first anti-LAM antibody is bound; (c) a detection antibody that binds specifically to LAM, or specifically to the at least first anti-LAM antibody, wherein the detection antibody is labeled with a reporter molecule; and (d) a buffer. The at least first anti-LAM antibody is, for example, a human monoclonal anti-LAM antibody as described herein. The detection antibody can be, for example, a second anti-LAM antibody that binds specifically to LAM. In some embodiments, the at least one of the first anti-LAM antibody and the second anti-LAM antibody is an scFv-IgG or IgM antibody and includes a CDR1 variable light region having at least 80% identity with SEQ ID NO: 1 or antigenic fragments thereof, a CDR2 variable light region having at least 80% identity with the sequence GAS or antigenic fragments thereof, a CDR3 variable light region having at least 80% identity with SEQ ID NO: 3 or SEQ ID NO: 26 or antigenic fragments thereof, a CDR1 variable heavy region having at least 80% identity with SEQ ID NO: 4 or antigenic fragments thereof, a CDR2 variable heavy region having at least 80% identity with SEQ ID NO: 5 or antigenic fragments thereof, and a CDR3 variable heavy region having at least 80% identity with SEQ ID NO: 6 or SEQ ID NO:23 or antigenic fragments thereof. In some embodiments of the kit, at least one of the first anti-LAM antibody and the second anti-LAM antibody includes a heavy chain variable region including the amino acid sequences of SEQ ID NO:21 and SEQ ID NO:23, and a light chain variable region including the amino acid sequences of SEQ ID NO: 24 and SEQ ID NO:26.

Still further described herein is a method of diagnosing an active tuberculosis infection in an individual including: (a) obtaining a sample from an individual that includes or is suspected of including LAM; (b) treating said sample to expose individual LAM epitopes; (c) contacting said sample with at least a first antibody that binds specifically to a first epitope on said LAM; (d) contacting said sample with a detection antibody that binds specifically to LAM, or specifically to the at least first antibody; (e) detecting binding of the at least first antibody to said first epitope on LAM; and (f) diagnosing said patient as having an active tuberculosis infection, the binding of the at least first antibody to said first epitope on LAM indicating an active tuberculosis infection. The at least first antibody is, for example, a human monoclonal anti-LAM antibody or human monoclonal anti-PIM6/LAM antibody as described herein. The detection antibody can be, for example, an anti-LAM antibody that binds specifically to LAM. In some embodiments of the method, the at least first antibody and the detection antibody each include a CDR1 variable light region having at least 80% identity with SEQ ID NO: 1 or antigenic fragments thereof, a CDR2 variable light region having at least 80% identity with the sequence GAS or antigenic fragments thereof, a CDR3 variable light region having at least 80% identity with SEQ ID NO: 3 or SEQ ID NO: 26 or antigenic fragments thereof, a CDR1 variable heavy region having at least 80% identity with SEQ ID NO: 4 or antigenic fragments thereof, a CDR2 variable heavy region having at least 80% identity with SEQ ID NO: 5 or antigenic fragments thereof, and a CDR3 variable heavy region having at least 80% identity with SEQ ID NO: 6 or SEQ ID NO: 23 or antigenic fragments thereof. In some embodiments of the method, at least one of the first antibody and the detection antibody is an scFv-IgG or IgM antibody and includes a CDR1 region having a variable light region having at least 80% identity with SEQ ID NO: 1 or antigenic fragments thereof, a CDR2 variable light region having at least 80% identity with the sequence GAS or antigenic fragments thereof, a CDR3 variable light region having at least 80% identity with SEQ ID NO: 3 or SEQ ID NO: 26 or antigenic fragments thereof, a CDR1 variable heavy region having at least 80% identity with SEQ ID NO: 4 or antigenic fragments thereof, a CDR2 variable heavy region having at least 80% identity with SEQ ID NO: 5 or antigenic fragments thereof, and a CDR3 variable heavy region having at least 80% identity with SEQ ID NO: 6 or SEQ ID NO: 23 or antigenic fragments thereof. In some embodiments, the individual is a human.

Also described herein is a method of treating a tuberculosis infection in an individual (e.g., a human). The method includes administering to said individual a therapeutically effective amount of at least one human monoclonal anti-LAM antibody or human monoclonal anti-PIM6/LAM antibody as described herein. The method can further include administering to said individual a therapeutically effective amount of at least one antibiotic. The tuberculosis infection can be a multi-drug resistant (MDR-TB) tuberculosis infection.

Further described herein are nucleotide sequences encoding the heavy chains and light chains (including variable regions) of the antibodies described herein.

A. Anti-LAM Antibodies and Anti-PIM6/LAM Antibodies

In some embodiments, the invention provides an anti-LAM antibody, or an antigen binding portion thereof. In some embodiments, the invention provides an anti-PIM6/LAM antibody, or an antigen binding portion thereof. An anti-LAM antibody (or antigen binding portion thereof) as described herein binds specifically to a LAM epitope. An anti-PIM6/LAM antibody (or antigen binding portion thereof) as described herein binds specifically to both a LAM epitope and a PIM6 epitope. In some embodiments, the LAM and PIM6 epitopes are derived from various mycobacterial species. In further embodiments, the various mycobacterial species are virulent members of the *Mycobacterium tuberculosis*-complex. In yet further embodiments, the mycobacterial species is *Mycobacterium tuberculosis*. In some embodiments, the anti-LAM antibody or anti-PIM6/LAM antibody is a monoclonal antibody (mAb). In further embodiments, the anti-LAM antibody or anti-PIM6/LAM antibody is a human monoclonal anti-LAM antibody or human monoclonal anti-PIM6/LAM antibody, respectively. In other embodiments, the anti-LAM antibody or anti-PIM6/LAM antibody is a humanized monoclonal anti-LAM antibody or anti-PIM6/LAM antibody, respectively. In some embodiments, the anti-LAM antibody binds to Ara4 and Ara6 structures.

In some embodiments, the LAM epitope is an uncapped arabinose chain. In some embodiments the LAM epitope is an uncapped or single mannose capped arabinose chain, with or without a terminal MTX substitution.

In some embodiments, the LAM epitope is a mannose-capped Ara4 structure and a mannose-capped Ara6 structure. In other embodiments, the anti-LAM antibody specifically binds to an α(1→2)-linked dimannose structure, which may be joined either to an Ara4/Ara6 structure, or to a polymannose structure (FIG. 8A-8B-1-8B-3). In some embodiments, the PIM6 epitope includes at least one polymannose structure also present in mycobacterial lipomannan (LM). In some embodiments the anti-PIM6/LAM antibody specifically binds to a PIM6 epitope that includes at least one polymannose structure in the PIM6 mannan domain. In some embodiments, the LAM epitope includes at least one methylthioxylose (MTX) or methylsylfinylxylofuranosyl (MSX) substitution. In some embodiments, the LAM epitope includes at least one phosphatidyl-myo-inositol substitution (PILAM). In some embodiments, the LAM epitope is an arabinose chain capped with at least one mannose, i.e. mannosylated Man-LAM epitope. In further embodiments, the capped arabinose chain includes Ara4 and/or Ara6 structures. In some embodiments, the Man-LAM epitope includes mono-mannose substituted arabinose chains, di-mannose substituted arabinose chains, tri-mannose substituted arabinose chains, or combinations thereof. In some embodiments, the Man-LAM epitope includes di-mannose or tri-mannose capped Ara4 and/or Ara6 structures. In some embodiments, the Man-LAM epitope is di-mannose capped Ara6. In some embodiments, the anti-LAM antibody or anti-PIM6/LAM antibody includes an IgG antibody. In further embodiments, the IgG anti-LAM antibody or anti-PIM6/LAM antibody includes a subclass of IgGl, IgG2 or IgG3. In some embodiments, the anti-LAM antibody or anti-PIM6/LAM antibody is not an IgG antibody. In other embodiments, the anti-LAM antibody or anti-PIM6/LAM antibody includes an IgA antibody. In other embodiments, the anti-LAM antibody or anti-PIM6/LAM antibody includes an IgM antibody. In some embodiments, the anti-LAM antibody or anti-PIM6/LAM antibody includes a second isotype that has been switched from the isotype originally isolated. In some embodiments, the anti-LAM antibody or anti-PIM6/LAM antibody includes a recombinant antibody. In some embodiments, the recombinant antibody includes a multivalent IgM antibody. In further embodiments, the recombinant antibody includes a pentavalent IgM antibody. In other embodiments, the recombinant antibody includes an ScFv-IgG antibody, in which a single chain Fv fragment of one antibody is joined to the N-terminus of the heavy chain of that or a different anti-LAM mAb. In further embodiments, the recombinant antibody includes a multivalent ScFv-IgG antibody. In further embodiments, the recombinant antibody includes a homologous tetravalent ScFv-IgG antibody, in which the scFv domains were derived from the variable regions of the IgG present in the construct. In yet further embodiments, the recombinant antibody includes a heterologous tetrameric scFv-IgG antibody in which the scFv regions were derived from a different anti-LAM antibody or anti-PIM6/LAM antibody as the IgG region included. In some embodiments, the scFv domain includes a leader sequence joined to the variable heavy (VH) region of second anti-LAM antibody or anti-PIM6/LAM antibody which is joined to the variable light (VL) domain of said anti-LAM antibody or anti-PIM6/LAM antibody. In other embodiments, the scFv domain includes a leader sequence joined to the variable light chain region of a first anti-LAM antibody or anti-PIM6/LAM antibody which is joined to the variable heavy (VH) region of a second anti-LAM antibody or anti-PIM6/LAM antibody. In some embodiments, the anti-LAM antibody is an isolated anti-LAM antibody that specifically binds to a LAM epitope (e.g., one of Ara4 and Ara6 or combinations thereof, an α(1→2)-linked dimannose structure, which may be joined either to an Ara4/Ara6 structure, or to a polymannose structure). In some embodiments, the anti-LAM antibody does not compete with CS-35 and FIND25. In some embodiments, the anti-PIM6/LAM antibody is an isolated anti-PIM6/LAM antibody that specifically binds to at least one polymannose structure in mycobacterial lipomannan (LM).

In some embodiments, the anti-LAM antibody or anti-PIM6/LAM antibody includes a flexible linker. In some embodiments, the flexible linker joins the corresponding heavy and light chain domains into a single chain molecule.

In some embodiments, the flexible linker connects an immunoglobulin light chain (IgVL) to an immunoglobulin heavy chain (IgVH). In further embodiments, the flexible linker is comprised of the formula (GGSGG)n (SEQ ID NO:19), wherein n is any positive integer between 1 and 200 and any ranges in between, e.g. 1 to 5, 1 to 10, 1 to 15, 1 to 25, 1 to 50, 5 to 10, 5 to 25, 10 to 25, 10 to 50, 1 to 100, 1 to 150, and all intervening ranges.

In some embodiments, the anti-LAM antibody (e.g., P30B9, A194-01) has at least one (e.g., one, two, three) complementarity determining region (CDR) (e.g. CDR1, CDR2, CDR3). In some embodiments, the variable light region of CDR1 consists essentially of SEQ ID NO: 1 or antigenic fragments thereof. In other embodiments, the variable light region of CDR1 region consists essentially of SEQ ID NO: 7 or antigenic fragments thereof. In other embodiments, the variable light region of CDR1 region consists essentially of SEQ ID NO: 13 or antigenic fragments thereof. In some embodiments, the variable heavy region of CDR1 consists essentially of SEQ ID NO: 4 or antigenic fragments thereof. In other embodiments, the variable heavy region of CDR1 region consists essentially of SEQ ID NO: 10 or antigenic fragments thereof. In other embodiments, the variable heavy region of CDR1 region consists essentially of SEQ ID NO: 16 or antigenic fragments thereof.

In some embodiments, the variable light region of CDR2 consists essentially of the sequence GAS or antigenic fragments thereof. In other embodiments, the variable light region of CDR2 consists essentially of SEQ ID NO: 8 or antigenic fragments thereof. In other embodiments, the variable light region of CDR2 consists essentially of with the sequence WAS or antigenic fragments thereof. In some embodiments, the variable heavy region of CDR2 consists essentially of SEQ ID NO: 5 or antigenic fragments thereof. In other embodiments, the variable heavy region of CDR2 region consists essentially of SEQ ID NO: 11 or antigenic fragments thereof. In other embodiments, the variable heavy region of CDR2 region consists essentially of SEQ ID NO: 17 or antigenic fragments thereof.

In some embodiments, the variable light region of CDR3 consists essentially of SEQ ID NO: 3 or antigenic fragments thereof. In other embodiments, the variable light region of CDR3 consists essentially of SEQ ID NO: 9 or antigenic fragments thereof. In other embodiments, the variable light region of CDR3 consists essentially of SEQ ID NO: 15 or antigenic fragments thereof. In some embodiments, the variable heavy region of CDR3 consists essentially of SEQ ID NO: 6 or antigenic fragments thereof. In other embodiments, the variable heavy region of CDR3 region consists essentially of SEQ ID NO: 12 or antigenic fragments thereof. In other embodiments, the variable heavy region of CDR3 region consists essentially of SEQ ID NO: 18 or antigenic fragments thereof.

In some embodiments, the anti-PIM6/LAM antibody (e.g., P95C1) has at least one (e.g., one, two, three) CDR (e.g., CDR1, CDR2, CDR3). In some embodiments, the variable light region of CDR1 consists essentially of SEQ ID NO: 13 or antigenic fragments thereof. In some embodiments, the variable heavy region of CDR1 consists essentially of SEQ ID NO: 16 or antigenic fragments thereof. In some embodiments, the variable light region of CDR2 consists essentially of with the sequence WAS or antigenic fragments thereof. In some embodiments, the variable heavy region of CDR2 consists essentially of SEQ ID NO: 17 or antigenic fragments thereof. In some embodiments, the variable light region of CDR3 consists essentially of SEQ ID NO: 15 or antigenic fragments thereof. In some embodiments, the variable heavy region of CDR3 consists essentially of SEQ ID NO: 18 or antigenic fragments thereof.

B. Diagnostic Kits and Methods

In some embodiments, the present invention provides kits for detecting the presence of LAM and/or PIM6 in biological fluids of a human subject. In some embodiments the components of this assays are assembled in a lateral flow device (see World Health Organization 2015, The use of lateral flow urine lipoarabinomannan assay (LF-LAM) for the diagnosis and screening of active tuberculosis in people living with HIV). In some embodiments, the kits include a first anti-LAM (e.g., A194-01, P30B9) or anti-PIM6/LAM (e.g., P95C1) capture antibody, a second anti-LAM or anti-PIM6/LAM detector (detection) antibody labeled with a reporter molecule, a support for which the first anti-LAM or anti-PIM6/LAM antibody is bound to, and a buffer. In some embodiments, at least one of the first anti-LAM or anti-PIM6/LAM antibody and the second anti-LAM or anti-PIM6/LAM antibody is a human monoclonal anti-LAM antibody that binds specifically to one of Ara4 and Ara6 or combinations thereof, or a human monoclonal anti-PIM6/LAM antibody that binds specifically to the mannan domain of LAM (and lipomannan (LM)). In some embodiments, the first anti-LAM antibody and the second anti-LAM antibody bind to the same LAM epitopes which are present in multiple copies on a single LAM molecule. In other embodiments, the first anti-LAM antibody and the second anti-LAM antibody bind to different epitopes present on a single LAM molecule. The LAM and PIM6 epitopes may be any of the LAM and PIM6 epitopes described herein. In other embodiments, a third detector (detection) antibody is included which binds to a non-competing site of the second antibody. In some embodiments, the first antibody and the second antibody are of the same isotype. In other embodiments, the first antibody and the second antibody are different isotypes. In some embodiments of a capture assay, only either the capture antibody or the detection antibody is an anti-LAM antibody (e.g., A194-01, P30B9) or an anti-PIM6/LAM antibody (e.g., P95C1) as described herein.

The antibodies described herein can be used for additional detection and diagnostic applications. For example, in one diagnostic assay, one or more of the antibodies described herein (e.g., A194-01, P30B9, P95C1) can be used to stain tissues obtained from patients to detect the presence of LAM in lesions suspected of containing TB or TB-infected cells (e.g., granulomas). This can be done, for example, with a single antibody as described herein (e.g., A194-01, P30B9, P95C1) that is conjugated with a label that allows sensitive detection. In such a method or assay, detection by P95C1 of PIM6 or related molecules can be achieved in infected tissues. In another example, P95C1 can be used in a PIM6 competition assay, in which the capture of a labeled form of PIM6 by immobilized P95C1 is competed by soluble PIM6 present in a biological fluid (e.g., blood or urine) of a suspect. In the absence of soluble PIM6, this would result in the capture of a signal, which would be competed by the presence of soluble PIM6 (see World Health Organization, 2015 Policy Guidance—The use of lateral flow urine lipoarabinomannan assay (LF-LAM) for the diagnosis and screening of active tuberculosis in people living with HIV).

In some embodiments, the present invention provides kits for distinguishing between a pathogenic member of the *Mycobacterium tuberculosis*-complex and a nonpathogenic member of the *Mycobacterium tuberculosis*-complex. In some embodiments, the anti-LAM antibody is a human monoclonal anti-LAM antibody that binds specifically to one of Ara4 and Ara6 structure with or without a Man or MTX-Man substitution or combinations thereof, or anti-PIM6/LAM antibody that specifically binds at least one polymannose structure in PIM6 or in the LAM mannan domain. In some embodiments, the anti-LAM antibody specifically binds to a Man-LAM epitope including di-mannose substituted side chains, tri-mannose substituted side chains, or combinations thereon. In further embodiments, the anti-LAM antibody specifically binds to Man-LAM epitopes includes di-mannose or tri-mannose capped Ara4 and/or Ara6 structures. In yet further embodiments, the anti-LAM antibody specifically binds to di-mannose capped Ara6 structures.

In some embodiments, the present invention provides methods for diagnosing an active tuberculosis infection in an individual. In some embodiments the anti-LAM or anti PIM6/LAM antibody can be modified with a sensitive tag and used to identify mycobacterial PIM6 or LAM-related material in a tissue sample, as a diagnostic for TB infection and localization. In some embodiments, the method involves the capture of soluble LAM, and includes the steps of (a) obtaining a sample from an individual that includes LAM; (b) treating the sample to isolate or expose said LAM, (c) capturing said isolated or exposed LAM with a first anti-LAM antibody that binds to a first epitope on said LAM; (d) contacting said isolated or exposed LAM with a second anti-LAM antibody, wherein said second anti-LAM antibody binds to a second epitope on said LAM; (e) detecting the binding of at least one of said first anti-LAM antibody and said second anti-LAM antibody to said LAM; and (f) diagnosing said patient as having an active tuberculosis infection, wherein said presence of binding of at least one of said first anti-LAM antibody and said second anti-LAM antibody to said LAM indicates an active tuberculosis infection. In some embodiments, at least one of the first anti-LAM antibody and the second anti-LAM antibody is a human monoclonal anti-LAM antibody that binds specifically to one of Ara4 and Ara6 or combinations thereof. In some embodiments, at least one of the first and second antibodies is a human monoclonal anti-PIM6/LAM antibody that specifically binds to at least one polymannose structure in the LAM mannan domain. In further embodiments, the first antibody and the second antibody are different isotypes. In some embodiments, at least one of the first antibody and the second antibody are recombinant antibodies. In other embodiments, neither the first antibody nor the second antibody are recombinant antibodies. In yet other embodiments, both the first antibody and the second antibody are recombinant antibodies.

In some embodiments, the present invention provides methods of quantifying the amount of LAM and/or PIM6 present in a sample. In some embodiments, the method includes the steps of (a) obtaining a sample that includes LAM and/or PIM6; (b) contacting said sample with an anti-LAM antibody and/or an anti-PIM6 antibody; (c) detecting the presence of specific binding of the anti-LAM antibody to said LAM and/or the binding of the anti-PIM6/LAM antibody to said LAM or said PIM6; and (d) quantifying the amount of LAM or PIM6 in said sample. In some embodiments, the anti-LAM antibody is a human monoclonal anti-LAM antibody that binds specifically to one of Ara4 and Ara6 or combinations thereof. In some embodiments, the anti-PIM6/LAM antibody is a human monoclonal anti-PIM6/LAM antibody that binds specifically to at least one polymannose structure in the PIM6 mannan domain (e.g., to at least one polymannose structure in mycobacterial lipomannan (LM)). In some embodiments, quantifying said amount of LAM and/or PIM6 is achieved by comparing the signal intensity to that of a serially diluted control sample having a known concentration of LAM and/or PIM6.

In some embodiments the present invention provides methods for diagnosing an individual as being infected with *Mycobacterium tuberculosis*. In some embodiments, the method includes the steps of (a) obtaining a sample that includes LAM or PIM6; (b) contacting said sample with an anti-LAM antibody and/or an anti-PIM6 antibody, wherein the anti-LAM antibody binds specifically to a LAM epitope including Man-LAM having at least one at least one 5-de-oxy-5-methylthiopentofuranosyl (MTX) substitution, and the anti-PIM6/LAM antibody binds specifically to an epitope including at least one polymannose structure in the LAM mannan domain, and (c) detecting the presence of specific binding of the anti-LAM antibody to said Man-LAM and/or the presence of specific binding of the anti-PIM6/LAM antibody to said PIM6. In some embodiments, the anti-LAM antibody is a human monoclonal anti-LAM antibody that binds specifically to one of Ara4 and Ara6 or combinations thereof. In some embodiments, the anti-PIM6/LAM antibody is a human monoclonal anti-PIM6/LAM antibody (e.g., P95C1) that binds specifically to at least one polymannose structure in the PIM6 mannan domain.

In some embodiments the method includes an amplification step that increases the sensitivity of the detection method. Examples involve the generation of additional target sites by the use of Tyramide Signal Amplification kit (Perkin-Elmer) or the amplification of the initial signal by the use of the ELISA Amplification System (Thermo Fisher).

In some embodiments, the present invention provides methods of differentiating between a pathogenic member of the *Mycobacterium tuberculosis*-complex and a nonpathogenic member of the *Mycobacterium tuberculosis*-complex. In some embodiments, the method includes the steps of (a) obtaining a sample that comprises LAM and/or PIM6; (b) contacting said sample with an anti-LAM antibody that binds specifically to a Man-LAM epitope that includes di-mannose substituted side chains, tri-mannose substituted side chains, or combinations thereof, or with an anti-PIM6/LAM antibody that binds specifically to at least one polymannose structure in the PIM6 mannan domain; and (c) detecting the presence of specific binding of the anti-LAM antibody to said Man-LAM, or the presence of the specific binding of the anti-PIM6/LAM antibody to said at least one polymannose structure in the PIM6 mannan domain, wherein the presence of said specific binding indicates the presence of a pathogenic member of the *Mycobacterium tuberculosis*-complex. In some embodiments, the anti-LAM antibody is a human monoclonal anti-LAM antibody that binds specifically to one of Ara4 and Ara6 or combinations thereof. In further embodiments, the Man-LAM epitope includes di-mannose or tri-mannose capped Ara4 and/or Ara6 structures. In yet further embodiments, the Man-LAM epitope is di-mannose capped Ara6. In some embodiments, the anti-PIM6/LAM antibody is a human monoclonal anti-PIM6/LAM antibody that binds specifically to at least one polymannose structure in the PIM6 mannan domain.

C. Therapeutic Compositions, Methods, Vaccines, and Vectors

In some embodiments, the present invention provides methods for treating infection by a virulent member of the *Mycobacterium tuberculosis*-complex in an individual. In some embodiments, the method includes administering a therapeutically effective amount of at least one anti-LAM antibody or anti-PIM6/LAM antibody to an individual exposed to infectious M. tb. In further embodiments, the method includes administration of at least one antibiotic. In some embodiments, the TB infection is active. In other embodiments, the TB infection is latent. In some embodiments, the infection is with a multiple-drug resistant (MDR) strain of tuberculosis. In other embodiments, the infection is with an extensively-drug resistant (XDR) strain of tuberculosis.

In some embodiments, the present invention provides a combination therapy for treating infection by a virulent member of the *Mycobacterium tuberculosis*-complex in an individual. In some embodiments, the method includes administering a therapeutically effective amount of a first anti-LAM antibody that specifically binds to a first LAM epitope including at least one of unsubstituted LAM, mono-mannonsylated Man-LAM, MSX-substituted LAM, and combinations thereof or a first anti-PIM6/LAM antibody that specifically binds to at least one polymannose structure in the PIM6 and LAM mannan domain; and administering a therapeutically effective amount of a second anti-LAM antibody that specifically binds to a second LAM epitope including at least one of di-mannose substituted Man-LAM, tri-mannose substituted Man-LAM, and combinations thereof. In some embodiments, the first antibody and the second antibody are administered simultaneously (e.g., in a single composition, or in two compositions administered at the same time). In other embodiments, the first antibody and the second antibody are administered at different time points. In some embodiments, at least one of the first anti-LAM antibody and the second anti-LAM antibody is a human monoclonal anti-LAM antibody that binds specifically to one of Ara4 and Ara6 or combinations thereof. In some embodiments, the anti-PIM6/LAM antibody is a human monoclonal anti-PIM6 antibody that binds specifically to at least one polymannose structure in PIM6 and/or in the PIM6 crossreactive mannan domain of LAM. In some embodiments, the first anti-LAM antibody and the second anti-LAM antibody, or the anti-PIM6/LAM antibody are of different isotypes. In some embodiments, at least one of the first anti-LAM antibody and the second anti-LAM antibody, and the anti-PIM6/LAM antibody are recombinant antibodies. In other embodiments, neither the first anti-LAM antibody nor the second anti-LAM antibody, nor the anti-PIM6/LAM antibody, are recombinant antibodies. In yet other embodiments, both the first anti-LAM antibody and the second anti-LAM antibody, or the anti-PIM6/LAM antibody, are recombinant antibodies. In further embodiments, the method includes administration of at least one antibiotic. In such embodiments, the at least one antibiotic can be administered (e.g., co-administered) simultaneously with the first and second antibodies, or the at least one antibiotic can be administered at a time point different from the time point of administration of the first and second antibodies. In some embodiments, the infection is active. In other embodiments, the infection is latent. In some embodiments, the infection is a multiple-drug resistant (MDR) tuberculosis infection. In other embodiments, the infection is an extensively-drug resistant (XDR) tuberculosis infection.

In some embodiments, the present invention provides vaccines or pharmaceutical compositions for preventing infection by a virulent member of the *Mycobacterium tuberculosis*-complex. In some embodiments, the invention provides a method of stimulating a host immune response in a patient including administering to said patient a therapeutically effective amount of a LAM antigen and/or a PIM6 antigen. In some embodiments these antigens are conjugated to immunogenic protein carriers, and/or are co-administered with an adjuvant that potently stimulates an immune response to glycolipid antigens. In some embodiments, the vaccine or pharmaceutical composition induces an anti-LAM antibody that specifically binds to a Man-LAM epitope, and/or an anti-PIM6/LAM antibody that specifically binds to at least one polymannose structure in the PIM6 mannan domain. In further embodiments, the Man-LAM epitope present in the vaccine or pharmaceutical compositions includes di-mannose or tri-mannose capped Ara4 and/or Ara6 structures. In yet further embodiments, the Man-LAM epitope is di-mannose capped Ara6. In some embodiments, the Man-LAM epitope has at least one MTX substitution. In some embodiments, the anti-LAM antibody and/or anti-PIM6/LAM antibody is an IgM antibody. In other embodiments, the anti-LAM antibody and/or anti-PIM6/LAM antibody is a recombinant antibody.

In some embodiments, the present invention provides a method of preventing infection by a virulent member of the *Mycobacterium tuberculosis*-complex in an individual by passive administration of a protective antibody. In some embodiments, the anti-LAM antibody is a human monoclonal anti-LAM antibody that binds specifically to one of Ara4 and Ara6 or combinations thereof. In some embodiments, the anti-PIM6/LAM antibody is a human monoclonal anti-PIM6/LAM antibody that binds specifically to at least one polymannose structure in the PIM6 and LAM mannan domain. In some embodiments, the method includes administering to an individual a therapeutically effective amount of an anti-LAM antibody that specifically binds to a Man-LAM epitope, and/or an anti-PIM6 antibody that specifically binds to a PIM6 epitope (e.g., an epitope shared by PIM6 and LAM). In further embodiments, the targeted ManLAM epitope includes di-mannose or tri-mannose capped Ara4 and/or Ara6 structures. In yet further embodiments, the ManLAM epitope is di-mannose capped Ara6. In some embodiments, the ManLAM eptipoe has at least one MTX substitution. In some embodiments, the anti-LAM antibody or anti-PIM6/LAM antibody is an IgM antibody. In other embodiments, the anti-LAM antibody or anti-PIM6/LAM antibody is a recombinant antibody.

In some embodiments, the present invention provides passive administration of a protective antibody via recombinant vectors. In some embodiment, the recombinant vectors include a first nucleic acid encoding for an IgVL of an anti-LAM antibody and a second nucleic acid encoding an IgVH of an anti-LAM antibody, wherein each of the nucleic acids is operably linked to a promoter region. In some embodiments, at least one of the IgVL and IgVH is derived from a human monoclonal anti-LAM antibody that binds specifically to one of Ara4 and Ara6 or combinations thereof. In other embodiment, the recombinant vectors include a first nucleic acid encoding for an IgVL of an anti-PIM6/LAM antibody and a second nucleic acid encoding an IgVH of an anti-PIM6/LAM antibody, wherein each of the nucleic acids is operably linked to a promoter region. In some embodiments, the recombinant vectors include additional transcriptional regulation elements. In some embodiments, at least one of the first nucleic acid sequence and the second nucleic acid sequence are organized in an operon. In some embodiments, at least one of the first nucleic acid sequence and the second nucleic acid sequence are organized in an expression cassette. In some embodiments, the first nucleic acid sequence and the second nucleic acid sequence are organized in a single expression cassette. In some embodiments, the first nucleic acid and the second nucleic acid are located in the same cloning vector. In other embodiments, the first nucleic acid and the second nucleic acid are located in different cloning vectors. In some embodiments, expression of the first nucleic acid and the second nucleic acid may be concomitant. In other embodiments, expression of the first nucleic acid and the second nucleic acid is separably inducible. In some embodiments, expression of the first nucleic acid may be temporally separate from expression of the second nucleic acid. In some embodiments, the recombinant vector is a plasmid. In other embodiments, the recombinant vector is a non-replicated virus. In further embodiments, the recombinant vector is an adeno-associated virus.

In some embodiments, the present invention provides for a method of treating infection by a virulent member of the *Mycobacterium tuberculosis*-complex in an individual. In some embodiments, the method includes administering to an individual a first nucleic acid coding for an IgVH of an anti-LAM antibody, and a second nucleic acid coding for an IgVL of an anti-LAM antibody, wherein each of the nucleic acids is operably linked to a promoter region. In other embodiments, the method includes administering to an individual a first nucleic acid coding for an IgVH of an anti-PIM6/LAM antibody, and a second nucleic acid coding for an IgVL of an anti-PIM6/LAM antibody, wherein each of the nucleic acids is operably linked to a promoter region. In some embodiments, at least one of the IgVL and IgVH is derived from a human monoclonal anti-LAM antibody that binds specifically to one of Ara4 and Ara6 or combinations thereof, or from a human monoclonal anti-PIM6/LAM antibody that binds specifically to at least one polymannose structure in the PIM6 mannan domain. In some embodiments, the first nucleic acid and the second nucleic acid are located in the same cloning vector. In other embodiments, the first nucleic acid and the second nucleic acid are located in different cloning vectors. In some embodiments, the recombinant vector is a plasmid. In other embodiments, the recombinant vector is a non-replicated virus. In further embodiments, the recombinant vector is an adeno-associated virus.

Additional embodiments, features and advantages will be readily apparent to one of skill in the art based on the disclosure provided herein. Other features will become more apparent to persons having ordinary skill in the art to which the package pertains and from the following description and claims. Although antibodies, compositions, kits and methods similar or equivalent to those described herein can be used in the practice or testing of the present invention, suitable antibodies, compositions, kits and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 2A—Binding activity of P30B9 IgG and IgM forms, and IgM in which the 6 amino acid insert in the VH region was deleted, or the 9 somatic mutatic mutations in the VH region were reverted to the nearest germ-line sequence, to ManLAM derived from *Mycobacterium tuberculosis*. The 6 amino acid insert contributed to a greater extent than the 9 somatic acid mutations to reactivity. FIGS. 2B and 2C compare the reactivity of the P30B9 IgM and IgG forms and the mutation with the 6 amino acid deletion in the heavy chain against ManLAM from *Mycobacterium tuberculosis* (FIG. 2B) and PILAM from *Mycobacterium smegmatis* (FIG. 2C). The IgM form, but not the IgG form, reacted specifically with ManLAM derived from *Mycobacterium tuberculosis* (FIG. 2B) but not PILAM (FIG. 2C), and the reactivity of the Δ6 amino acid mutant was highly reduced for ManLAM and negative for PILAM.

FIG. 5A—structure of IgA1. FIG. 5B—structure of IgA2. FIG. 5C-1—dimeric IgA1-J dimeric complex. FIG. 5C-2—SDS-PAGE gel of purified P30B9 IgA1, IgA2 and IgA3 proteins, both before and after reduction with DTT. P30B9 IgA3 was later revealed to be an artifact of PCR with a longer hinge region.

FIGS. 8A and 8B-1-8B-3—Binding curves of P30B9 to various mannose-capped Ara4 structures, or to tetra- and penta-mannose structures. Preferential binding was seen for structures 3 (dimannose-Ara4) and 59, which contained the related α-Manp(1→2)-Manp linkage.

FIG. 9A-9B-1-9B-2—Titration of monoclonal anti-LAM antibodies against various uncapped LAM-related glycoconjugates to determine structural requirements for reactivity. FIG. 9A—Analysis of the importance of the Ara-α(1→5)-Ara linkage at the penultimate position from the non-reducing end of the Ara4 sequence. FIG. 9B-1-9B-2—Analysis of the dependence of the Ara-β(1→2)-Ara linkage at the terminal position of the Ara4 sequence.

Antibodies were biotinylated when tested against antibodies from the same species. Note inability of A194-01 to compete for biotinylated P30B9.

FIG. 12A-12E—Competition of binding of anti-LAM monoclonal antibodies to LAM derived from *Mycobacterium tuberculosis* (ManLAM) and LAM derived from *Mycobacterium smegmatis* (PILAM). Efficient competition between FIND25 and P30B9 for ManLAM is consistent with predominance of dimannose-substituted Ara6, while lack of competition of these two mAbs by A194 is consistent with its poor reactivity with dimannose capped structures. The efficient competition of A194 for FIND25 vs PILAM is consistent with the absence of dimannose capping in this structure.

Figure 13A:
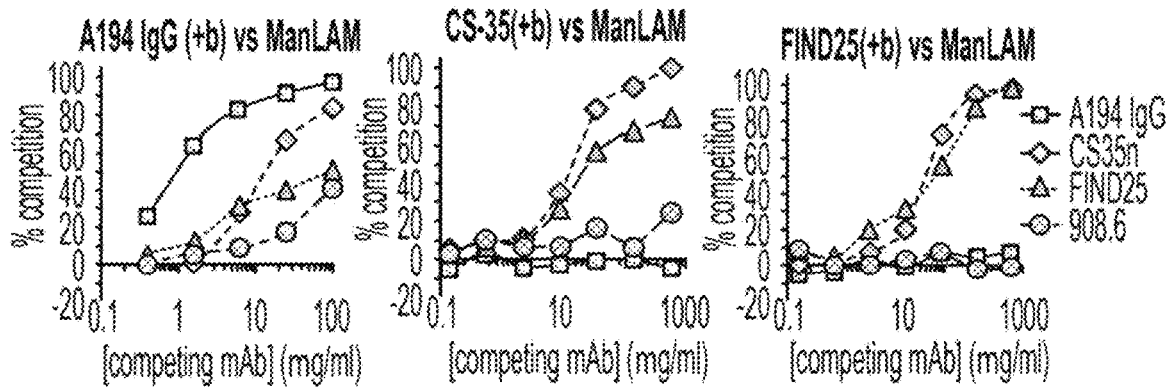
Figure 13B:
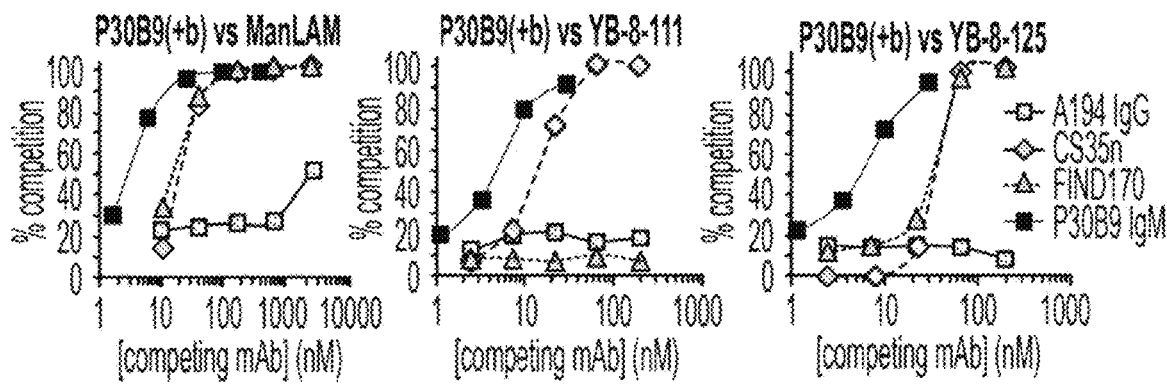
Figure 13C:
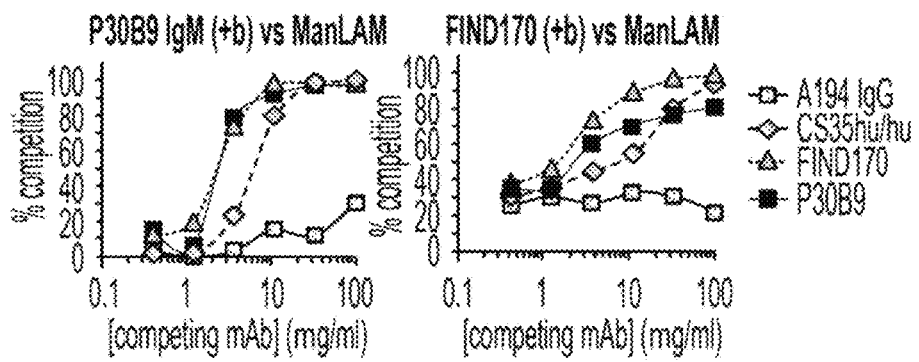

FIG. 13A-13C—Binding competition of biotinylated probe monoclonal antibodies with excess unmodified antibodies against natural LAM antigens and selected glycoconjugates. FIG. 13A—Competition of binding of biotinylated A194-01 IgG, CS-35 and FIND25 to MAnLAM by four mAbs; FIG. 13B—Competition of binding of FIND25 to both ManLAM and PILAM by three mAbs; FIG. 13C—Competition of binding of P30B9 IgM to MAnLAM and two synthetic glycoconjugate antigens by four mAbs.

Figure 14:
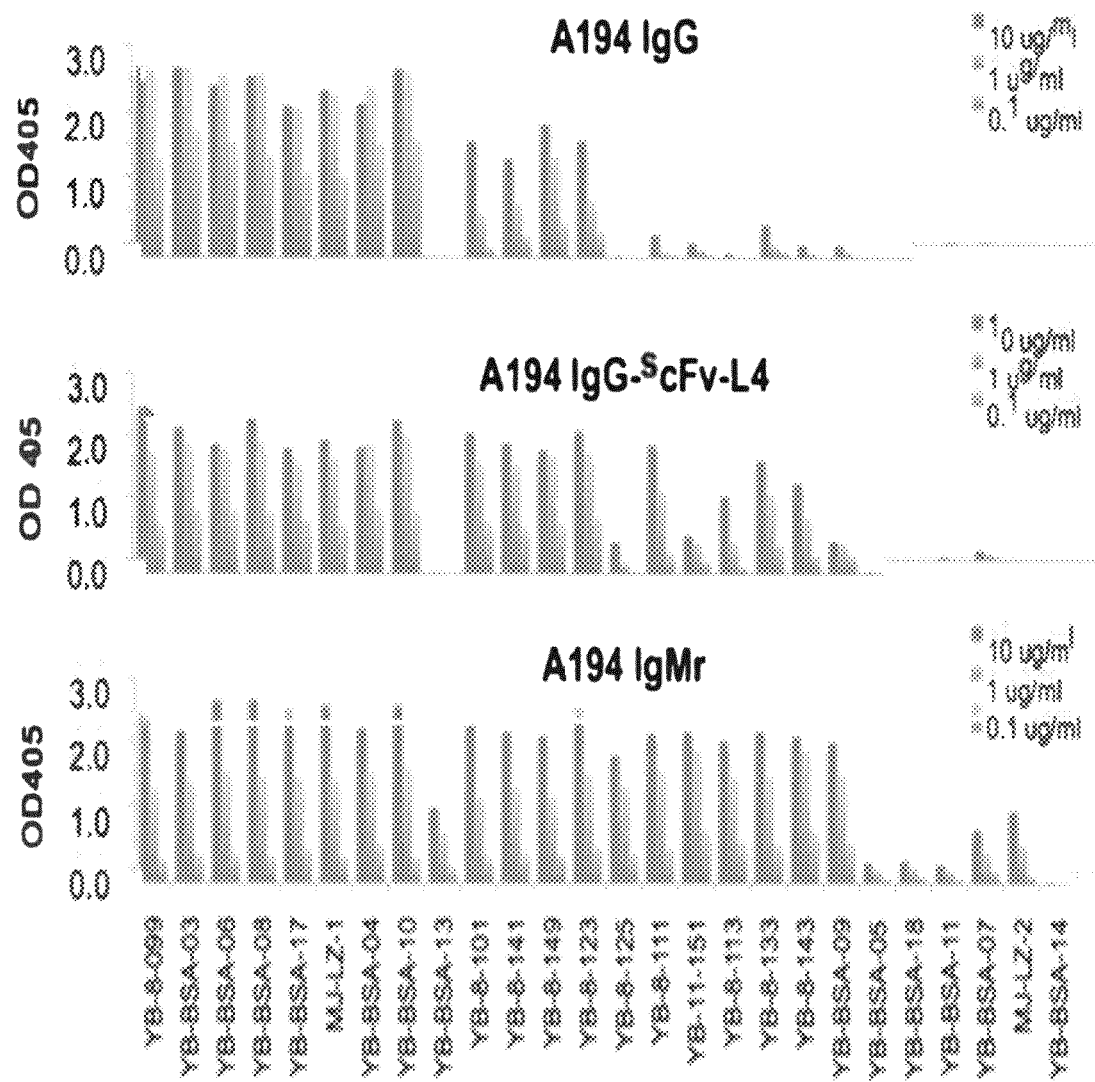

FIG. 14—Engineered variants and/or derivatives of A194-01 react with a broader range of glycoconjugates, including di- and tri-mannose substituted forms poorly recognized by the IgG isotype of A194-01.

Figure 15:
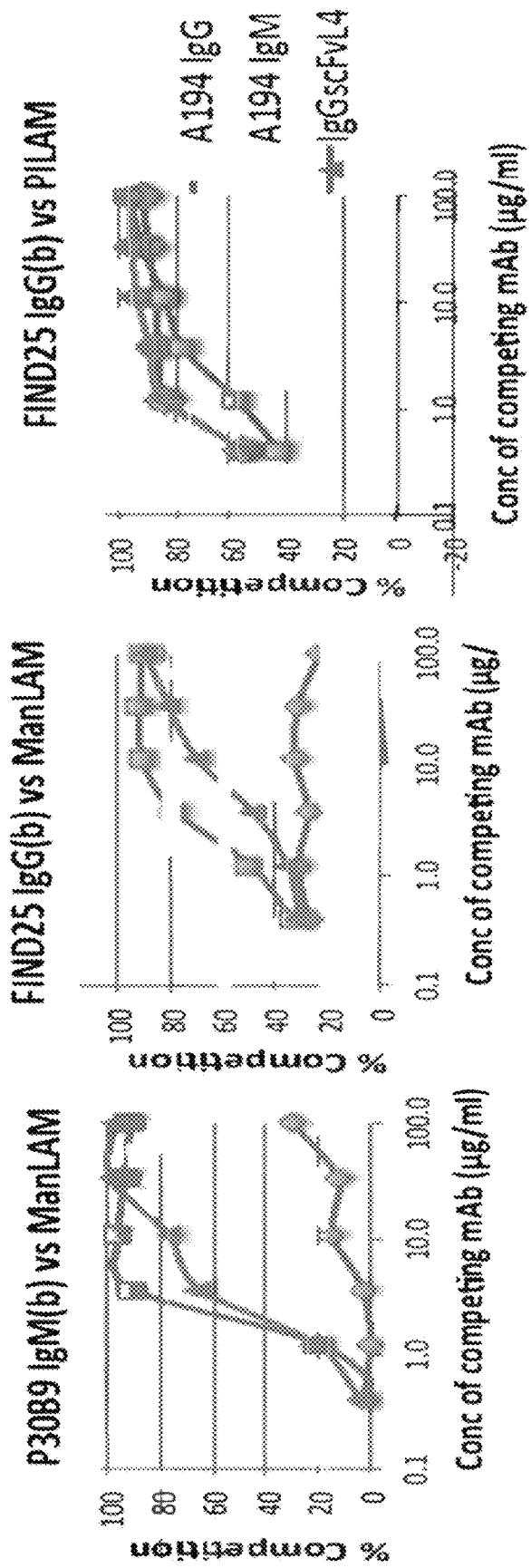

FIG. 15—Differential competition of A194-01 IgG and engineered variants and/or derivatives of A194-01 for binding of FIND25 and P30B9 IgM to ManLAM. Although A194 IgG doesn't compete with P30B9 or FIND25 against ManLAM, the multimeric forms do compete, consistent with the broader epitope specificity of these forms. As shown above, A194 IgG does compete well with FIND25 for PILAM.

Figure 16A:
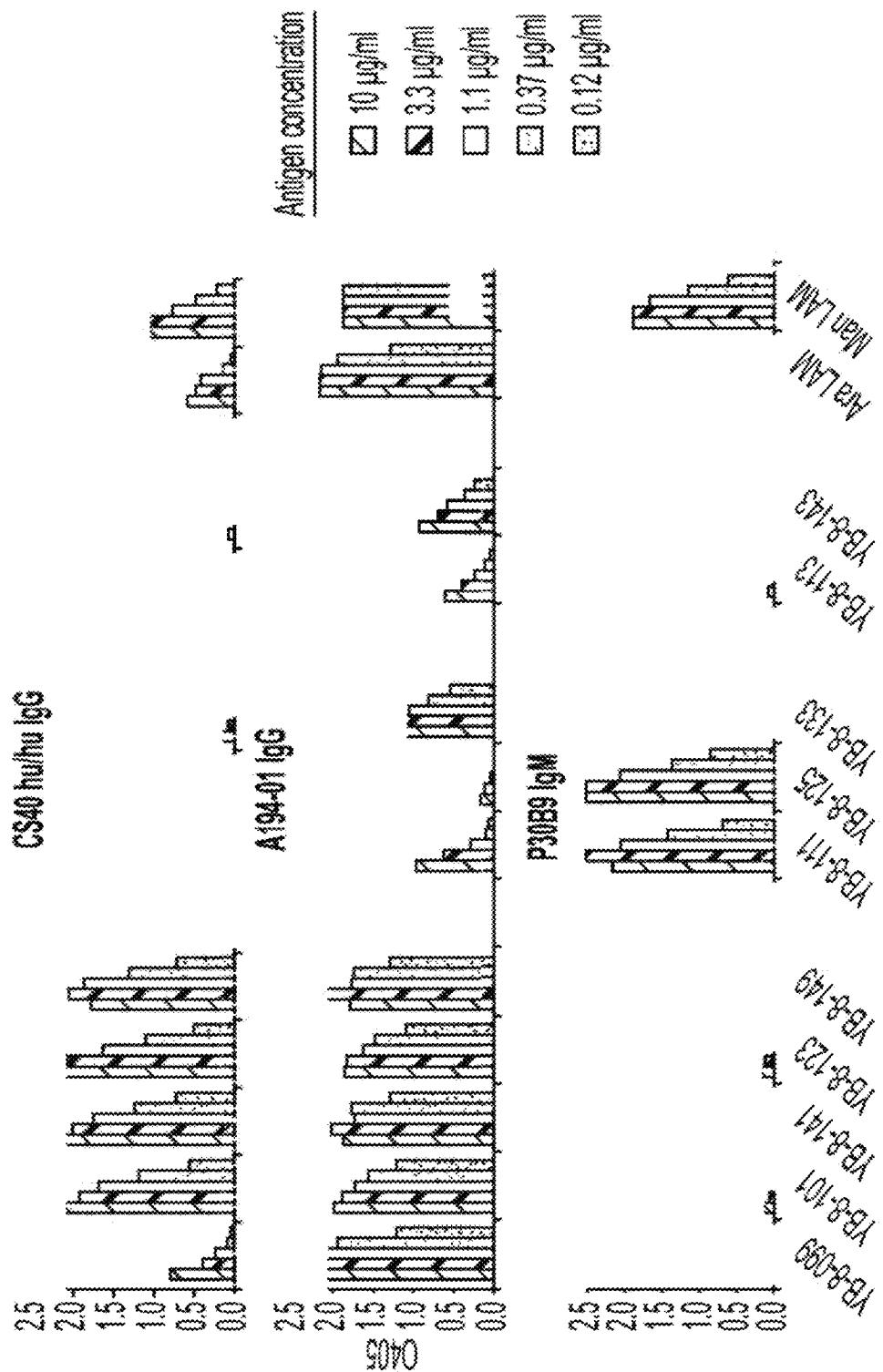
Figure 16B:
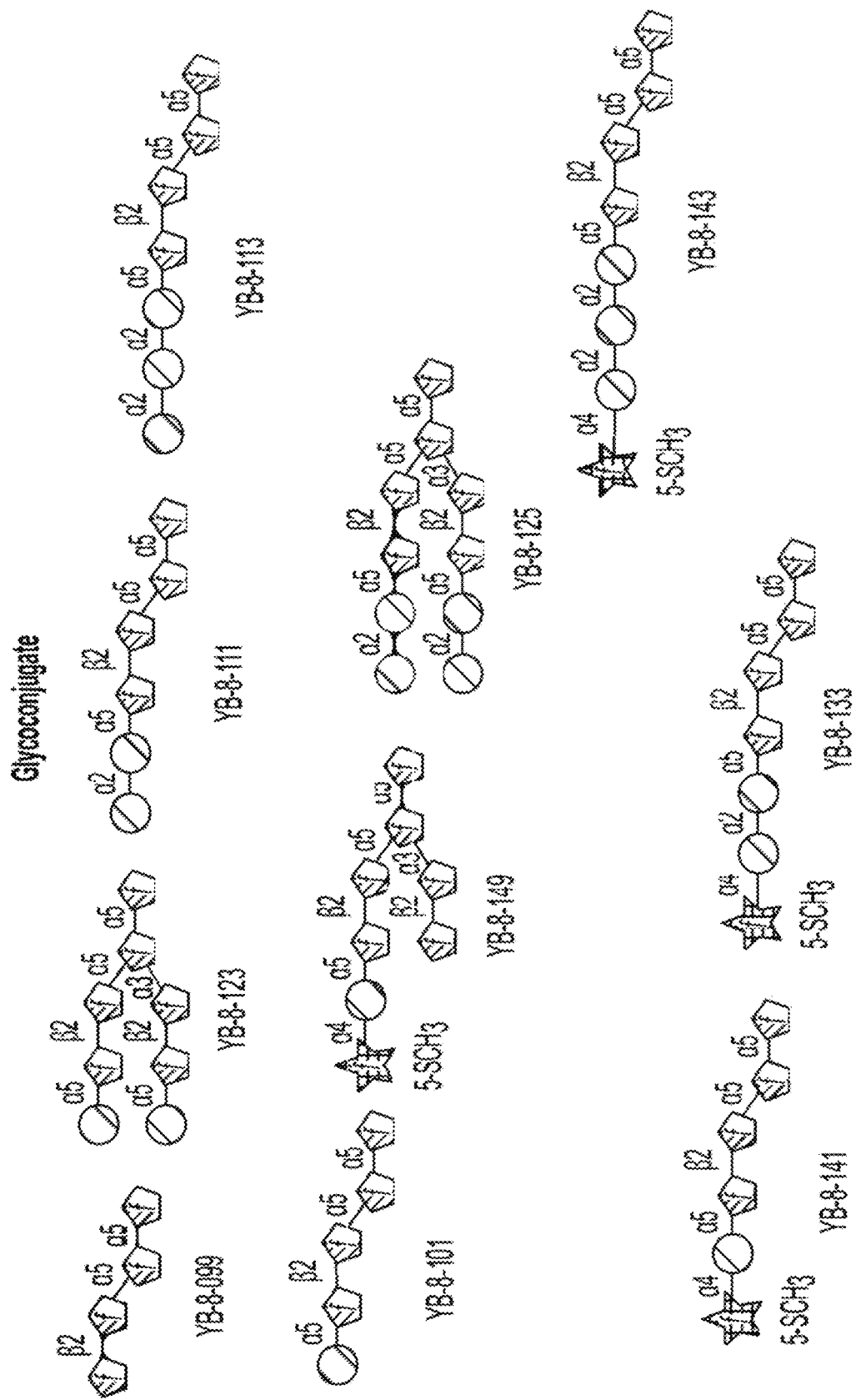

FIG. 16A-16B—Comparison of analysis of the effect of mannose-capping on the reactivity of CS-40, A194-01 and P30B9 mAbs. Antibody binding specificities were measured by ELISA against specific glyconjugates containing different mannose substitutions. The antibody titrations and the structures of the mannose-containing glycan antigens are shown.

Figure 17A:
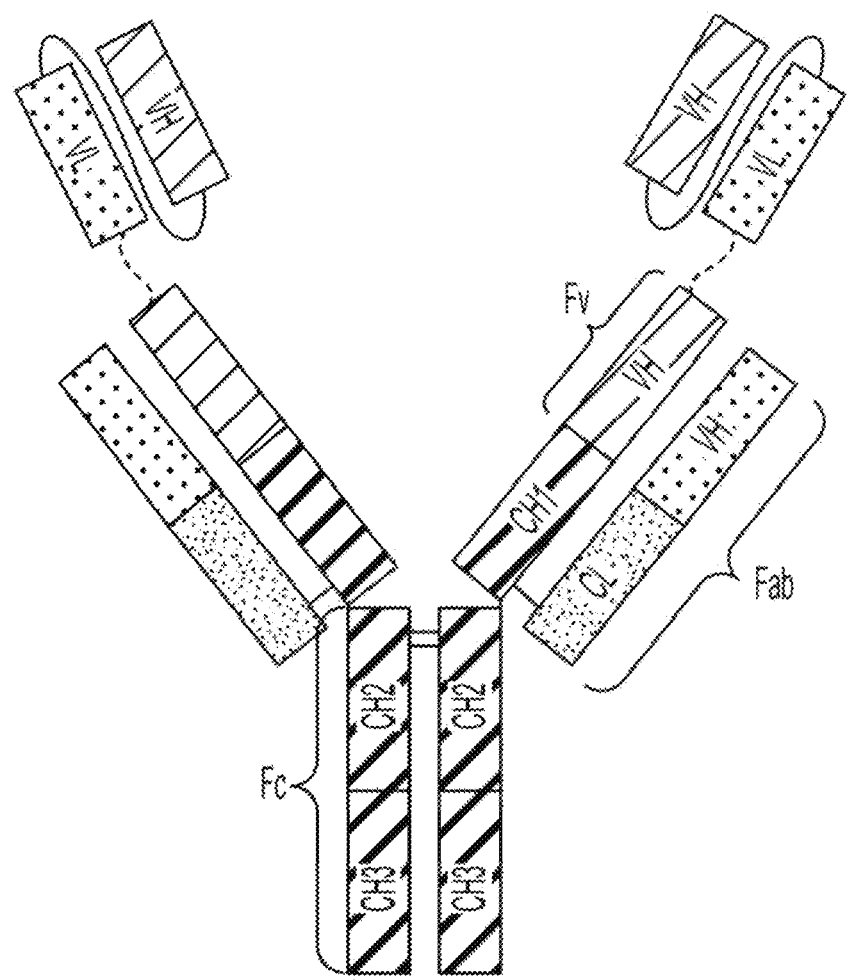
Figure 17C:
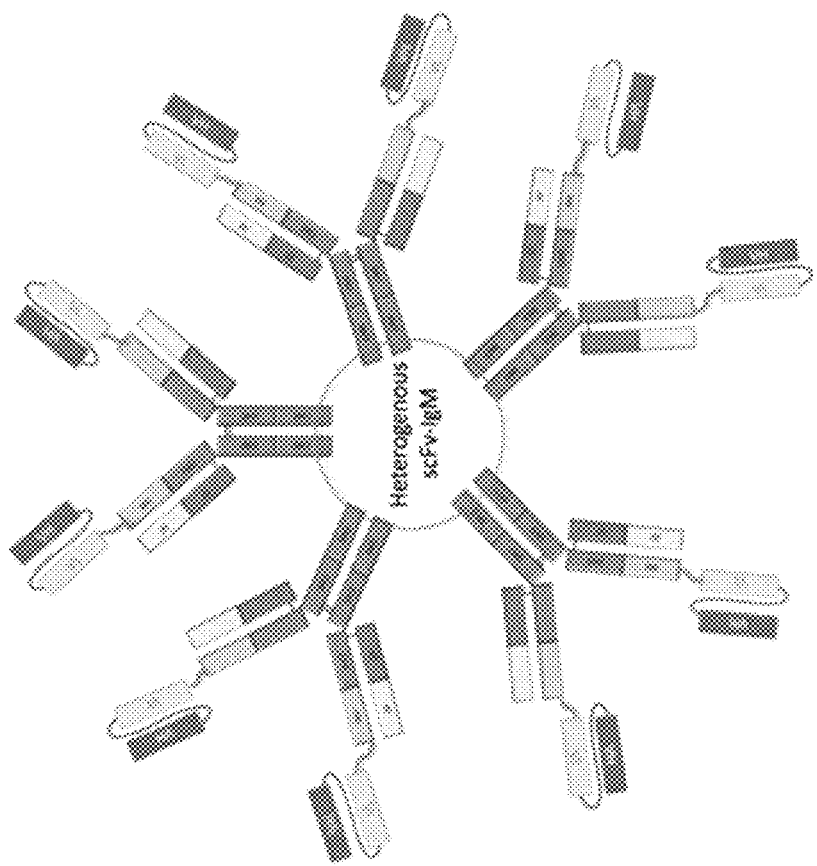
Figure 17B:
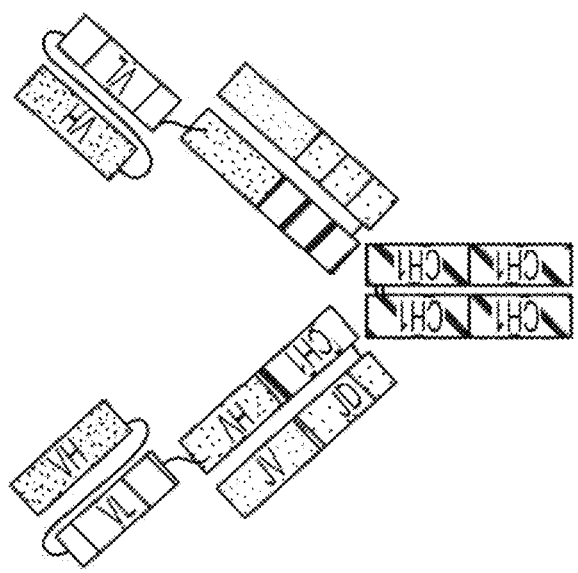

FIGS. 17A, 17B, 17C. Homologous scFv-IgG. In this example, both the IgG and scFv domains are derived from the same antibody. This results in an increased valency (tetravalent vs. divalent) but does not directly modify the target specificity. FIG. 17B. Heterologous scFv-IgG. In addition to the increase in valency, there is also a broadened specificity introduced, which may allow recognition of distinct epitopes in a single antigen molecule. FIG. 17C. Heterologous scFv-IgM. In this formulation a distinct scFv is combined with an IgM construct. One example would be joining of the A194-01 scFv with the P30B9 IgM. In addition to the increase in valency, this would introduce an additional epitope specificity, which may allow multivalent recognition of distinct epitopes that may not be recognized by the homologous scFv-IgM, and lead to increased affinities.

Figure 3:
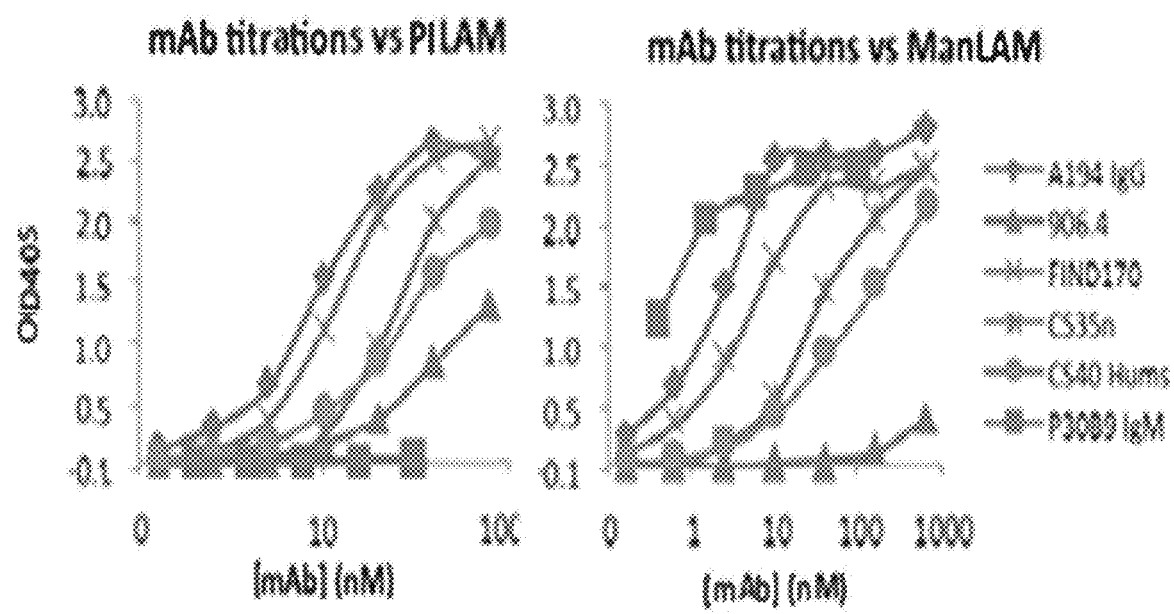
FIG. 3—Comparing the reactivity of 2 human mAbs and 4 mouse mAbs vs PILAM in the left panel and vs. ManLAM isolated from the H37Rv strain of *Mycobacterium tuberculosis* in the right panel. Curves were plotted using the molar concentrations of the antibodies, to control for the different molecular weights of these reagents FIG. 4A-1-4A-4—Structures of 25 synthetic oligosaccharides representing microbial glycan structures related to motifs present in LAM. These structures were coupled to BSA carrier protein and used to probe epitope specificity.
Figures 3, 4A:
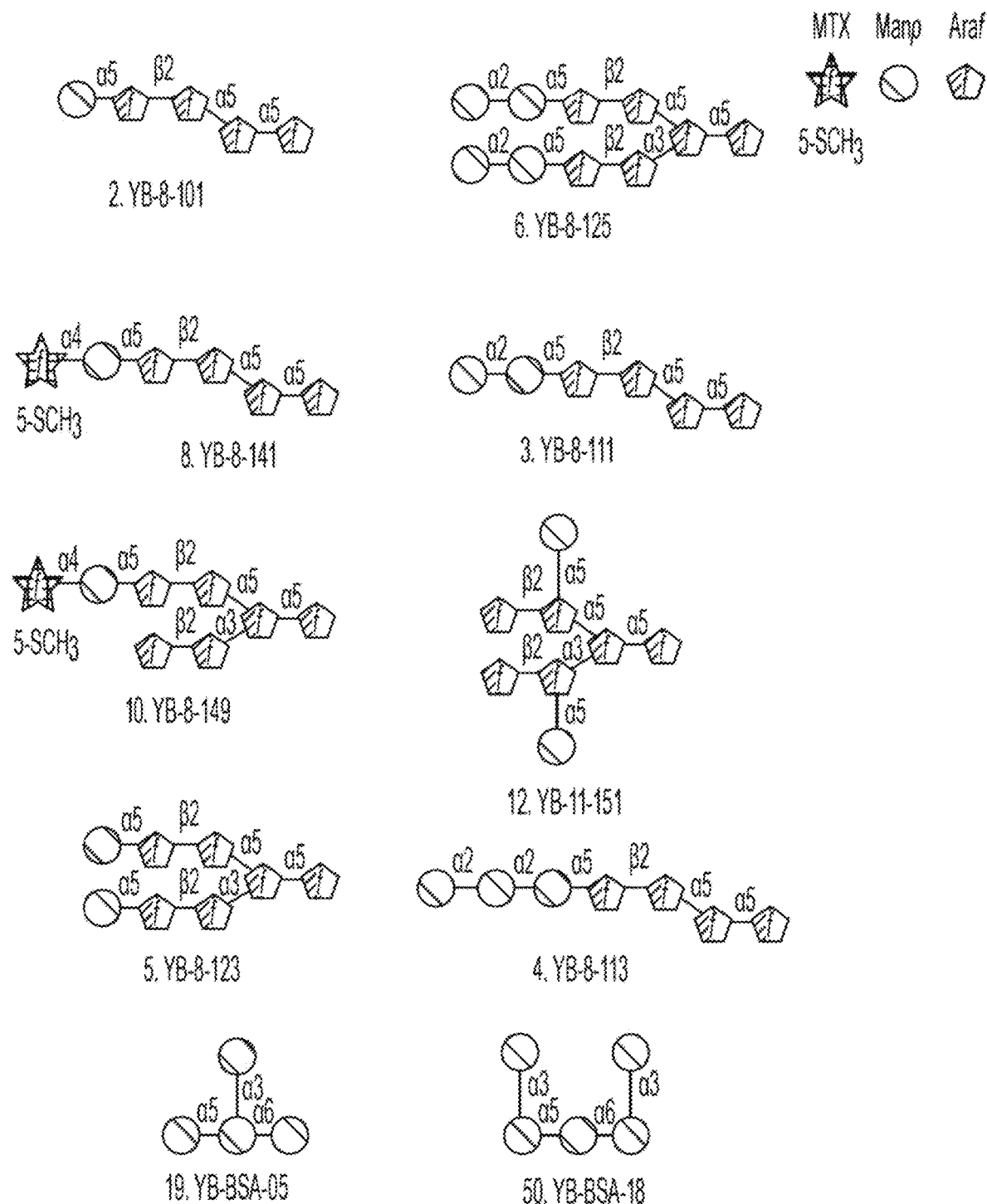
Figures 1, 4B:
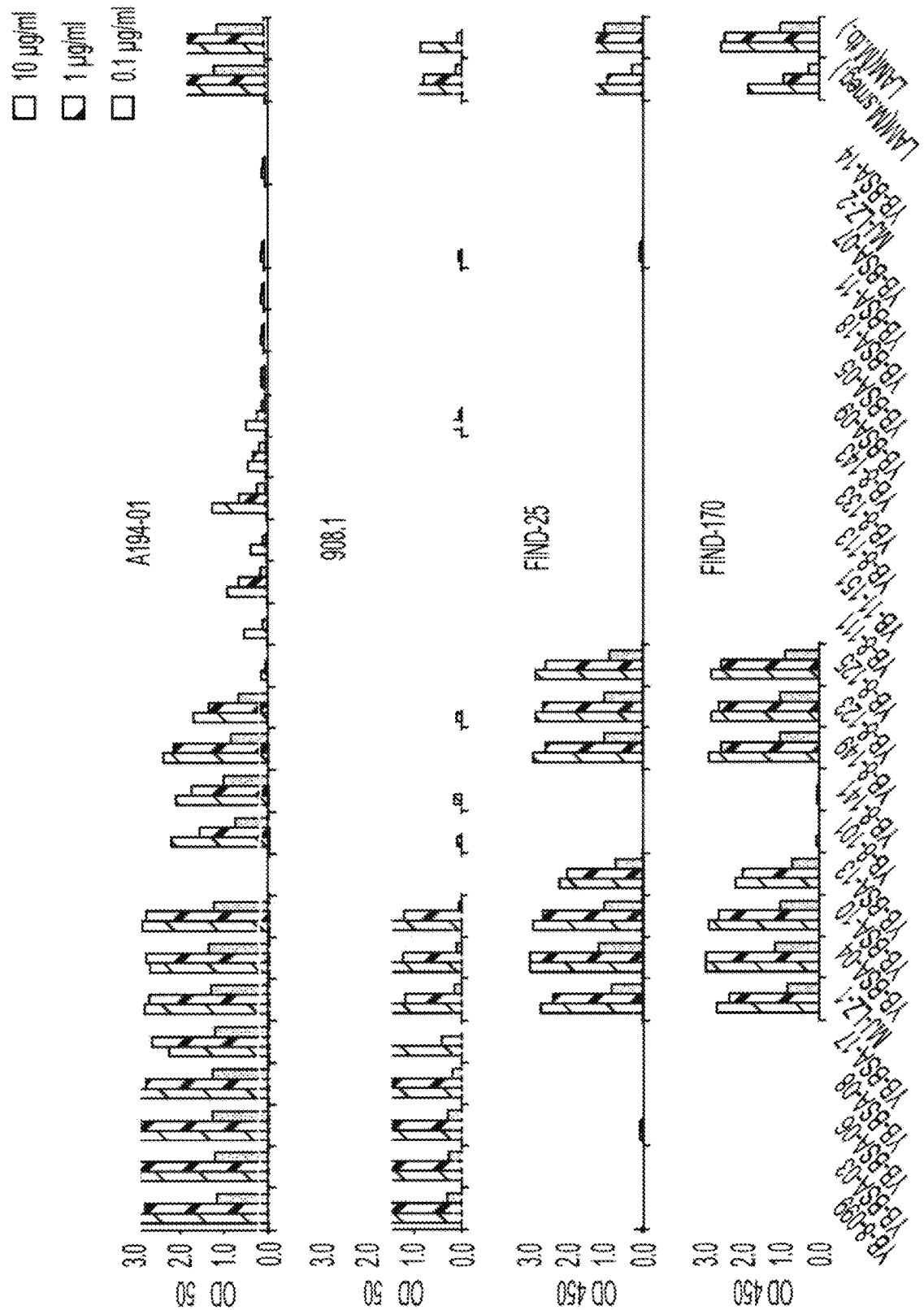
Figure 6:
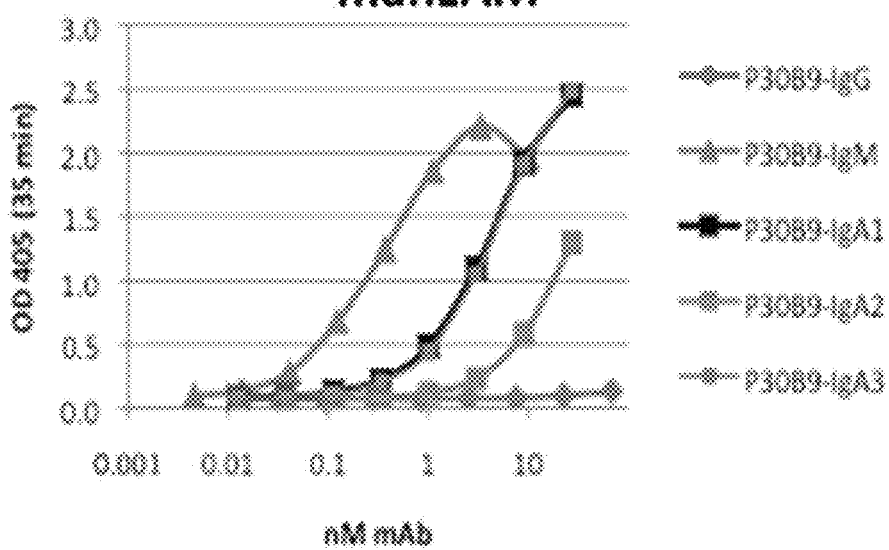
FIG. 6—Binding curves of different isotypes of P30B9 to ManLAM showing greatest activity for IgM form followed by IgA forms, with no reactivity for the IgG form.
Figure 7:
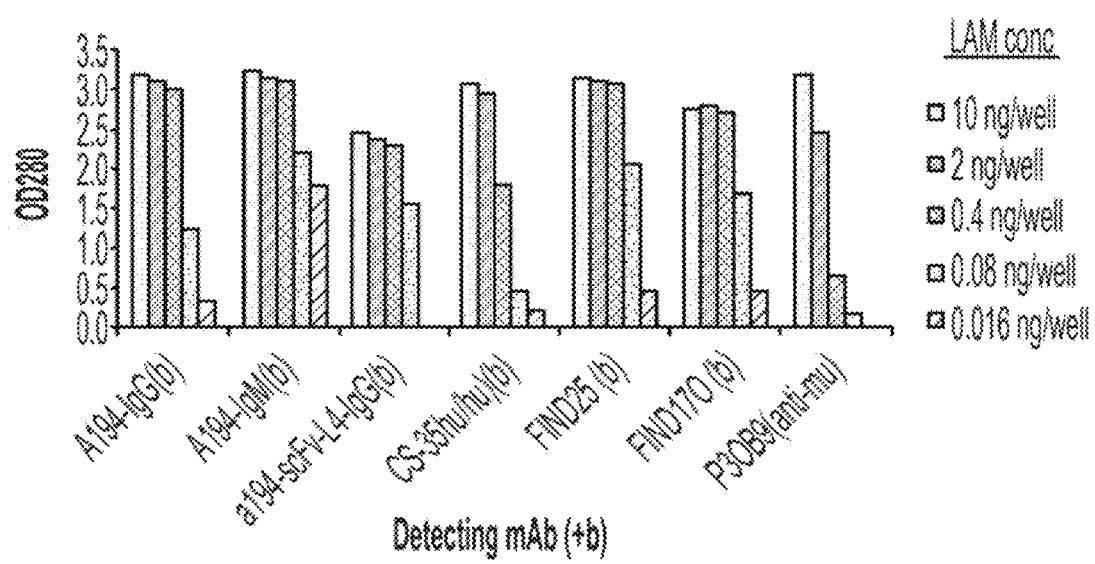
FIG. 7—Comparison of efficiency of biotinylated monoclonal antibody probes at detecting soluble ManLAM in CS-35 capture assay, in which the indicated concentration of ManLAM was captured by CS-35 and detected by the indicated mAbs labeled with biotin.
Figure 8A:
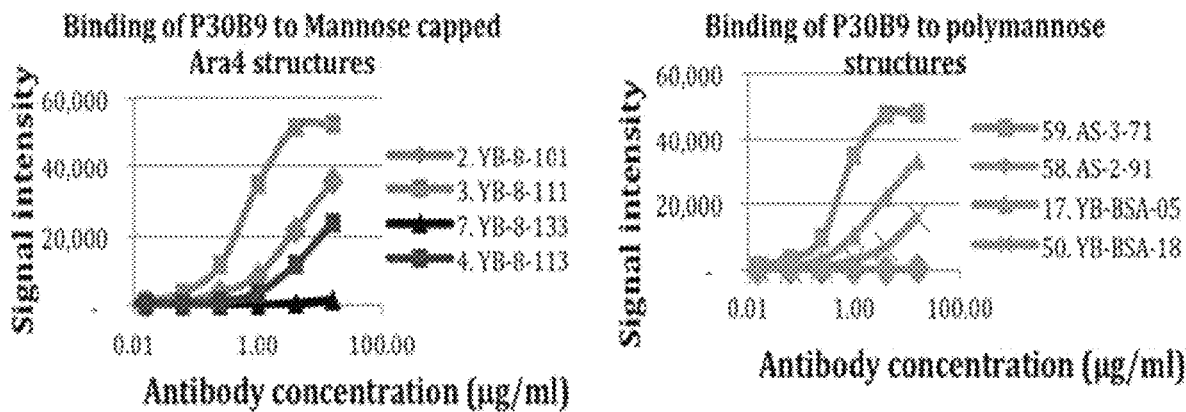
Figures 1, 8B:
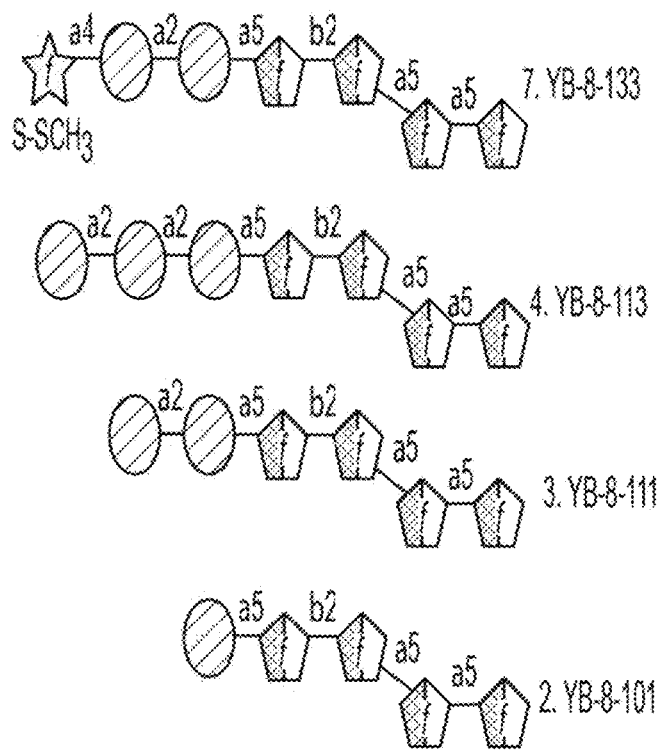
Figures 2, 8B:
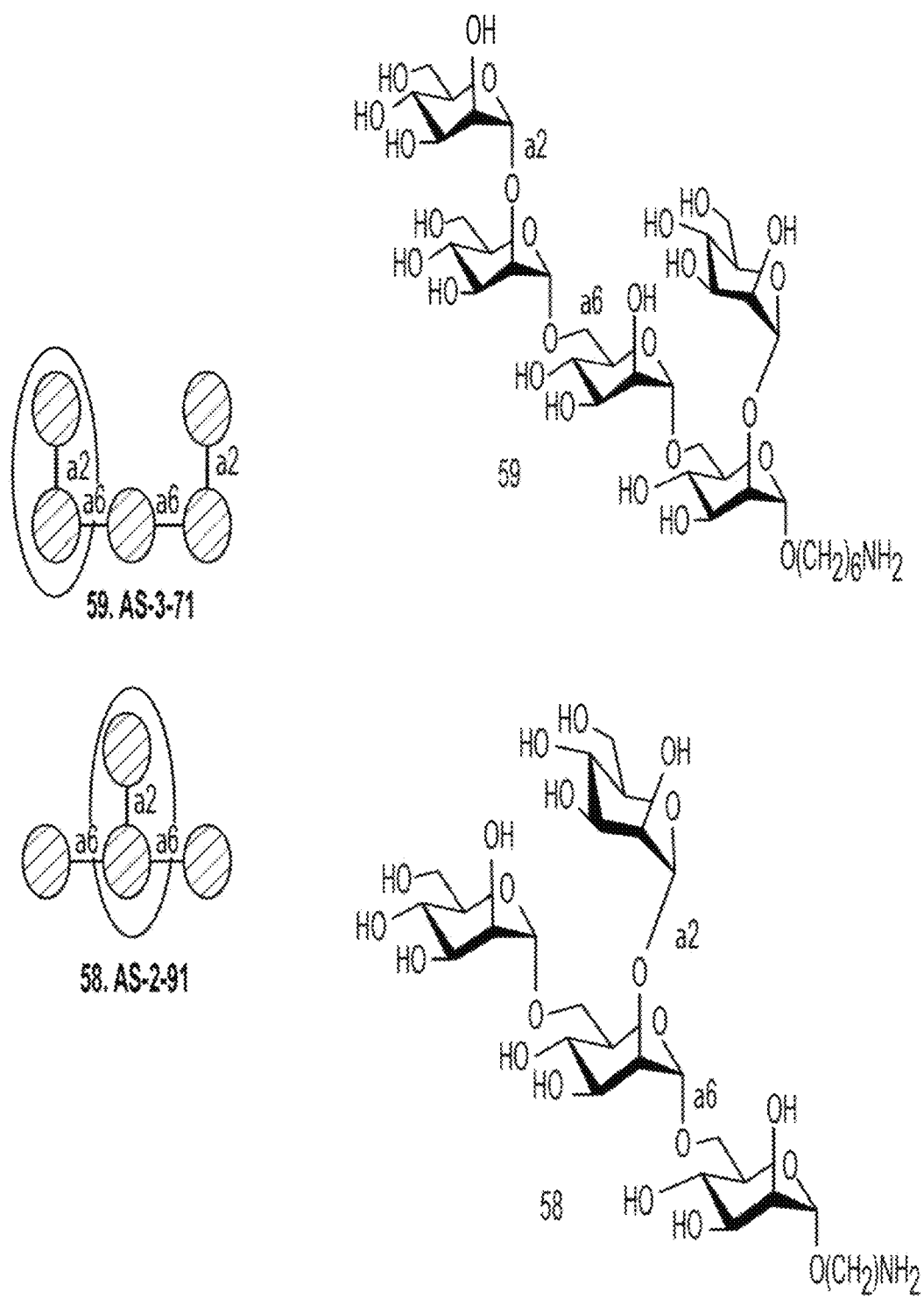
Figures 3, 8B:
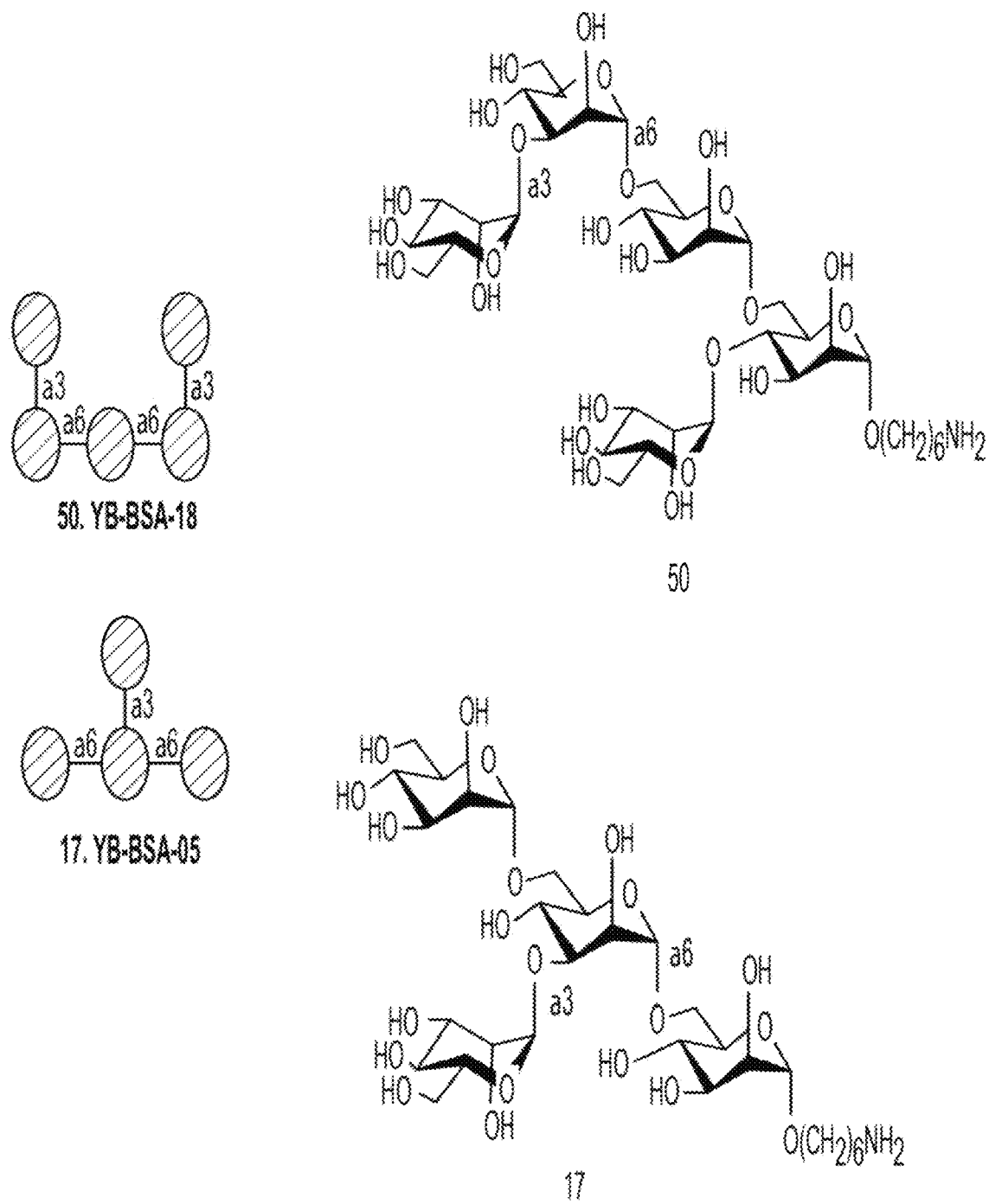
Figure 18A:
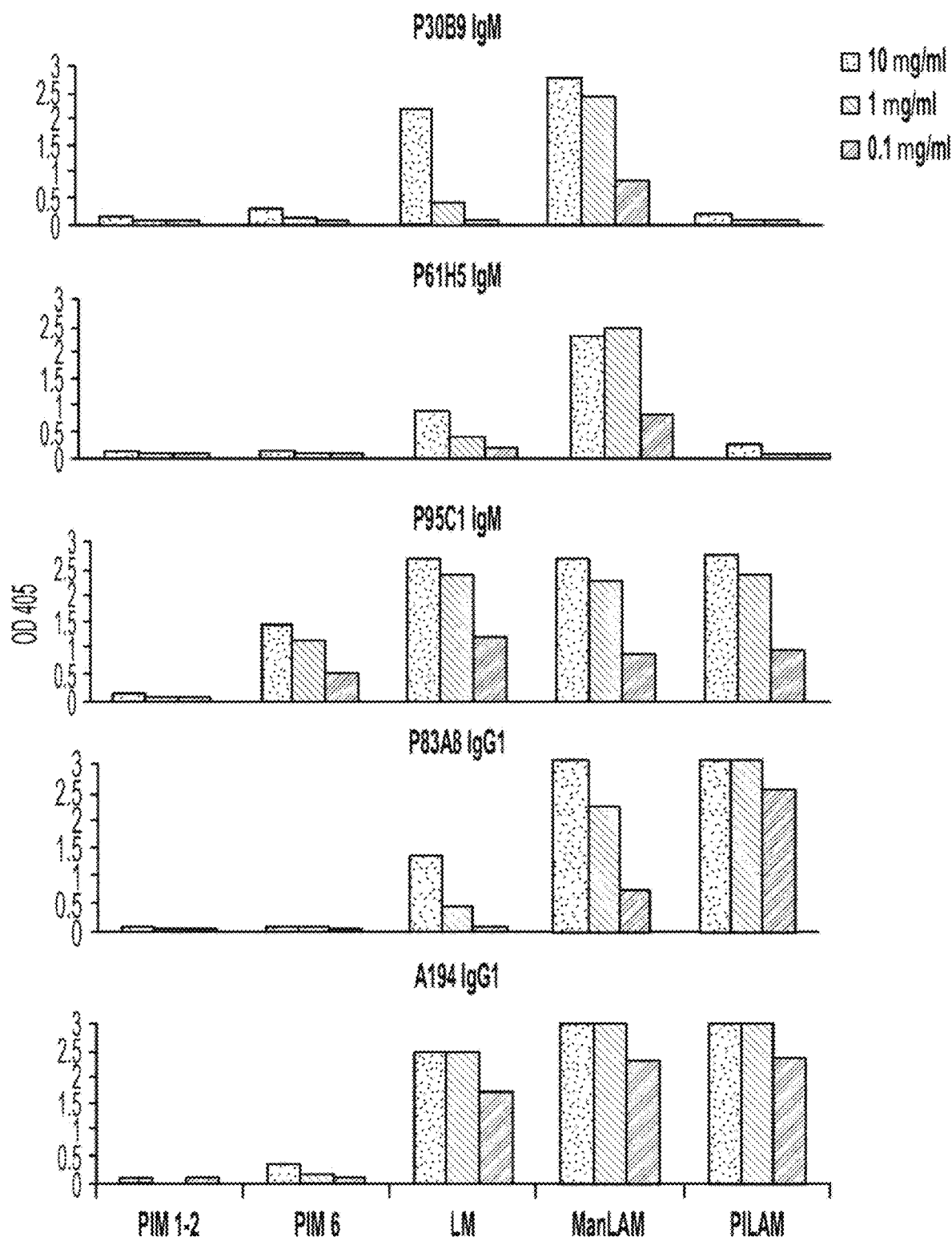
Figure 18B:
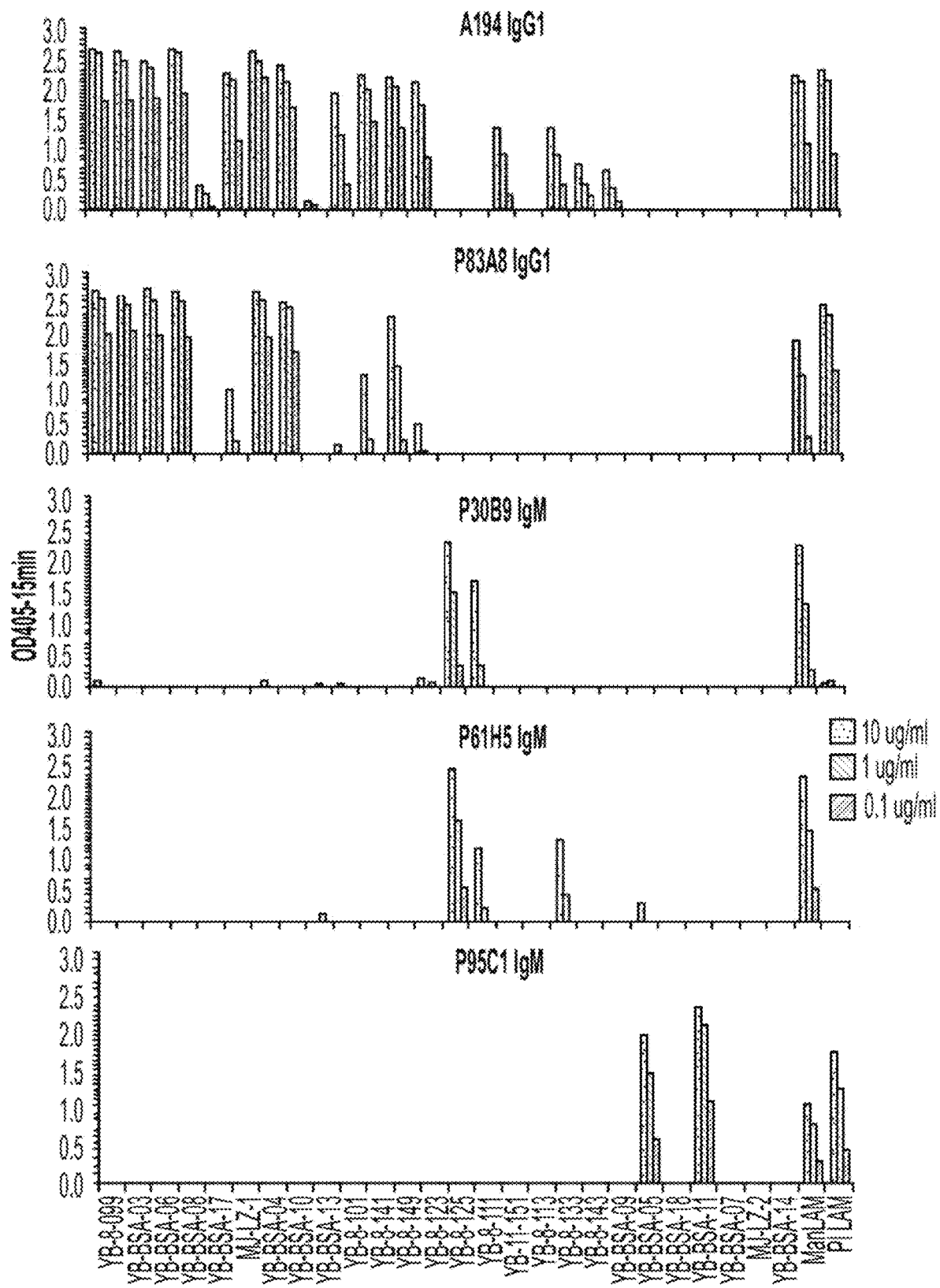
Figures 2, 18C:
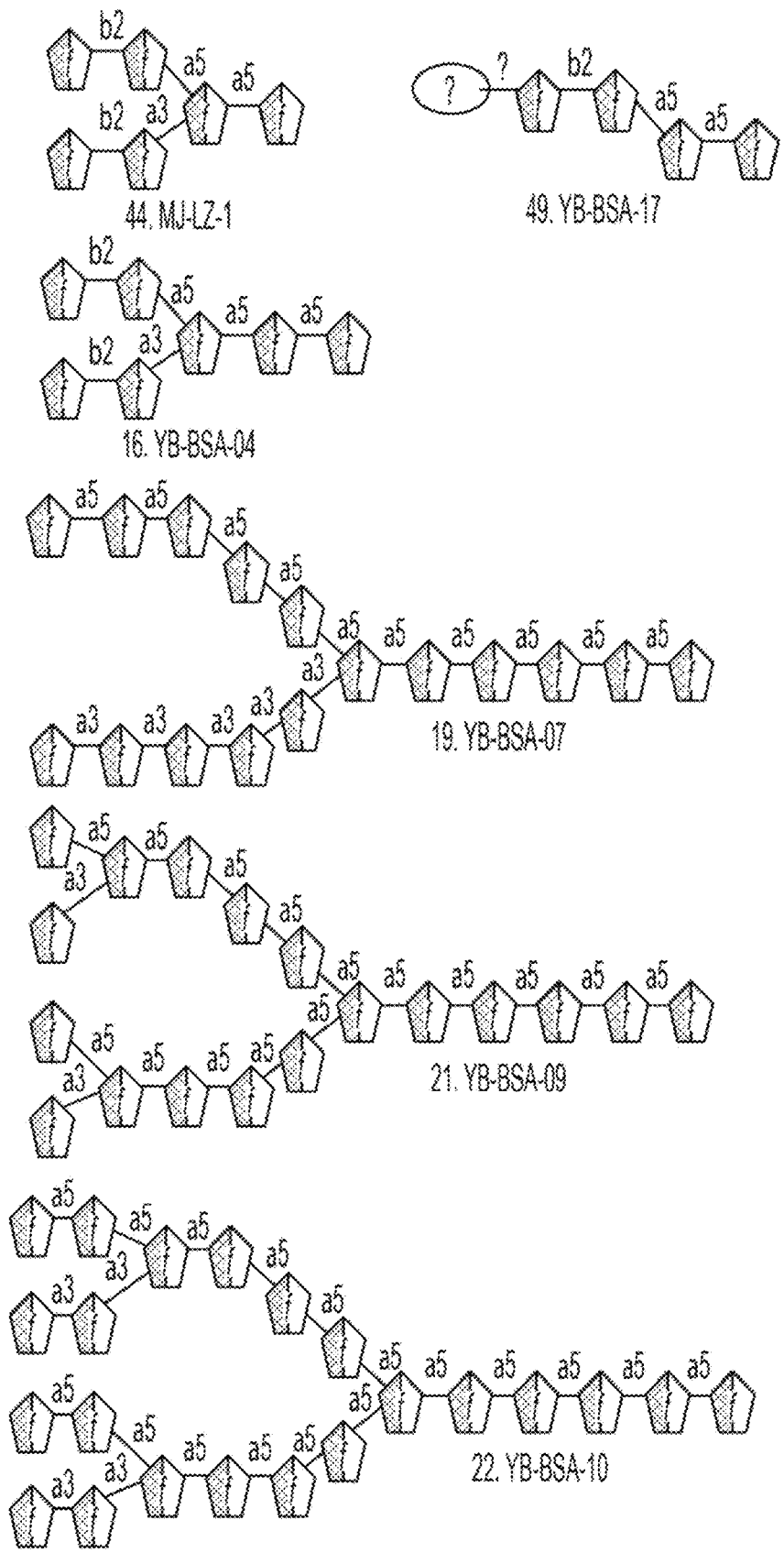
Figure 18C:
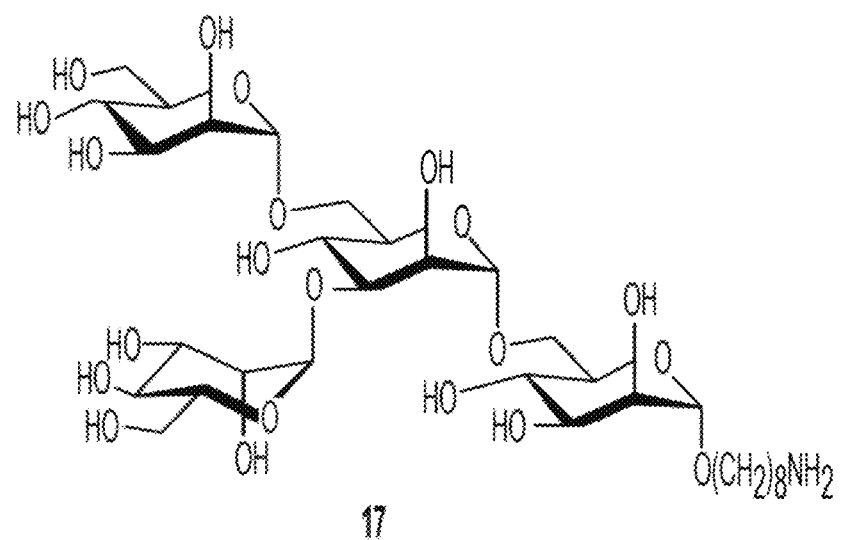
Figure 5:
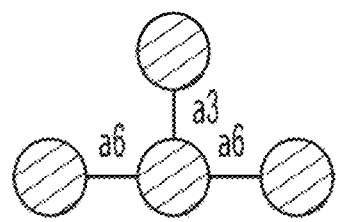
Figure 18C:
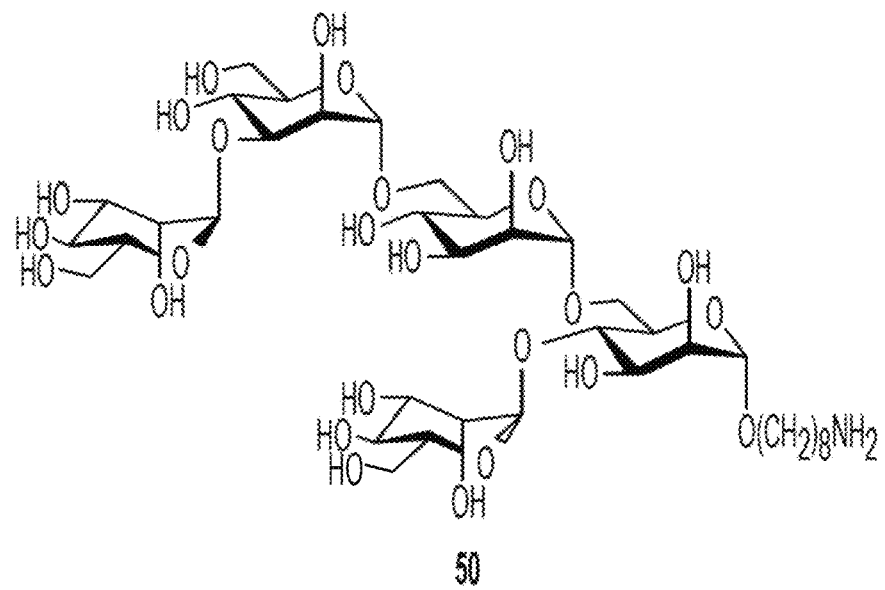
Figure 6:
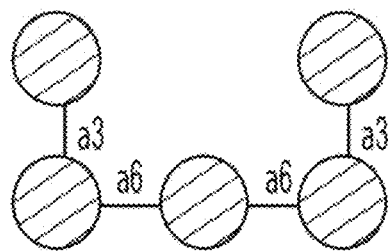
Figure 18C:
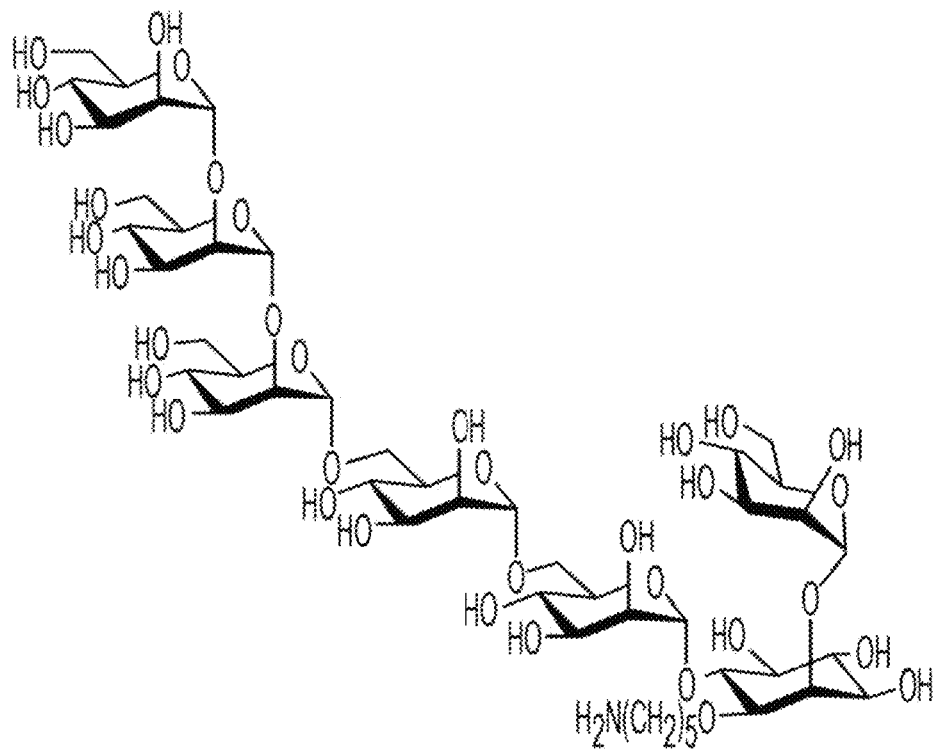
Figure 7:
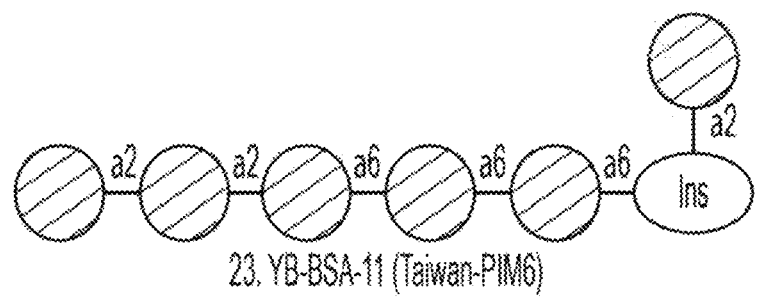

FIGS. 18A-18C-1-18C-7 —_Mapping of epitopes recognized by new mAbs. The epitope specificity of P95C1 was compared to that of two previously described mAbs, A194-01 and P30B9, and two new mAbs, P61H5 and P83A8, that recognize epitopes related to those two previously described mAbs. FIG. 18A. Reactivity of LAM-specific mAbs for LAM precursor molecules. P30B9 and P61H5 were specific for ManLAM over PILAM, while A194-01, P83A8 and P95C1 recognized both forms of LAM. P95C1 also bound efficiently with LM and PIM6. The weak reactivity of the other mAbs for LM and PIM6 is die at least in part, to contamination of these materials by ManLAM. FIG. 18B. Reactivity of synthetic LAM-derived glycoconjugates. FIG. 18C-1-18C-7. In contrast to previously known mAbs, P95C1 was the only antibody that did not recognize any of the polyarabinose structures, but reacted specifically with two poly-mannose structures, YB-BSA-05 and YB-BSA-11, that resembled structures present in PIM6 and in the mannan domains at the base of LM and LAM.

Figure 19:
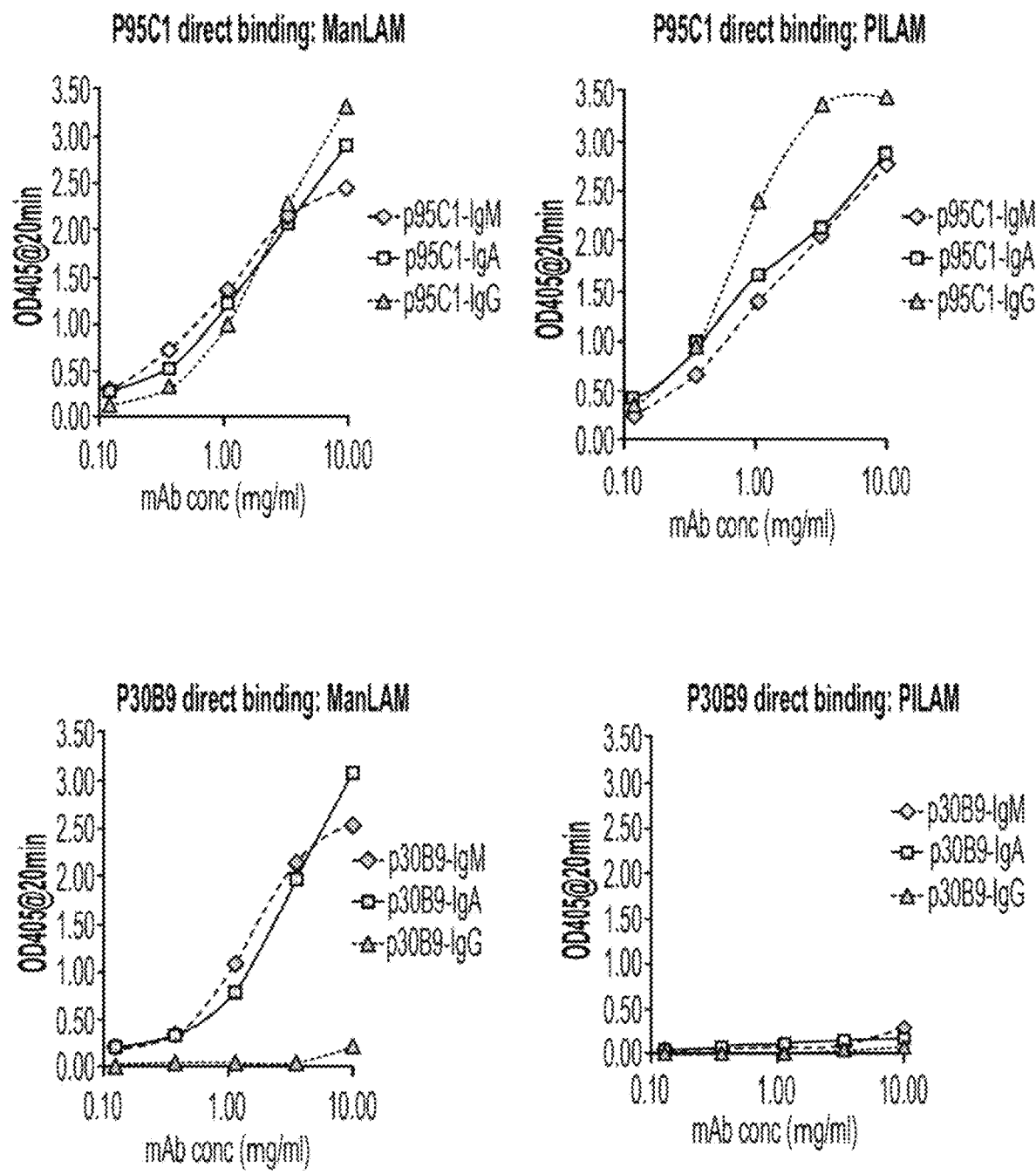

FIG. 19—Effect of isotype switching on binding of P95C1 and P30B9 to ManLAM and PI-LAM. For P95C1, IgM, IgA and IgG isotypes all have comparable binding activity for both ManLAM and PILAM, unlike P30B9 which react only with ManLAM and only in IgM and IgA forms but not as IgG.

Figures 20A, 20B:
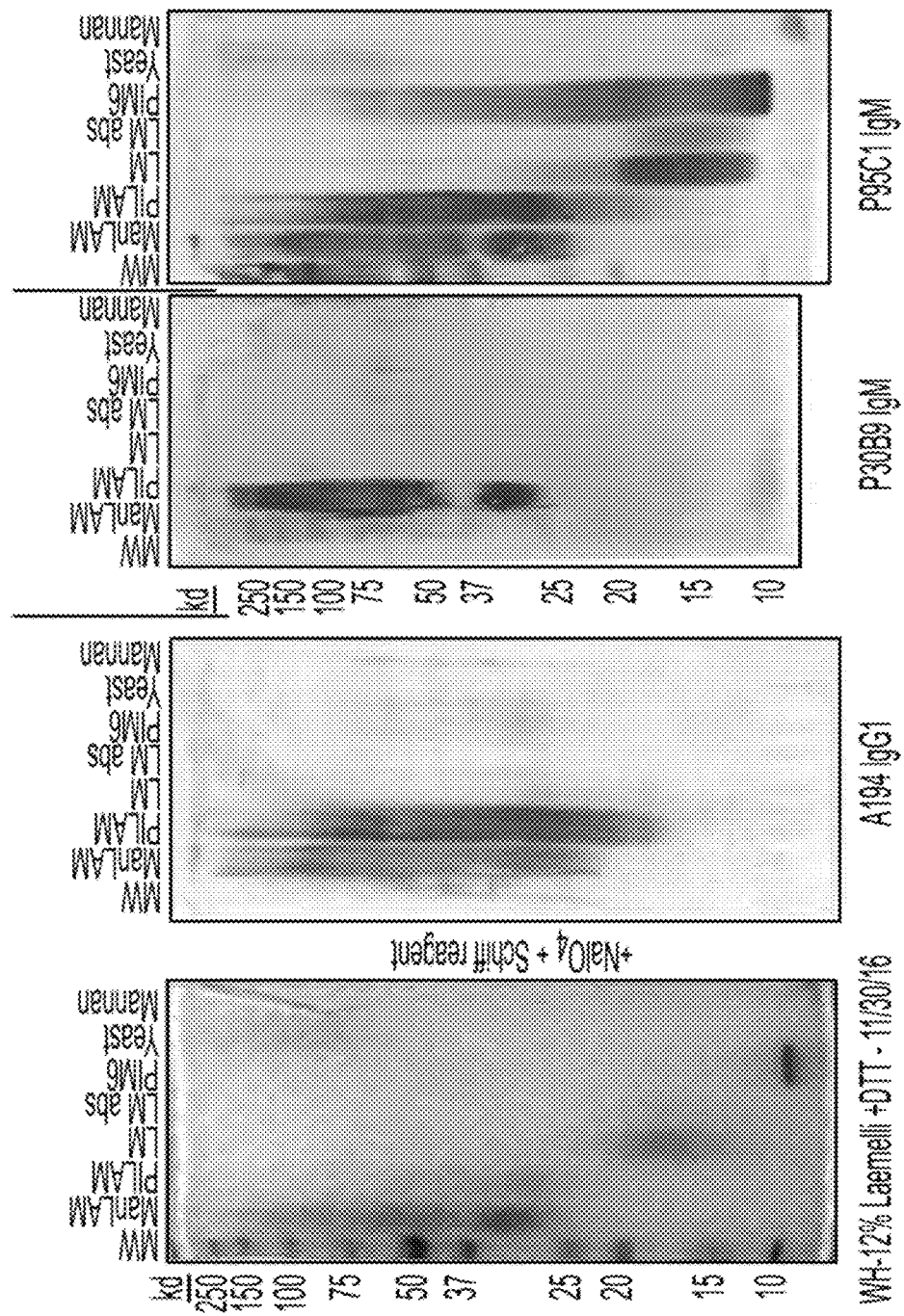

FIGS. 20A-20B—Western blot analysis of crossreativity of P95C1 with LAM and additional M. tb glycolipids. FIG. 20A Purified LAM associated glycolipids were separated on 12% SDS-PAGE gel followed by oxidation and staining of sugar molecules with periodic acid-Schiff stain, to reveal material containing reactive glycans. FIG. 20B Parallel blots were probed with mAbs A194 IgGI, P30B9 IgM, and P95C1 IgM followed by alkaline phosphatase conjugated anti human IgG and IgM secondary antibodies and treatment with bcip/nbt color development substrate. A194-01 crossreacts with ManLAM from M. tb and PILAM from M.smeg. P30B9 is specific forM. tb manLAM. P95C1 recognizes both species of LAM, as well as LM and PIM6 isolated from M. tb. Weak staining by A194-01 of bands in LM and PIM6 that co-migrate with LAM is apparently due to minor contamination of these samples with LAM.

Figure 21:
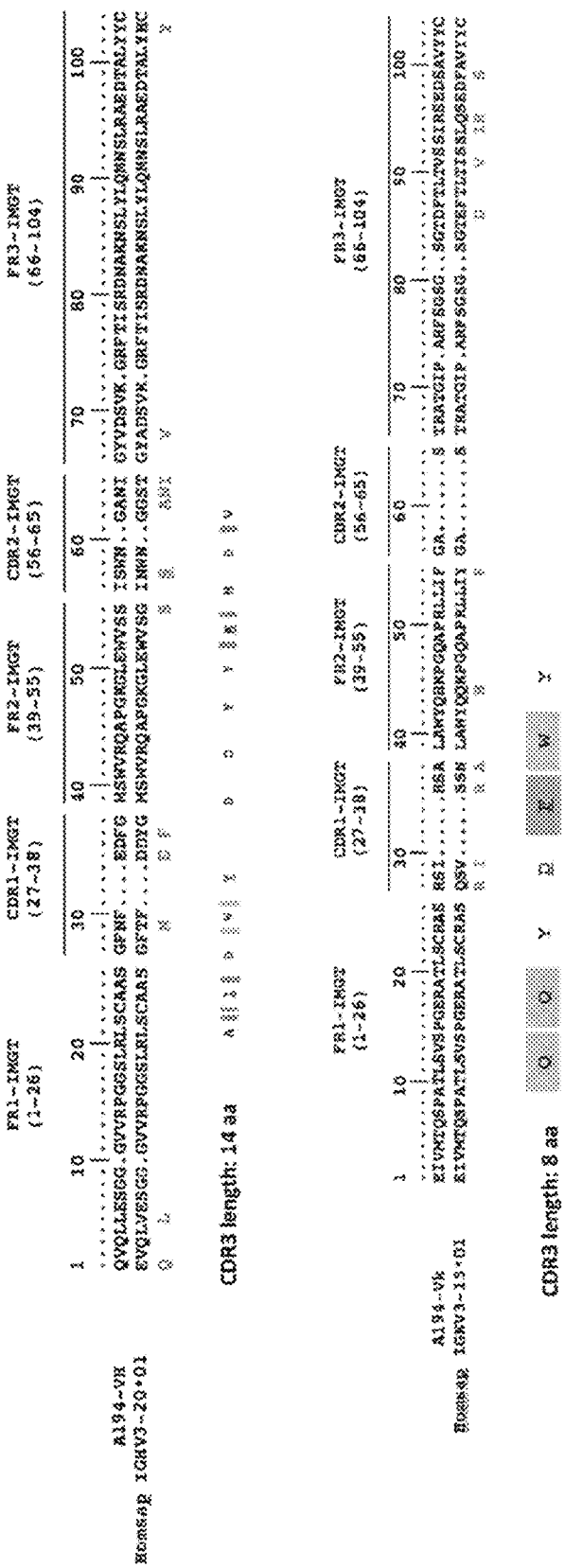

FIG. 21—Alignments of amino acid sequences for A194 heavy chain and light chain variable regions sequences and their comparison with their closest germline sequences. In the top alignment, from the top, the first amino acid sequence (A194-VH) is an A194 heavy chain variable region sequence without the CDR3 sequence (SEQ ID NO:23). The heavy chain variable region sequence without CDR3 is SEQ ID NO:21. In the top alignment, the second amino acid sequence (germline Homsap IGHV3-20*01) is SEQ ID NO:22. In the top alignment, the third amino acid sequence is the CDR3 of a A194 heavy chain variable region and is SEQ ID NO:23. In the bottom alignment, from the top, the first amino acid sequence (A-194-Vk) is an A194 light chain variable region without the CDR3 sequence (SEQ ID NO: 26). The light chain variable region sequence without CDR3 is SEQ ID NO:24. In the bottom alignment, the second amino acid sequence (germline Homsap IGKV3-15*01) is SEQ ID NO:25. In the bottom alignment, the third sequence is the CDR3 of a A194 light chain variable region and is SEQ ID NO:26.

Figure 22:
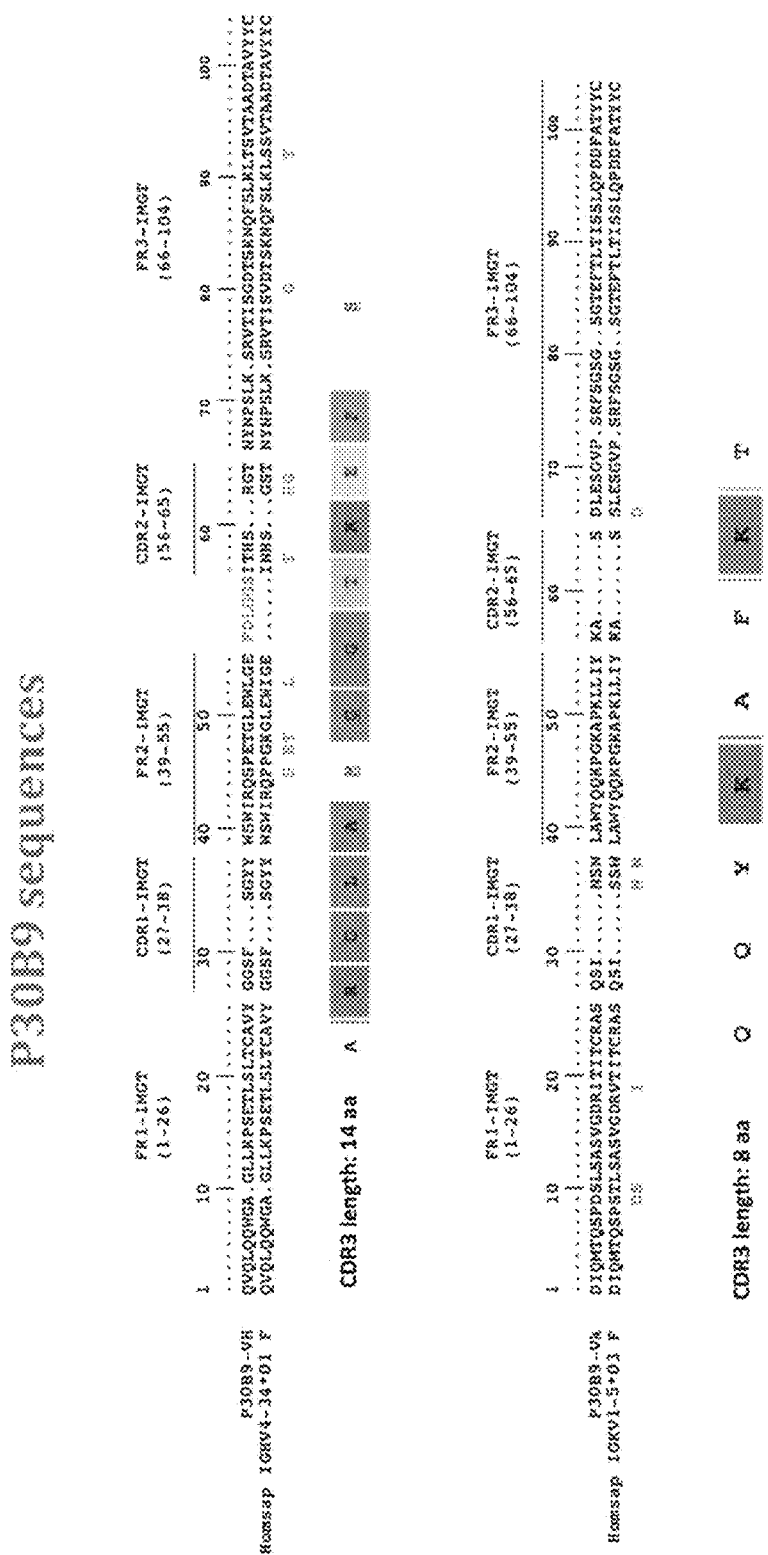

FIG. 22—Amino acid sequences for P30B9-IgM heavy chain and light chain variable region sequences and their comparisons with their closest germlines. In the top alignment, from the top, the first amino acid sequence (P30B9-Vh) is a P30B9-IgM heavy chain variable region sequence without the CDR3 sequence (SEQ ID NO:29). The heavy chain variable region sequence without CDR3 is SEQ ID NO: 27. The second amino acid sequence (Homsap IGHV4-34*01 F) is SEQ ID NO:28. The third amino acid sequence is of a P30B9-IgM heavy chain variable region and is SEQ ID NO:29. In the bottom alignment from the top, the first amino acid sequence (P30B9-Vk) is a P30B9 light chain variable region without the CDR3 sequence (SEQ ID NO:32). The light chain variable region sequence without CDR3 is SEQ ID NO:30. In the bottom alignment, the second amino acid sequence (germline Homsap IGKV1-5*03) is SEQ ID NO:31. In the bottom alignment, the third sequence is the CDR3 of a P30B9 light chain variable region and is SEQ ID NO:32.

Figure 23:
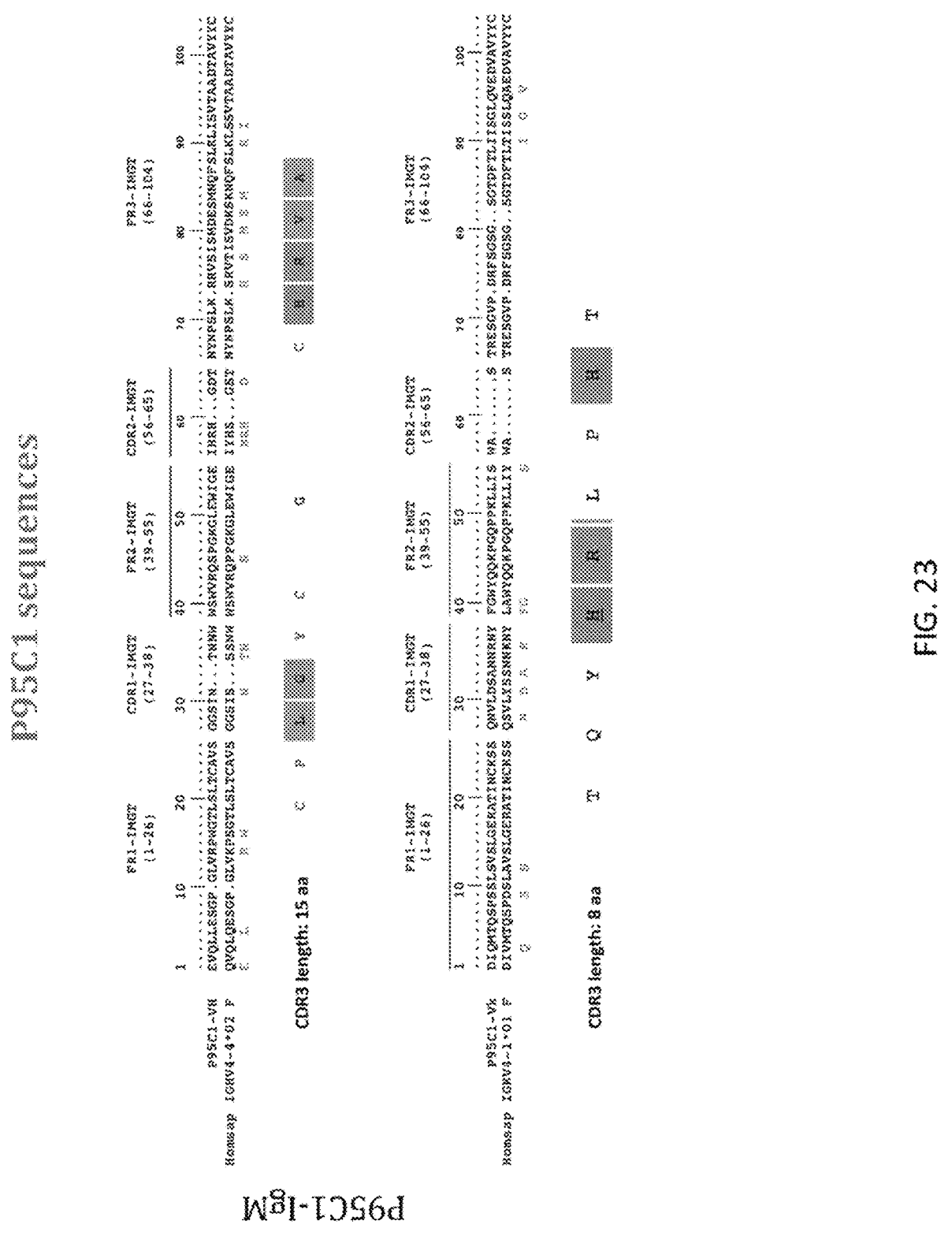

FIG. 23—Alignments of amino acid sequences for P95C1-IgM heavy chain and light chain variable regions sequences and their comparison with their closest germline sequences. In the top alignment, from the top, the first amino acid sequence (P95C1-VH) is an P95C1 heavy chain variable region sequence without the CDR3 sequence (SEQ ID NO:18). The heavy chain variable region sequence without CDR3 is SEQ ID NO:33. In the top alignment, the second amino acid sequence (germline Homsap IGHV4-4*02) is SEQ ID NO:34. In the top alignment, the third amino acid sequence is the CDR3 of a P95C1-Gm heavy chain variable region and is SEQ ID NO:18. In the bottom alignment, from the top, the first amino acid sequence (P95C1-Vk) is a P95C1 light chain variable region without the CDR3 sequence (SEQ ID NO:15). The light chain variable region sequence without CDR3 is SEQ ID NO:36. In the bottom alignment, the second amino acid sequence (germline Homsap IGKV4-1*01 F) is SEQ ID NO:37. In the bottom alignment, the third sequence is the CDR3 of a P95C1 light chain variable region and is SEQ ID NO:15.

DETAILED DESCRIPTION

A. Definitions

Unless otherwise defined, all technical terms used herein have the same meaning as commonly understood by one of ordinary skill in the art to which this invention belongs.

An anti-LAM antibody may take one of numerous forms in the art, as disclosed herein. Antibodies are in part defined by the antigens to which they bind, thus, an "anti-LAM antibody" is any such antibody which specifically binds at least one epitope of lipoarabinomannan (LAM) as described herein. It is understood in the art that an antibody is a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CHi, CH2 and CH3). A light chain is comprised of a light chain variable region (VL) and a light chain constant region (CL). The variable regions of both the heavy and light chains comprise framework regions (FWR) and complementarity determining regions (CDR). The four FWR regions are relatively conserved while CDR regions (CDR1, CDR2 and CDR3) represent hypervariable regions and are arranged from NH2 terminus to the COOH terminus as follows: FWR1, CDR1, FWR2, CDR2, FWR3, CDR3, FWR4. The variable regions of the heavy and light chains contain a binding domain that interacts with an antigen while, depending of the isotype, the constant region(s) may mediate the binding of the immunoglobulin to host tissues or factors.

An anti-PIM6/LAM antibody may take one of numerous forms in the art, as disclosed herein. An "anti-PIM6/LAM antibody" is any such antibody which specifically binds at least one epitope that is shared by phosphatidylinositol mannoside 6 (PIM6) and LAM as described herein. A human mAb specific for an epitope shared by LAM and PIM6 described herein is P95C1 which binds specifically to at least one polymannose structure in PIM6 and in the PIM6 related mannan domain of LM and LAM. P95C1 binds to both LAM and PIM6 because it sees a common (shared) epitope, and is thus referred to herein as an "anti-PIM6/LAM antibody" or "anti-PIM6/LAM monoclonal antibody," "human anti-PIM6/LAM antibody" or "human anti-PIM6/LAM monoclonal antibody."

It is known in the art that it is possible to manipulate monoclonal and other antibodies and use techniques of recombinant DNA technology to produce other antibodies or chimeric molecules which retain the specificity of the original antibody. Such techniques may evolve introducing DNA encoding the immunoglobulin variable region, or CDRs, of an antibody to the constant regions, or constant regions plus framework regions, of a different immunoglobulin.

The term "antibody" (Ab) as used herein is used in the broadest sense and specifically may include any immunoglobulin, whether natural or partly or wholly synthetically produced, including but not limited to monoclonal antibodies, polyclonal antibodies, multispecific antibodies (for example, bispecific antibodies and polyreactive antibodies), and antibody fragments. Thus, the term "antibody" as used in any context within this specification is meant to include, but not be limited to, any specific binding member, immunoglobulin class and/or isotype (e.g., IgG1, IgG2a, IgG2b, IgG3, IgG4, IgM, IgA1, IgA2, IgD, and IgE) and biologically relevant fragment or specific binding member thereof, including but not limited to Fab, F(ab')$_2$, scFv (single chain or related entity) and (scFv)$_2$.

The term "antibody fragments" as used herein may include those antibody fragments obtained using techniques readily known and available to those of ordinary skill in the art, as reviewed herein. Therefore, the term "antibody" describes any polypeptide or protein comprising a portion of an intact antibody, such as the antigen binding or variable region of the intact antibody. These can be derived from natural sources, or they may be partly or wholly synthetically produced. Examples of antibody fragments include, but are not limited to, Fab, Fab', F(ab')2, and Fv fragments; diabodies, and linear antibodies. In particular, as used herein, "single-chain Fv" ("sFv" or "scFv") are antibody fragments that comprise the VH and VL antibody domains connected into a single polypeptide chain. The sFv polypeptide can further comprise, e.g., a linker such as a flexible polypeptide linker between the VH and VL domains that enables the scFv to form the desired structure for antigen binding.

The term "monoclonal antibody" or "mAb" as used herein may refer to an antibody obtained from a population of substantially homogeneous antibodies, i.e., the individual antibodies comprising the population are identical except for possible naturally occurring mutations that may be present in minor amounts.

The terms "variants," "derivatives," and/or "variants and/or derivatives" as used herein may refer to antibodies, antibody fragments, recombinant antibodies, whether derived from natural sources or partly or wholly synthetically produced, as well as proteins, protein fragments, and polypeptides, inasmuch as the foregoing compounds are either structurally similar, i.e. retain a degree of identity that is at least 50%, at least 55%, at least 60%, at least 65%, at least 70%, at least 80%, at least 85%, at least 95%, at least 96%, at least 97%, at least 98%, or at least 99%, or greater sequence identity with an original unmodified antibody, and/or, independent of structural identity, may be functionally similar to the original unmodified anti-LAM and anti-PIM6/LAM antibodies, that is, they retain the ability to specifically bind to at least one epitope of LAM or to the shared PIM6/LAM epitope, respectively. For example, such variants and/or derivatives may include anti-LAM or anti-PIM6/LAM antibodies with variant Fc domains, chimeric antibodies, fusion proteins, bispecific antibodies, or other recombinant antibodies. Such variants and/or derivative antibodies may, but not necessarily, possess greater binding specificity for one or more epitope(s) of LAM, or PIM6, and/or may be able to bind to additional LAM or PIM6 epitopes.

The term "biological sample" refers to a sample obtained from an organism (e.g., patient) or from components (e.g., cells) of an organism. The sample may be of any biological tissue, cell(s) or fluid. The sample may be a "clinical sample" which is a sample derived from a subject, such as a human patient. Such samples include, but are not limited to, saliva, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample." A biological sample may also include a substantially purified or isolated protein, membrane preparation, or cell culture.

The terms "effective amount" or "therapeutically effective amount" as used herein may refer to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

The term "antigen binding fragment" or "Fab" as used herein may refer to a region on an antibody that binds to antigens. One of ordinary skill in the art will understand that Fabs are comprised of one constant and one variable domain of each of the heavy and light chain of an antibody.

As used herein, the terms "specific binding," "selective binding," "selectively binds," and "specifically binds," may refer to antibody binding to an epitope on a predetermined antigen but not to other antigens. Typically, the antibody (i) binds with an equilibrium dissociation constant ($K_D$) of approximately less than $10^{-6}$ M, such as approximately less than $10^{-7}$ M, $10^{-8}$ M, $10^{-9}$ M or $10^{-10}$ M or even lower when determined by, e.g., surface plasmon resonance (SPR) technology in a BIACORE® 2000 surface plasmon resonance instrument using the predetermined antigen, e.g., a LAM epitope, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen.

The terms "conservative sequence modifications" or "conservative substitutions" as used herein may refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function using the functional assays described herein.

The term "identity" as used herein may refer to the existence of shared structure between two compositions. The term "identity" in the context of proteins may refer to the amount (e.g. expressed in a percentage) of overlap between two or more amino acid and/or peptide sequences. In the context of nucleic acids, the term may refer to the amount (e.g. expressed in a percentage) of overlap between two or more nucleic acid sequences. As used herein, the percent (%) identity between two sequences is equivalent to the percent identity between the two sequences. The percent identity between the two sequences is a function of the number of identical positions shared by the sequences (i.e., % identity=#of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm. Such identity is well-represented in the art via local alignment tools and/or algorithms, and may include pairwise alignment, multiple sequence alignment methods, structural alignment methods, and/or phylogenetic analysis methods. Specific examples include the following. The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. Additionally or alternatively, the protein sequences of the present invention can further be used as a query sequence to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

The terms "co-administration," "co-administered," and "in combination with" as used herein may refer to the administration of at least two agents or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

The term "carriers" as used herein may include pharmaceutically acceptable carriers, excipients, or stabilizers that are nontoxic to the cell or mammal being exposed thereto at the dosages and concentrations employed. Often the physiologically acceptable carrier is an aqueous Ph buffered solution. Examples of physiologically acceptable carriers include, but not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to, polyvinylpyrrolidone; amino acids such as, but not limited to, glycine, glutamine, asparagine, arginine or lysine; monosaccharides, disaccharides, and other carbohydrates including, but not limited to, glucose, mannose, or dextrins; chelating agents such as, but not limited to, EDTA; sugar alcohols such as, but not limited to, mannitol or sorbitol; salt-forming counterions such as, but not limited to, sodium; and/or nonionic surfactants such as, but not limited to, TWEEN; polyethylene glycol (PEG), and PLURONICS.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing as well as after their appearance. Thus, "treating" or "treatment" includes "preventing" or "prevention" of disease. The terms "prevent" or "preventing" refer to prophylactic and/or preventative measures, wherein the object is to prevent or slow down the targeted pathologic condition or disorder. For example, in the case of infection by a virulent strain of the *Mycobacterium tuberculosis*-complex, "preventing" or "preventing" may arise in a situation where a course of treatment is advanced in order to prevent or stall infection by a virulent strain of the *Mycobacterium tuberculosis*-complex, such as through vaccination or passive administration of a protective antibody. Such "preventing" or "prevention" also arise in the case of latent infection by *Mycobacterium tuberculosis*, in which the object would be to prevent active infection and/or clear a patient of said latent infection. In addition, "treating" or "treatment" does not require complete alleviation of signs or symptoms, does not require a cure, and specifically includes protocols that have only a marginal effect on the patient.

The terms "patient," "subject" and "individual" are used interchangeably herein and may refer to a biological system to which a treatment can be administered. A biological system can include, for example, an individual cell, a set of cells (e.g., a cell culture), an organ, a tissue, or a multicellular organism. A "patient," "subject" or "individual" can refer to a human patient, subject or individual or a non-human patient, subject or individual.

The term "epitope" as used herein may refer to the region of an antigen to which an antibody or T cell binds. An "antigen" refers to a substance that elicits an immunological reaction or binds to the products of that reaction.

As used herein, the term "vector" means a nucleic acid molecule capable of transporting another nucleic acid to which it has been linked. Vectors capable of directing the expression of genes to which they are operatively linked are referred to herein as "expression vectors."

As used herein, "protein" and "polypeptide" are used synonymously to mean any peptide-linked chain of amino acids, regardless of length or post-translational modification, e.g., glycosylation or phosphorylation.

The term "labeled," with regard to an antibody, nucleic acid, peptide, polypeptide, cell, or probe, is intended to encompass direct labeling of the antibody, nucleic acid, peptide, polypeptide, cell, or probe by coupling (i.e., physically linking) a detectable substance to the antibody, nucleic acid, peptide, polypeptide, cell, or probe.

The terms "purified" or "isolated" peptide, polypeptide, or protein refers to a peptide, polypeptide, or protein, as used herein, may refer to a peptide, polypeptide, or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein (e.g., anti-LAM antibodies) described in the invention can be produced by recombinant DNA techniques.

B. *Mycobacterium tuberculosis*

Tuberculosis (TB) remains one of the world's deadliest communicable diseases, currently infecting approximately one-third of the world's population. An estimated 9.0 million people developed TB in 2013, and an estimated 1.5 million people died from the disease. Although there currently are antibiotic treatments available, these require lengthy treatments, and are increasingly compromised by the development of multi-drug resistant (MDR-TB) strains, which currently are responsible for about 3.5% of recent infections. These strains are much harder to treat and have significantly poorer cure rates. Also spreading are extensively drug-resistant TB (XDR-TB) strains, which are even more expensive and difficult to treat than MDR-TB strains, and have now been reported in 100 countries around the world.

There is a long-established paradigm that immunity against TB relies solely on cellular defense mechanisms. However, studies in the HIV field highlight the remarkable ability of the human humoral immune system to generate diverse antibodies with remarkable neutralization breadth and potency, and the present invention highlights the ability of the humoral immune system to produce high affinity antibodies that recognize multiple LAM epitopes. This suggests that much of the past difficulty in demonstrating an important role for antibody-mediated protection against TB may be due to the limitations in the quality and source of the antibodies used in past studies, and that applying methods of the present invention to generate more highly evolved antibodies from chronically-infected human patients may illustrate the critical role of the humoral response in immunity to TB.

Some embodiments of the invention are directed to methods for the in vitro culture of memory B cells from infected humans and molecular cloning of the variable regions of IgG heavy (H) and light (L) chains from a single cell. These methods may be utilized to generate human monoclonal antibodies against the major surface antigen LAM. The present invention relates to such antibodies, and engineered derivatives of these antibodies, that possess unique epitope specificities and binding properties, and the immunodiagnostic and immunotherapeutic applications of these antibodies.

C. Lipoarabinomannan (LAM)

One prominent antigenic target of the antibodies of the present invention is the surface glycolipid, lipoarabinomannan (LAM), a major structural component of the cell wall of *Mycobacterium tuberculosis*-complex members. The present invention identifies a previously unappreciated heterogeneity in the antigenic structure of LAM and in the humoral immune response towards LAM in response to infection and immunization. The structure of LAM is detailed in Khoo et al., "Variation in Mannose-capped Terminal Arabinan Motifs of Lipoarabinomannan from Clinical Isolates of *Mycobacterium tuberculosis* and *Mycobacterium avium* Complex," Journal of Biological Chemistry Vol 276, No. 6, Feb. 9, 2001, incorporated by reference herein in its entirety. The structure of LAM is complex, exhibiting an overall tripartite structure with four distinct structural domains; a phosphatidylinositol lipid anchor (Mannonsyl-Phosphatidyl-myo-Inositol), an $\alpha(1\rightarrow6)$-linked D-mannan backbone with terminal $\alpha(1\rightarrow2)$-Manp-linked side chains, an D-arabinan chain containing multiple tetra-/hexa-arabinofuranoside branches, and various capping motifs. LAM consists of a heterogeneous population of molecules, which can be resolved into multiple isoforms that possess different biological properties. This heterogeneity is due to varying lengths of the mannan and arabino chains, different branching patterns, different numbers of such branches, and modification of the arabino-side chains by mannose capping, MTX addition and acylation by fatty acids, succinates and lactates.

Virulent strains of the *Mycobacterium tuberculosis*-complex are extensively capped with mono-, di-, and tri-$\alpha$ $(1\rightarrow2)$-D-Manp saccharide units, while fast growing non-pathogenic strains like *M. smegmatis* have uncapped ends or phosphatidyl-myo-inositol caps (PILAM). It has been estimated that 40-70% of the nonreducing termini of LAM from pathogenic strains of the *Mycobacterium tuberculosis*-complex are mannose-capped, and analysis of the relative abundance of the different cap motifs for the virulent MT103 clinical strain showed that the dimannosyl unit was the major structural motif (75-80%), while the mannosyl and the trimannosyl motifs were present at lower concentrations (10-13%). This extensive capping may present a unique marker to differentiate virulent strains of the *Mycobacterium tuberculosis*-complex from non-virulent/non-pathogenic strains, such as *M. smegmatis*, and may also provide potential antigenic targets for therapeutic use of the anti-LAM antibodies of the present invention. In addition, some of the terminal mannose sugars in ManLAM found in the strain *M. tuberculosis* are further modified by $\alpha(1\rightarrow4)$ addition of a unique structure, 5-deoxy-5-methyl-thio-pentofuranose (MTX), which affects the immunoreactivity towards different mAbs sensitive to capping motifs, such as A194-01 and P30B9; MTX addition increases reactivity with A194-01 and decreases reactivity towards P30B9. This substitution is present in low abundance, and may present a unique marker to identify *M. tuberculosis*, potentially even from other virulent members of the *Mycobacterium tuberculosis*-complex, such as from *M. bovis* and *M. africanum*, and may also provide a potential antigenic target for therapeutic use of the anti-LAM antibodies of the present invention.

Secreted forms of LAM are important targets for immunodiagnostic assays of infection by pathogenic members of the *M. tuberculosis*-complex. In addition, a considerable body of evidence indicates that LAM is an important mediator of a number of functions that promote productive infection and pathogenicity. LAM is involved in maintaining cell wall integrity and resistance to beta-lactam antibiotics. Reduced expression of LAM on the bacterial surface correlated with defective macrophage entry, inhibition of phagosome-lysosome fusion, attenuation in macrophages, and increased sensitivity to adaptive immunity, and the binding of terminal mannosyl units of ManLAM to the mannose receptor on the surface of macrophages has been described as a critical step in the uptake of mycobacteria into phagocytic cells. Without wishing to be bound by theory, it is believed that ManLAM interacts with the C-type lectins, such as dendritic cell-specific intercellular adhesion molecule-3 (ICAM-3) grabbing non-integrin (DC-SIGN) the macrophage mannose receptor (MMR) and Dectin-2 on dendritic cells. Once inside macrophages, LAM is believed to inhibit phagosome-lysosome fusion which would lead to the destruction of the bacteria, thereby allowing the bacteria to persist inside the macrophages.

LAM is also secreted from the surface of bacteria, and the extracellular LAM binds to dendritic cell-surface receptors, including DC-SIGN and Dectin-2. These interactions are believed to suppress dendritic cell function and interfere with the host immune system, contributing to immune evasion. Because LAM is in relatively large quantities during active infection, it can be detected in the blood and urine of infected patients, for example, by one or more anti-LAM antibodies of the present invention. These may be used, for example, in diagnostic kits and methods related to said diagnostic kits.

D. Anti-LAM and Anti-PIM6/LAM Antibodies

The anti-LAM antibodies of the present invention may comprise isolated, cultured, or engineered variants and/or derivatives of human monoclonal antibodies that recognize at least one epitope on lipoarabinomannan (LAM). An anti-PIM6/LAM antibody (e.g., P95C1) as described herein specifically binds at least one polymannose structure in PIM6 and in the PIM6 cross-reactive mannan domain of LAM. The anti-LAM and anti-PIM6/LAM antibodies of the present invention may be purified according to methods known in the art. Such methods may include, for example but not limited to, affinity chromatography, ion exchange chromatography, immobilized metal chelate chromatography, thiophilic adsorption, physiochemical fractionation, or other antigen-specific affinity methods, for example, methods including protein A, G, and L antibody-binding ligands. Such purified antibodies may or may not have structural characteristics that are different from human monoclonal antibodies that are not purified. For example, conformational epitope changes for human monoclonal antibodies may occur upon purification. Antibodies may be bound to additional molecules that are removed upon purification. Accordingly, such purified antibodies may or may not have different functional activity. The anti-LAM and anti-PIM6/LAM antibodies of the present invention may have a number of structural modifications. For example, the anti-LAM and anti-PIM6/LAM antibodies of the present invention may be glycosylated, PEGylated, or otherwise chemically modified in such a manner as to affect the stability, function, bioavailability, epitope recognition, or other functional activity. The anti-LAM and anti-PIM6/LAM antibodies of the present invention may be engineered variants and/or derivatives of those antibodies described below, and may or may not possess functional or structural equivalence. Accordingly, such variants and/or derivatives are still considered within the scope of the present invention, so long as they are derived or engineered at least in part from an isolated human monoclonal anti-LAM or anti-PIM6/LAM antibody, and/or recognize at least one epitope on LAM.

1. A194-01

Figure 1A:
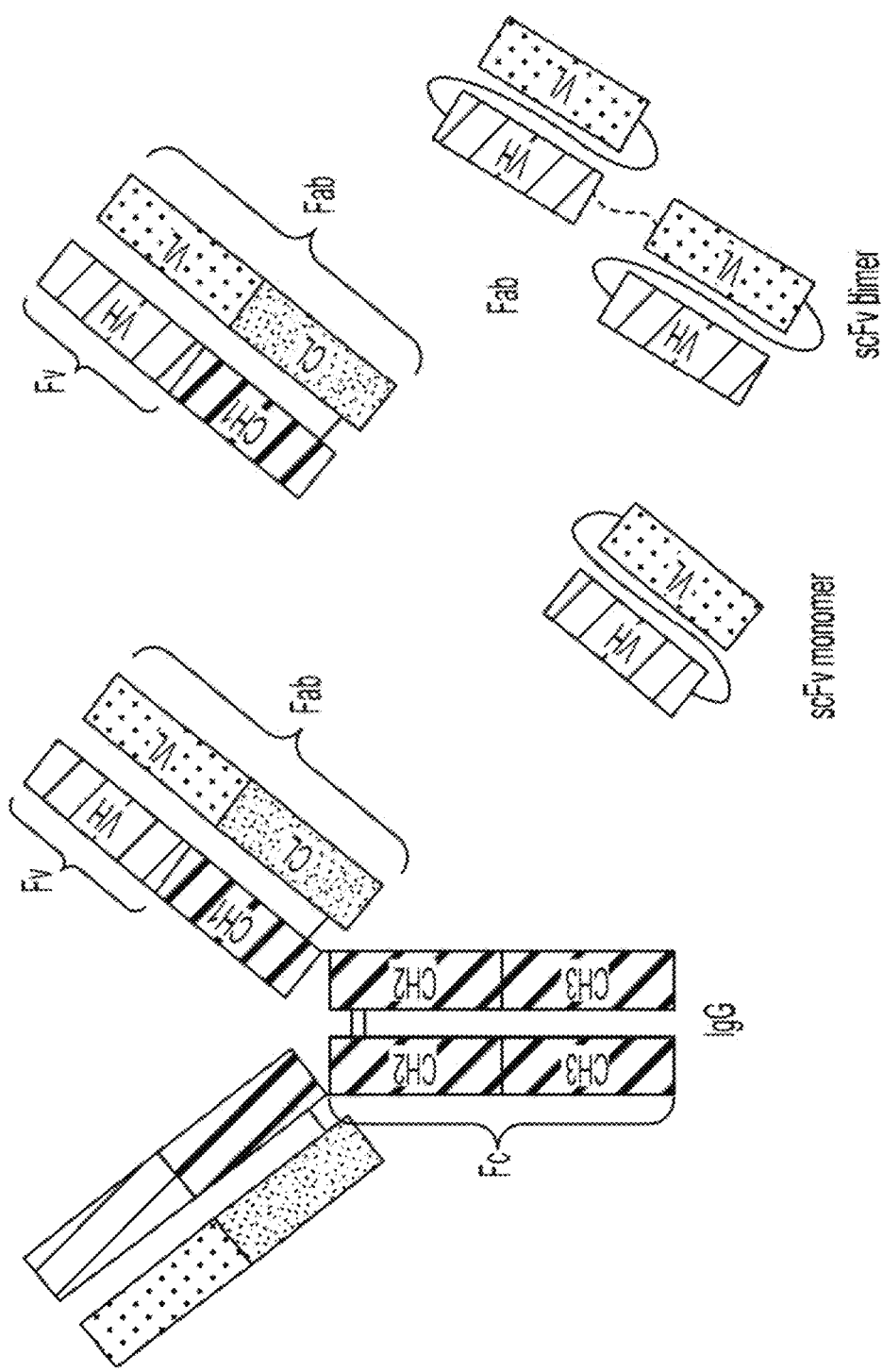
FIG. 1A—Model of IgG form of A194-01 and fragments thereof used in binding competition assays. These included monovalent scFv and Fab structures, and divalent scFv dimer and natural IgG.
Figure 1B:
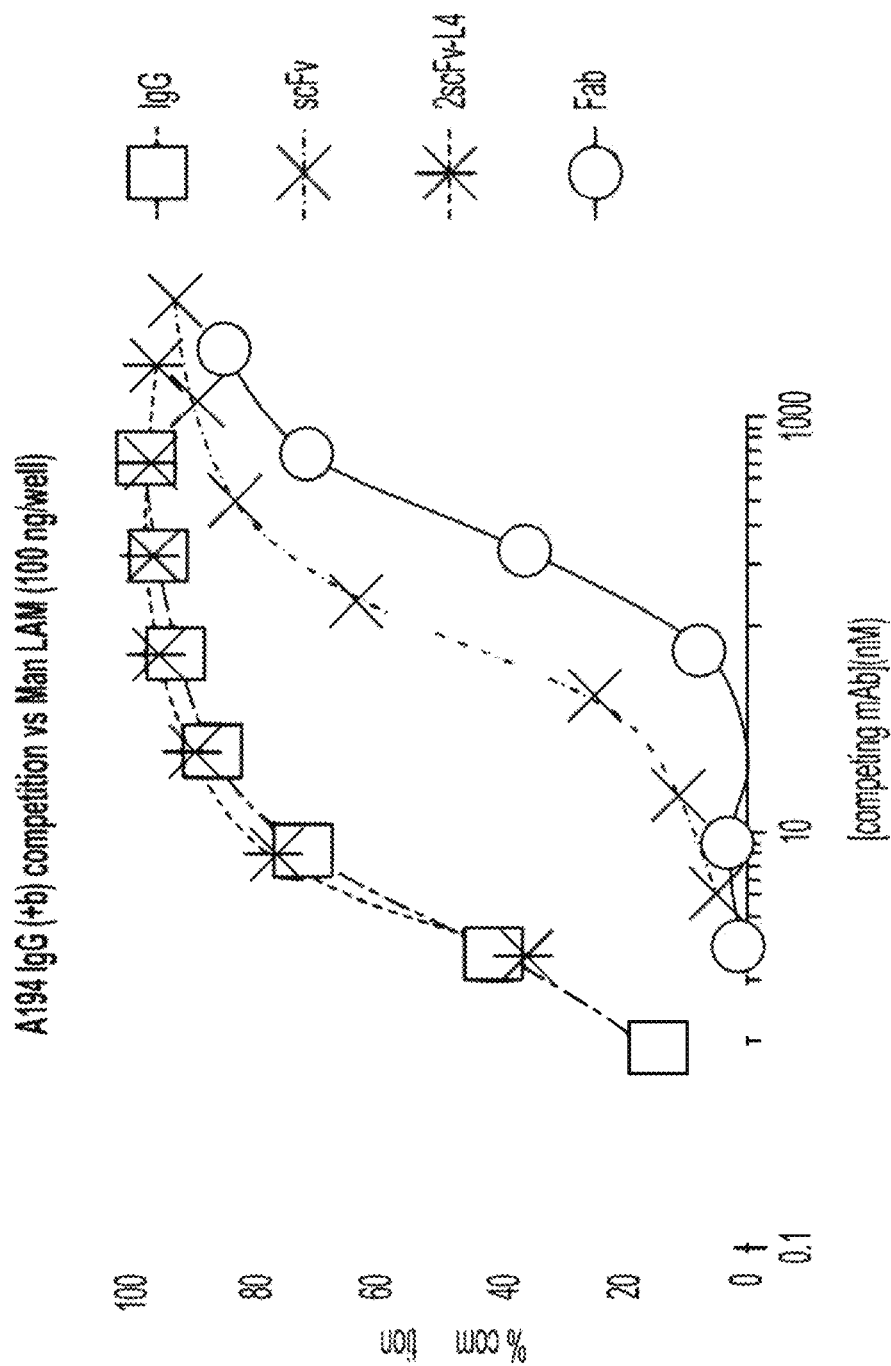
FIG. 1*i*—Competition curves showing that the monovalent forms of A194-01 competed less effectively than the divalent forms.
FIG. 1C—Structure of higher-valent form of A194-01. This represents a homologous tetravalent A194-01 scFv-IgG, which contains an A194-01 scFv domain joined to the N-terminus of each of the normal heavy chains.
FIG. 4B-1-4B-2—Binding profiles for six LAM-specific monoclonal antibodies against panel of 25 synthetic oligosaccharides. Binding results are shown for three concentrations, and the relative affinities of the antibodies to these antigens is indicated by the titration pattern.

In some embodiments, the present invention is directed to the human monoclonal antibody A194-01 including variants and/or derivatives thereof. A194-01 is specific for LAM. A194-01 possesses very high binding activity for LAM, for example, the IgG isotype of A194-01 may exhibit 50% maximal binding activity of the antibody at a concentration of approximately 20 ng/ml, thus signifying a high affinity for LAM. A194-01 was originally isolated and purified as an IgG, however, A194-01 may exist in a number of isotypes, as well as engineered and recombinant isotypes, including but not limited to IgG, IgA, IgM, monovalent single chain Fv (scFv) fragments, Fab proteins, divalent scFv fragments, single chain scFv fragments (monomers) wherein individual variable light and variable heavy regions are joined by e.g. a flexible linker, and dimeric scFv proteins in which two scFv monomers are joined to one another (FIG. 1A) Some particular engineered variants and/or derivatives of A194-01 include, but are not limited to the following. One engineered variant and/or derivative of A194-01 comprises a tetravalent scFv-IgG, formed by joining the A194-01 scFv antigen to the N-terminus of A194-01 IgG (FIG. 1B, FIG. 17A-17C), which may increase binding affinity and broaden the range of epitopes recognized (examples of this are given in FIGS. 14 and 15). The tetravalent scFv-IgG may comprise leader-VH-VL-IgG, or may comprise leader-VL-VH-IgG. One having ordinary skill in the art will appreciate that engineered scFv-IgG variants and/or derivatives may have valences beyond just tetravalent. Another engineered variant and/or derivative of A194-01 comprises a pentavalent IgM, generated by converting a dimeric A194-01 IgG to a human IgM contain domain, wherein such pentavalent IgM contains 10 binding sites (FIG. 1B). One of ordinary skill in the art will appreciate that further combinations of A194-01 antigenic fragments are possible and are considered within the scope of this invention, particularly those antibody fragments that display complementarity determining regions (CDRs) specific to A194-01.

The IgG isotype of A194-01 recognizes a unique and complex epitope that is expressed on unmodified Ara4 and Ara6 side-chains and on side-chains bearing a single mannose. Although A194-01 does not recognize side chains bearing di- or tri-mannose substitutions, it does react with such structures if they are further modified with an MSX substituent. Accordingly, the IgG isotype of A194-01 binds to PTLAM and ManLAM with high affinity, and also binds strongly with uncapped versions of both Ara4 and Ara6 structures, and binds somewhat less strongly to single mannose-capped and MSX-substituted Ara4/Ara6 structures, but poorly if at all to di-substituted and tri-substituted ManLAM (FIG. 4A-1-4A-4, FIG. 4B-1-4B-2). Without wishing to be bound by theory, the dramatically different effect of attachment of mannose versus MSX to the terminal mannose of the mono-mannosylated Ara4 structure may reflect a difference between the α(1→2) linkage of the mannose and α(1→4) linkage of the MSX substitution. Engineered variants and/or derivatives of A194-01, including those that possess higher valencies, may exhibit broader epitope specificity than the A194-01 IgG isotype (FIG. 14), and may further exhibit enhanced affinity for LAM (FIG. 15). For example, the tetravalent scFv-IgG engineered A194-01 and the engineered IgA and IgM isotypes bind to both Ara4 and Ara6 structures with higher affinity than the A194-01 IgG isotype, and furthermore, also recognize di-mannose and tri-mannose capped structures that the IgG isotype binds to poorly (FIG. 14). Because pathogenic species of the *Mycobacterium tuberculosis*-complex predominantly exhibit di-mannose capped structures, these engineered variants and/or derivatives of A194-01, including scFv-IgG and IgM isotypes, may prove particularly useful for diagnostic kits and methods, as well as for therapeutic use.

Further engineered variants and/or derivatives of A194-01 include those antibodies wherein the IgG1 Fc domain is converted to IgG3, which is more opsogenic, or by generating multimeric versions, by substituting the IgG1 constant domain by dimeric IgA or pentameric or hexameric IgM. Without wishing to be bound by theory, this may significantly enhance avidity of the anti-LAM antibodies by increasing the flexibility and range of bivalent and multivalent binding, which contributes to affinity (FIG. 1A-1C). This is of potential clinical significance, as treatments would be particularly valuable in cases of exposure or infection with MDR or x-MDR strains of Myocbacterium tuberculosis, which cannot be effectively treated with traditional antibiotics.

TABLE 1

A194-01 Complementarity Determining Regions (CDR)

Light Chain

CDR1 - RSIRSA (SEQ ID NO: 1)
CDR2 - GAS (SEQ ID NO: 2)
CDR3 - QQYDFWYTF (SEQ ID NO: 3)

Heavy Chain

CDR1 - GFNFEDFG (SEQ ID NO: 4)
CDR2 - ISWNGANI (SEQ ID NO: 5)
CDR3 - IDWYRDDYYKMDV (SEQ ID NO: 6)

One of ordinary skill in the art will appreciate that CDRs are crucial to the diversity of antigen specificities. One having ordinary skill in the art will further appreciate that CDR3 is the most variable of CDR regions, and as such bears the greatest importance, with diversity in the CDR3 region of the variable heavy chain being sufficient for most antibody specificities.

Accordingly, in some embodiments, the anti-LAM antibodies have a CDR1, CDR2, and CDR3 region of the variable light chain as set forth in SEQ ID NOS: 1, 2 and 3, respectively. In some embodiments, the anti-LAM antibodies have a CDR1, CDR2, and CDR3 region of the variable light chain as set forth in SEQ ID NOS: 1, 2, and 3 respectively with conservative sequence modifications. In some embodiments, the anti-LAM antibodies have a CDR1, CDR2, and CDR3 region of the variable light chain having up to 95% identity with SEQ ID NOS: 1, 2, and 3 respectively. In other embodiments, the anti-LAM antibodies have a CDR1, CDR2, and CDR3 region of the variable light chain having up to 90% identity with SEQ ID NOS: 1, 2, and 3 respectively. In other embodiments, the anti-LAM antibodies have a CDR1, CDR2, and CDR3 region of the variable light chain having up to 85% identity with SEQ ID NOS: 1, 2, and 3 respectively. In other embodiments, the anti-LAM antibodies have a CDR1, CDR2, and CDR3 region of the variable light chain having up to 80% identity with SEQ ID NOS: 1, 2, and 3 respectively. In some embodiments, the anti-LAM antibodies have a CDR3 region of the variable light chain as set forth in SEQ ID NO: 3. In some embodiments, the anti-LAM antibodies have a CDR3 region of the variable light chain as set forth in SEQ ID NO: 3 with conservative sequence modifications. In other embodiments, the anti-LAM antibodies have a CDR3 region of the variable light chain having up to 95% identity with SEQ ID NO: 3. In other embodiments, the anti-LAM antibodies have a CDR3 region of the variable light chain having up to 90% identity with SEQ ID NO: 3. In other embodiments, the anti-LAM antibodies have a CDR3 region of the variable light chain having up to 85% identity with SEQ ID NO: 3. In other embodiments, the anti-LAM antibodies have a CDR3 region of the variable light chain having up to 80% identity with SEQ ID NO: 3.

In some embodiments, the anti-LAM antibodies have a CDR1, CDR2, and CDR3 region of the variable heavy chain as set forth in SEQ ID NOS: 4, 5 and 6, respectively. In some embodiments, the anti-LAM antibodies have a CDR1, CDR2, and CDR3 region of the variable heavy chain as set forth in SEQ ID NOS: 4, 5 and 6, respectively with conservative sequence modifications. In some embodiments, the anti-LAM antibodies have a CDR1, CDR2, and CDR3 region of the variable heavy chain having up to 95% identity with SEQ ID NOS: 4, 5, and 6 respectively. In other embodiments, the anti-LAM antibodies have a CDR1, CDR2, and CDR3 region of the variable heavy chain having up to 90% identity with SEQ ID NOS: 4, 5, and 6 respectively. In other embodiments, the anti-LAM antibodies have a CDR1, CDR2, and CDR3 region of the variable heavy chain having up to 85% identity with SEQ ID NOS: 4, 5, and 6 respectively. In other embodiments, the anti-LAM antibodies have a CDR1, CDR2, and CDR3 region of the variable heavy chain having up to 80% identity with SEQ ID NOS: 4, 5, and 6 respectively. In some embodiments, the anti-LAM antibodies have a CDR3 region of the variable heavy chain as set forth in SEQ ID NO: 6. In some embodiments, the anti-LAM antibodies have a CDR3 region of the variable heavy chain as set forth in SEQ ID NO: 6 with conservative sequence modifications. In other embodiments, the anti-LAM antibodies have a CDR3 region of the variable heavy chain having up to 95% identity with SEQ ID NO: 6. In other embodiments, the anti-LAM antibodies have a CDR3 region of the variable heavy chain having up to 90% identity with SEQ ID NO: 6. In other embodiments, the anti-LAM antibodies have a CDR3 region of the variable heavy chain having up to 85% identity with SEQ ID NO: 6. In other embodiments, the anti-LAM antibodies have a CDR3 region of the variable heavy chain having up to 80% identity with SEQ ID NO: 6.

In the experiments described herein, the A194-01 antibody was expressed by transfection of H and L chain vectors in Expi293 cells and cultured in standard Expi293 serum-free medium for several days. The secreted antibody was purified from the culture supernatant by affinity chromatography on columns conjugated with Protein A or Protein G ligands. The bound antibodies were released from the ligands by treatment with low PH buffer (0.2 M glcine-HCl, PH 2.5) and neutralized with ⅟₅₀ volume of 2 M tris buffer buffer (PH 8.8). The buffer was exchanged with PBS by dialysis or by several rounds of concentration on centrifugal filters (Amicon Ultra centrifugal filters, 30K mw limit).

The amino acid (aa) and nucleic acid (nt) sequences for A194 heavy and light chain sequences are as follows:

A194 Heavy chain nt sequence:
(SEQ ID NO: 39)
```
CAAGTGCAGCTGTTGGAGTCTGGGGGAGGTGTGGTACGGCCGGGGGGGT
CCCTGAGACTCTCCTGTGCAGCCTCTGGATTCAACTTTGAAGATTTTGG
CATGAGCTGGGTCCGCCAAGCTCCAGGGAAGGGGCTGGAGTGGGTCTCT
AGTATTAGTTGGAATGGTGCTAATATAGGCTATGTAGACTCTGTGAAGG
GCCGATTCACCATCTCCAGAGACAACGCCAAGAACTCCCTATATCTGCA
AATGAACAGTCTGAGAGCCGAGGACACGGCCTTATATTACTGTGCGATA
GACTGGTACAGAGACGACTACTACAAGATGGACGTCTGGGGCAAAGGGA
CCACGGTCACCGTCTCCTCAGCCTCGACCAAGGGCCCATCGGTCTTCCC
GCTAGCGCCCTCCTCCAAGAGCACCTCTGGGGGCACAGCGGCCCTGGGC
TGCCTGGTCAAGGACTACTTCCCCGAACCTGTGACGGTCTCGTGGAACT
CAGGCGCCCTGACCAGCGGCGTGCACACCTTCCCGGCTGTCCTACAGTC
CTCAGGACTCTACTCCCTCAGCAGCGTGGTGACCGTGCCCTCCAGCAGC
TTGGGCACCCAGACCTACATCTGCAACGTGAATCACAAGCCCAGCAACA
CCAAGGTGGACAAGAAAGTTGAGCCCAAATCTTGTGACAAAACTCACAC
ATGCCCACCGTGCCCAGCACCTGAACTCCTGGGGGGACCGTCAGTCTTC
CTCTTCCCCCCAAAACCCAAGGACACCCTCATGATCTCCCGGACCCCTG
AGGTCACATGCGTGGTGGTGGACGTGAGCCACGAAGACCCTGAGGTCAA
GTTCAACTGGTACGTGGACGGCGTGGAGGTGCATAATGCCAAGACAAAG
CCGCGGGAGGAGCAGTACAACAGCACGTACCGTGTGGTCAGCGTCCTCA
CCGTCCTGCACCAGGACTGGCTGAATGGCAAGGAGTACAAGTGCAAGGT
CTCCAACAAAGCCCTCCCAGCCCCCATCGAGAAAACCATCTCCAAAGCC
AAAGGGCAGCCCCGAGAACCACAGGTGTACACCCTGCCCCCATCCCGGG
ATGAGCTGACCAAGAACCAGGTCAGCCTGACCTGCCTGGTCAAAGGCTT
CTATCCCAGCGACATCGCCGTGGAGTGGGAGAGCAATGGGCAGCCGGAG
AACAACTACAAGACCACGCCTCCCGTGCTGGACTCCGACGGCTCCTTCT
TCCTCTACAGCAAGCTCACCGTGGACAAGAGCAGGTGGCAGCAGGGGAA
CGTCTTCTCATGCTCCGTGATGCATGAGGCTCTGCACAACCACTACACG
CAGAAGAGCCTCTCCCTGTCTCCGGGTAAATGA
```

A194 Heavy chain aa sequence:
(SEQ ID NO: 40)
```
QVQLLESGGGVVRPGGSLRLSCAASGFNFEDFGMSWVRQAPGKGLEWVS
SISWNGANIGYVDSVKGRFTISRDNAKNSLYLQMNSLRAEDTALYYCAI
DWYRDDYYKMDVWGKGTTVTVSSASTKGPSVFPLAPSSKSTSGGTAALG
CLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYT
QKSLSLSPGK*
```

A194 Light chain nt sequence (kappa):
(SEQ ID NO: 41)
```
GAAATAGTGATGACGCAGTCTCCAGCCACCCTGTCTGTCTCTCCAGGGG
AAAGAGCCACCCTCTCCTGCAGGGCCAGTCGGAGTATTCGCAGCGCCTT
AGCCTGGTACCAGCACAAACCTGGCCAGGCTCCCAGGCTCCTCATCTTT
GGTGCATCCACCAGGGCCACTGGTATCCCAGCCAGGTTCAGTGGCAGTG
GGTCTGGGACAGACTTCACTCTCACCGTCAGCAGCATACGGTCTGAGGA
TTCTGCAGTTTATTACTGTCAGCAGTATGATTTCTGGTACACTTTTGGC
CAGGGGACCAAGCTGGAGATCAAACGAACTGTGGCTGCACCATCTGTCT
TCATCTTCCCGCCATCTGATGAGCAGTTGAAATCTGGAACTGCCTCTGT
TGTGTGCCTGCTGAATAACTTCTATCCCAGAGAGGCCAAAGTACAGTGG
AAGGTGGACAACGCCCTCCAATCGGGTAACTCCCAGGAGAGTGTCACAG
AGCAGGACAGCAAGGACAGCACCTACAGCCTCAGCAGCACCCTGACGCT
GAGCAAAGCAGACTACGAGAAACACAAAGTCTACGCCTGCGAAGTCACC
CATCAGGGCCTGAGCTCGCCCGTCACAAAGAGCTTCAACAGGGGAGAGT
GTTAG
```

A194 Light chain aa sequence (kappa):
(SEQ ID NO: 42)
```
EIVMTQSPATLSVSPGERATLSCRASRSIRSALAWYQHKPGQAPRLLIF
GASTRATGIPARFSGSGSGTDFTLTVSSIRSEDSAVYYCQQYDFWYTFG
QGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC*
```

2. P30B9

In some embodiments, the present invention is directed to the recombinant human monoclonal antibody P30B9 including variants and/or derivatives thereof. P30B9 is specific for LAM. P30B9 was originally isolated and purified as an IgM, however, P30B9 may exist in a number of isotypes, as well as engineered and recombinant isotypes, including but not limited to IgM, IgG, IgA, as well as antigenic fragments thereof, including but not limited to monovalent single chain Fv (scFv) fragments, Fab proteins, divalent scFv fragments, single chain scFv fragments (monomers) wherein individual variable light and variable heavy regions are joined by e.g. a flexible linker, and dimeric scFv proteins in which two scFv monomers are joined to one another.

The IgM isotype of P30B9 binds most potently to di-mannose substituted Ara4 and Ara6 LAM epitopes with the Manp-α(1→2)-Manp-(1→5)-Araf structures (FIGS. 4, 16 and 18) although other Manp-α substituted structures (e.g., structure 2, 4 and 59 in FIG. 8A-8B-1-8B-3) may also be recognized with lower affinities. The preferential recognition of P30B9 for di-mannose capped LAM has potential clinical relevance, since di-mannose caps are reported to be the dominant LAM modification on virulent strains of the *Mycobacterium tuberculosis*-complex. Without wishing to be bound by theory, it is believed that terminal mannosyl units mediate binding of LAM from virulent strains of the *Mycobacterium tuberculosis*-complex to human macrophage and other immune cells that leads to the perturbation of immune function and establishment of stable infection. Without wishing to be bound by theory, binding of the mannose caps to the mannose receptor is believed to limit phagosome-lysosome (P-L) fusion and facilitate survival of the bacterium in infected macrophages. The specificity of P30B9 for di-mannose capped LAM is indicated by the specificity of this mAb for glycoconjugates bearing this structure, and in the fact that the IgM isotype of P30B9 binds specifically to LAM derived from either *Mycobacterium tuberculosis*, but not to LAM from *Mycobacterium smegmatis* or *Mycobacterium leprae*, which do not contain di-mannose capped LAM epitopes. This is in contrast to the IgG isotype of A194-01, which binds to PILAM, uncapped Ara4/Ara6 residues, and mono-mannose capped LAM epitopes, all of which are common in *Mycobacterium smegmatis* and *Mycobacterium leprae*. Like the IgM isotype of P30B9, the IgM isotype of A194-01 is able to bind to di-mannose and tri-mannose capped LAM epitopes (FIG. 14), presumable due to an increased binding avidity.

Therefore, the IgM isotypes of P30B9 may serve as an important immunodiagnostic reagent for detecting infection by virulent members of the *Mycobacterium tuberculosis*-complex and distinguishing said virulent members other nonpathogenic mycobacterial species, as it is specific to di-mannose capped LAM. Furthermore, the IgM isotype of the P30B9 antibody as well as engineered variants and/or derivatives of A194-01 may possess immunotherapeutic activity that limit infection and pathogenesis of virulent members of the *Mycobacterium tuberculosis*-complex and may be suitable for use in therapy, either in combination with traditional antibiotics, additional antibodies, or alone, or may be used as a passive immunotherapeutic agent. The IgM isotype of P30B9 binds specifically to ManLAM derived from *Mycobacterium tuberculosis* with high affinity (FIG. 2A,B), but not to PILAM derived from *Mycobacterium smegmatis* (FIG. 2C).

Engineered variants and/or derivatives of P30B9 may include, for example, P30B9 expressed in the IgA isotype, including dimeric IgA1 and IgA2. Without wishing to be bound by theory, it is believed that polyvalency is required for P30B9 function, as this antibody was isolated as an IgM, and is not active when expressed as an IgG. The present invention shows that P30B9 is active in engineered IgA isotypes, including dimeric IgA1 and IgA2. This was tested by moving the P30B9 VH domain into IgA1 and IgA2 vectors. IgA1 differs from IgA2 mostly by the presence of a 16 amino-acid insertion, comprised of a repeat of 8 amino acids rich in proline, serine, and threonine, and modified with 3-6, O-linked oligosaccharides [FIG. 5A-5C-2]. The binding activity of the engineered IgA forms of P30B9 to ManLAM were compared to those of the IgG and IgM forms. The IgM form had the highest activity, while both of the IgA forms were also able to bind to ManLAM, with the IgA2 form showing weaker activity than the IgA1 form, and the IgG form was inactive in an ELISA against ManLAM (FIG. 6).

TABLE 2

P30B9 Complementarity Determining Regions (CDR)

Light Chain

CDR1 - QSINSN (SEQ ID NO: 7)
CDR2 - KAS (SEQ ID NO: 8)
CDR3 - QQYKAFKTF (SEQ ID NO: 9)

Heavy Chain

CDR1 - GGSFSGYY (SEQ ID NO: 10)
CDR2 - FDLGGSITHSRGT (SEQ ID NO: 11)
CDR3 - RGLAMGGTKEFDS (SEQ ID NO: 12)

One of ordinary skill in the art will appreciate that CDRs are crucial to the diversity of antigen specificities. One having ordinary skill in the art will further appreciate that CDR3 is the most variable of CDR regions, and as such bears the greatest importance, with diversity in the CDR3 region of the variable heavy chain being sufficient for most antibody specificities. Accordingly, in some embodiments, the anti-LAM antibodies have a CDR1, CDR2, and CDR3 region of the variable light chain as set forth in SEQ ID NOS: 7, 8 and 9, respectively. In some embodiments, the anti-LAM antibodies have a CDR1, CDR2, and CDR3 region of the variable light chain as set forth in SEQ ID NOS: 7, 8 and 9, respectively with conservative sequence modifications. In some embodiments, the anti-LAM antibodies have a CDR1, CDR2, and CDR3 region of the variable light chain having up to 95% identity with SEQ ID NOS: 7, 8, and 9 respectively. In other embodiments, the anti-LAM antibodies have a CDR1, CDR2, and CDR3 region of the variable light chain having up to 90% identity with SEQ ID NOS: 7, 8, and 9 respectively. In other embodiments, the anti-LAM antibodies have a CDR1, CDR2, and CDR3 region of the variable light chain having up to 85% identity with SEQ ID NOS: 7, 8, and 9 respectively. In other embodiments, the anti-LAM antibodies have a CDR1, CDR2, and CDR3 region of the variable light chain having up to 80% identity with SEQ ID NOS: 7, 8, and 9 respectively. In some embodiments, the anti-LAM antibodies have a CDR3 region of the variable light chain as set forth in SEQ ID NO: 9. In some embodiments, the anti-LAM antibodies have a CDR3 region of the variable light chain as set forth in SEQ ID NO: 9 with conservative sequence modifications. In other embodiments, the anti-LAM antibodies have a CDR3 region of the variable light chain having up to 95% identity with SEQ ID NO: 9. In other embodiments, the anti-LAM antibodies have a CDR3 region of the variable light chain having up to 90% identity with SEQ ID NO: 9. In other embodiments, the anti-LAM antibodies have a CDR3 region of the variable light chain having up to 85% identity with SEQ ID NO: 9. In other embodiments, the anti-LAM antibodies have a CDR3 region of the variable light chain having up to 80% identity with SEQ ID NO: 9.

In some embodiments, the anti-LAM antibodies have a CDR1, CDR2, and CDR3 region of the variable heavy chain as set forth in SEQ ID NOS: 10, 11 and 12, respectively. In some embodiments, the anti-LAM antibodies have a CDR1, CDR2, and CDR3 region of the variable heavy chain as set forth in SEQ ID NOS: 10, 11 and 12, respectively with conservative sequence modifications. In some embodiments, the anti-LAM antibodies have a CDR1, CDR2, and CDR3 region of the variable heavy chain having up to 95% identity with SEQ ID NOS: 10, 11 and 12, respectively. In other embodiments, the anti-LAM antibodies have a CDR1, CDR2, and CDR3 region of the variable heavy chain having up to 90% identity with SEQ ID NOS: 10, 11 and 12, respectively. In other embodiments, the anti-LAM antibodies have a CDR1, CDR2, and CDR3 region of the variable heavy chain having up to 85% identity with SEQ ID NOS: 10, 11 and 12, respectively. In other embodiments, the anti-LAM antibodies have a CDR1, CDR2, and CDR3 region of the variable heavy chain having up to 80% identity with SEQ ID NOS: 10, 11 and 12, respectively. In some embodiments, the anti-LAM antibodies have a CDR3 region of the variable heavy chain as set forth in SEQ ID NO: 12. In some embodiments, the anti-LAM antibodies have a CDR3 region of the variable heavy chain as set forth in SEQ ID NO: 12 with conservative sequence modifications. In other embodiments, the anti-LAM antibodies have a CDR3 region of the variable heavy chain having up to 95% identity with SEQ ID NO: 12. In other embodiments, the anti-LAM antibodies have a CDR3 region of the variable heavy chain having up to 90% identity with SEQ ID NO: 12. In other embodiments, the anti-LAM antibodies have a CDR3 region of the variable heavy chain having up to 85% identity with SEQ ID NO: 12. In other embodiments, the anti-LAM antibodies have a CDR3 region of the variable heavy chain having up to 80% identity with SEQ ID NO: 12.

In the experiments described herein, the P30B9 antibody was expressed by transfection of H and L chain vectors in Expi293 cells and cultured in standard Expi293 serum-free medium for several days. The secreted antibody was purified from the culture supernatant by affinity chromatography on columns conjugated with Protein L ligand. The bound antibody was released from the ligands by treatment with low PH buffer (0.2 M glcine-HCl, PH 2.5) and neutralized with ⅟₅₀ volume of 2 M tris buffer buffer (PH 8.8). The buffer was exchanged with PBS by dialysis or by several rounds of concentration on centrifugal filters (Amicon Ultra centrifugal filters, 30K mw limit).

The amino acid sequences for P30B9 heavy chain and light chain and their comparison with its closest germline are shown in FIG. 22. The amino acid and nucleotide sequences for P30B9 including the CDR3 region are copied below:

```
P30B9-Heavy chain variable region:
                                     (SEQ ID NO: 43)
QVQLQQWGAGLLKPSETLSLTCAVY
GGSFSGYY WSWIRQSPETGLEWLGE FDLGGS ITHSRGT
NYNPSLKSRVTISGDTSKNQFSLKLTSVTAADTAVYYC
ARGLAMGGTKEFDS P30B9-Light chain variable region:
                                     (SEQ ID NO: 44)
DIQMTQSPDSLSASVGDRITITCRAS QSINSN
LAWYQQKPGKAPKLLIY KAS
DLESGVPSRFSGSGSGTEFTLTISSLQPDDFATYYC
QQYKAFKT
```

```
P30B9-Heavy chain DNA sequence:
                                     (SEQ ID NO: 45)
caggtgcagctacagcagtggggcgcaggactgttgaagccttcggaga
ccctgtccctcacctgcgctgtctatggtgggtccttcagtggttacta
ctggagctggatccgccagtccccagagacggggctggagtggcttggc
gaaTTCGATCTTGGTGGAAGCatcactcatagtagaggcaccaactaca
acccgtcgctcaagagtcgagtcaccatctcaggagacacgtccaagaa
ccagttctccctgaaactgacctctgtgaccgccgcggacacggctgtc
tattactgtgcgagaggtttagcaatgggtggaactaaggagtttgact
cctggggccagggaaccctggtcaccgtctcctcag P30B9-Light chain:
                                     (SEQ ID NO: 46)
gacatccagatgacccagtctccagactccctgtctgcatctgtaggag
acagaatcaccatcacttgccgggccagtcagagtattaatagtaattt
ggcctggtatcagcagaaaccggggaaagcccctaagctcctgatctat
aaggcgtctgatttagaaagtggggtcccatcaaggttcagcggcagtg
gatctgggacagaattcactctcaccatcagcagcctgcagcctgatga
ttttgcaacttattattgccaacagtataaagcattcaagacgttcggc
cacgggaccaaggtggaaatcaaac
```

3. P95C1

In some embodiments, the present invention is directed to the recombinant human monoclonal antibody P95C1 including variants and/or derivatives thereof. P95C1 is specific for an epitope shared by LAM, LM and PIM6. Although P95C1 was originally isolated and purified as an IgM, P95C1 is also active when expressed in other isotypes, including but not limited to IgG and IgA forms.

One of ordinary skill in the art will appreciate that CDRs are crucial to the diversity of antigen specificities. One having ordinary skill in the art will further appreciate that CDR3 is the most variable of CDR regions, and as such bears the greatest importance, with diversity in the CDR3 region of the variable heavy chain being sufficient for most antibody specificities. Accordingly, in some embodiments, the anti-LAM antibodies have a CDR1, CDR2, and CDR3 region of the variable light chain as set forth in SEQ ID NOS: 13, 14 and 15, respectively. In some embodiments, the anti-LAM antibodies have a CDR1, CDR2, and CDR3 region of the variable light chain as set forth in SEQ ID NOS: 13, 14 and 15, respectively with conservative sequence modifications. In some embodiments, the anti-LAM antibodies have a CDR1, CDR2, and CDR3 region of the variable light chain having up to 95% identity with SEQ ID NOS: 13, 14 and 15, respectively. In other embodiments, the anti-LAM antibodies have a CDR1, CDR2, and CDR3 region of the variable light chain having up to 90% identity with SEQ ID NOS: 13, 14 and 15, respectively. In other embodiments, the anti-LAM antibodies have a CDR1, CDR2, and CDR3 region of the variable light chain having up to 85% identity with SEQ ID NOS: 13, 14 and 15, respectively. In other embodiments, the anti-LAM antibodies have a CDR1, CDR2, and CDR3 region of the variable light chain having up to 80% identity with SEQ ID NOS: 13, 14 and 15, respectively. In some embodiments, the anti-LAM antibodies have a CDR3 region of the variable light chain as set forth in SEQ ID NO: 15. In some embodiments, the anti-LAM antibodies have a CDR3 region of the variable light chain as set forth in SEQ ID NO: 15 with conservative sequence modifications. In other embodiments, the anti-LAM antibodies have a CDR3 region of the variable light chain having up to 95% identity with SEQ ID NO: 15. In other embodiments, the anti-LAM antibodies have a CDR3 region of the variable light chain having up to 90% identity with SEQ ID NO: 15. In other embodiments, the anti-LAM antibodies have a CDR3 region of the variable light chain having up to 85% identity with SEQ ID NO: 15. In other embodiments, the anti-LAM antibodies have a CDR3 region of the variable light chain having up to 80% identity with SEQ ID NO: 15.

In some embodiments, the anti-LAM antibodies have a CDR1, CDR2, and CDR3 region of the variable heavy chain as set forth in SEQ ID NOS: 16, 17 and 18, respectively. In some embodiments, the anti-LAM antibodies have a CDR1, CDR2, and CDR3 region of the variable heavy chain as set forth in SEQ ID NOS: 16, 17 and 18, respectively with conservative sequence modifications. In some embodiments, the anti-LAM antibodies have a CDR1, CDR2, and CDR3 region of the variable heavy chain having up to 95% identity with SEQ ID NOS: 16, 17 and 18, respectively. In other embodiments, the anti-LAM antibodies have a CDR1, CDR2, and CDR3 region of the variable heavy chain having up to 90% identity with SEQ ID NOS: 16, 17 and 18, respectively. In other embodiments, the anti-LAM antibodies have a CDR1, CDR2, and CDR3 region of the variable heavy chain having up to 85% identity with SEQ ID NOS: 16, 17 and 18, respectively. In other embodiments, the anti-LAM antibodies have a CDR1, CDR2, and CDR3 region of the variable heavy chain having up to 80% identity with SEQ ID NOS: 16, 17 and 18, respectively. In some embodiments, the anti-LAM antibodies have a CDR3 region of the variable heavy chain as set forth in SEQ ID NO: 18. In some embodiments, the anti-LAM antibodies have a CDR3 region of the variable heavy chain as set forth in SEQ ID NO: 18 with conservative sequence modifications. In other embodiments, the anti-LAM antibodies have a CDR3 region of the variable heavy chain having up to 95% identity with SEQ ID NO: 18. In other embodiments, the anti-LAM antibodies have a CDR3 region of the variable heavy chain having up to 90% identity with SEQ ID NO: 18. In other embodiments, the anti-LAM antibodies have a CDR3 region of the variable heavy chain having up to 85% identity with SEQ ID NO: 18. In other embodiments, the anti-LAM antibodies have a CDR3 region of the variable heavy chain having up to 80% identity with SEQ ID NO: 18.

TABLE 3

P95C1 Complimentary Determining Regions (CDR)

Light Chain

CDR1: QNVLDSANNRNY (SEQ ID NO: 13)
CDR2: WAS (SEQ ID NO: 14)
CDR3: TQYHRLPHT (SEQ ID NO: 15)

Heavy Chain

CDR1: GGSINTNNW (SEQ ID NO: 16)
CDR2: IHRHGDT (SEQ ID NO: 17)
CDR3: CPLGYCSGDDCHRVA (SEQ ID NO: 18)

The P95C1 IgM/x antibody was originally identified in supernatants of BCL6/Bcl-XL transduced memory B cells and cloned from these cells into IgM/x expression vectors using the standard RT-PCR protocol. The antibody was expressed by transfection of H and L chain vectors in Expi293 cells and cultured in standard Expi293 serum-free medium for several days. The secreted antibody was purified from the culture supernatant by affinity chromatography on columns conjugated with Protein L ligand. The bound antibody was released from the ligands by treatment with low PH buffer (0.2 M glycine-HCl, PH 2.5) and neutralized with 1/50 volume of 2 M tris buffer buffer (PH 8.8). The buffer was exchanged with PBS by dialysis or by several rounds of concentration on centrifugal filters (Amicon Ultra centrifugal filters, 30K mw limit).

The amino acid sequences for P95C1 heavy chain and light chain and their comparison with its closest germline are shown in FIG. 23. The amino acid and nucleotide sequences for P95C1 including the CDR3 region are copied below:

P95C1-Heavy chain variable region:
(SEQ ID NO: 47)
EVQLLESGPGLVRPWGTLSLTCAVS GGSINTNNW
WSWVRQSPGKGLEWIGE IHRHGDT
NYNPSLKRRVSISMDESMNQFSLRLISVTAADTAVYYC
CPLGYCSGDDCHRVA P95C1-Light chain variable region:
(SEQ ID NO: 48)
DIQMTQSPSSLSVSLGERATINCKSS
QNVLDSANNRNY FGWYQQKPGQPPKLLIS WAS
TRESGVPDRFSGSGSGTDFTLIISGLQVEDVAVYYC
TQYHRLPHT P95C1-Heavy chain:
(SEQ ID NO: 49)
gaggtgcagctcttggagtcgggcccaggactggtgaggcctggggga
ctctgtccctcacctgcgctgtctctggtggctccatcaatactaataa
ctggtggagttgggtccgccagtccccggggaagggctggagtggatt
ggagaaatccatcgtcatggggacaccaactacaacccgtcactcaaga
ggcgagtctccatatcgatggacgagtccatgaaccagttctccctgag
gcttatctctgtgaccgccgcggacacggccgtgtattactgttgtccc
ctaggatattgtagtggtgatgactgtcaccgagttgcctggggccggg
gaatcctggtcaccgtctcttcag P95C1-Light chain:
(SEQ ID NO: 50)
gacatccagatgacccagtctccatcctccctgtctgtgtctctgggcg
agagggccaccatcaactgcaagtccagccagaatgttttagacagcgc
caacaataggaactacttcggttggtaccagcagaaaccagggcagcct
cctaagctgctcatttcctgggcatctacacgggaatccggggtccctg
accgattcagtggcagcggctctgggacagacttcactctcatcatcag
cggcctgcaggttgaagatgtggcagtttattactgtacacagtatcat
agacttcctcacaccttcggccaagggacacgactggaaattaaac E. Further Variants and/or Derivatives One of ordinary skill in the art will appreciate that given the CDR regions of A194-01, P30B9, and P95C1, a wide number of engineered variants and/or derivatives of the anti-LAM antibodies disclosed herein may be constructed. For example, the anti-LAM antibodies of the present invention may be engineered into chimeric antibodies, humanized antibodies, and chimeric/humanized antibodies that exhibit affinity to one or more LAM epitopes. The antibodies may be engineered into bispecific antibodies, or may be engineered such that a single antibody construct binds to multiple LAM epitopes.

As described herein, the anti-LAM antibodies of the present invention may be engineered as homologous scFv-IgG constructs or as heterologous scFv-IgG constructs.

Homlogous scFv-IgG constructs of A194-01 are detailed in this Application (FIG. 17A). One non-limiting example of a heterologous scFv-IgG construct would be where the VH and VL chains of P30B9 were joined to the A194-01 IgG by a linker (FIG. 17B), although other VH/VL chains could be used, for example other anti-LAM antibodies such as murine anti-LAM antibodies. This may allow recognition of distinct epitopes in a single antigen molecule and may enhance multivalent binding and lead to increased affinity. Alternatively, heterologous scFv-IgG constructs may generate bispecific antibodies if the additional VH/VL chains target an antigen other than LAM.

The anti-LAM antibodies of the present invention may also be engineered to create scFv-IgM constructs, including both homologous and heterologous scFv-IgM constructs. A non-limiting example of a homologous scFv-IgM would be where P30B9 VH/VL chains are joind to the P30B9 IgM. In this construct, all binding sites would possess the same epitope specificity. A non-limiting example of a heterologous scFv-IgM construct is where the A194-01 scFv is joined to the P30B9 IgM, as opposed to the IgG constant domain [non-limiting [FIG. 17C]. Such engineered variant and/or derivative construct would retain the IgM-dependent recognition of dimannose epitopes of the parental P30B9 mAb and add the additional binding specificity of the A194-01 scFv. This may allow recognition of unique epitope arrays and lead to enhanced affinities, which could be valuable for improved point-of-care antigen detection assays.

F. Diagnostic Kits and Methods

One embodiment of the present invention relates to diagnostic kits and methods for the detection and/or quantification of LAM and/or PIM6 in a sample. As described herein, the anti-LAM antibodies A194-01 and P30B9, as well as the anti-PIM6/LAM antibody P95C1, including engineered variants and/or derivatives thereof, may be effective in detecting and/or quantifying the amount of LAM and/or PIM6 present in a sample. The LAM or PIM6 may be derived from any source, such as from *Mycobacterium tuberculosis* or *Mycobacterium smegmatis*, or from a serum or urine sample from a patient, e.g. a patient infected with a virulent strain of the *Mycobacterium tuberculosis*-complex. The LAM may be e.g. PILAM, ManLAM, or uncapped/unmodified AraLAM from other mycobacterial strains, such as *M. leprae*. These strains differ in the nature and extent of capping that occurs, and different antibody combinations would therefore have different specificities for the different forms, allowing some level of differentiation or typing to be performed. In particular, the IgM and engineered IgA1 isotype of P30B9, as well as the engineered IgM and scFv-IgG isotypes of A194-01, would be well-suited for detecting and/or quantifying di-mannose substituted ManLAM in a sample from a TB patient, which in some circumstances may comprise 80% of said LAM, and various isotypes of P30B9 would be especially effective at detecting and/or quantifying LAM bearing di-mannose substituted Ara6 residues, which as described herein are particularly prevalent on LAM derived from *Mycobacterium tuberculosis*. Since the P95C1 epitope is highly conserved in all species of LAM, this antibody, when coupled with a second antibody with the proper specificity, would be well-suited for detecting and/or quantifying various types of LAM in a sample. The IgG isotype of A194-01 binds very effectively to various forms of LAM, especially unsubstituted LAM, mono-mannonsylated LAM, and PILAM, and so would be effective at detecting and/or quantifying LAM derived from various strains of mycobacteria. The engineered IgM and scFv-IgG isotypes would also be quite effective at detecting and/or quantifying the amount of unsubstituted LAM, mono-mannonsylated LAM, and PILAM, and additionally may bind to di- and tri-mannose substituted LAM. This endows the engineered variants and/or derivatives of A194-01 with greater epitope recognition than the IgG isotype of A194-01 or the IgM isotype of P30B9, but at the expense of specificity for only those LAM epitopes that are specific to virulent strains of *Mycobacterium tuberculosis*. In some embodiments, quantifying said specificity for LAM and/or PIM6 is achieved by comparing the signal intensity of a serially diluted control sample having a known concentration of LAM and/or PIM6 in various direct binding assays or or antigen-capture assays.

Because the IgG isotype of A194-01, the IgM/IgA isotypes of P30B9, and the various isotypes of P95C1 bind to different LAM epitopes that are variably expressed in different strains of *Mycobacterium tuberculosis*, these particular isotypes could be used to differentiate the origination of a source of LAM; di-mannose substituted LAM, in particular di-mannose substituted Ara6 residues comprise the majority of LAM residues in virulent strains of *Mycobacterium tuberculosis*, whereas unsubstituted LAM/PILAM residues comprise the majority of LAM residues in fast growing non-virulent strains such as *Mycobacterium smegmatis*. For example, samples comprising LAM that bind only to A194-01 IgG and not P30B9 IgM likely did not originate from a virulent strain of *Mycobacterium tuberculosis*, whereas samples that bind to both P30B0 IgM and A194-01 IgG likely did originate from a virulent strain of *Mycobacterium tuberculosis* or a species of mycobacteria that introduces a similar capping motif.

Because the IgM/IgA isotypes of P30B9 are specific for di-mannose substituted ManLAM, which as detailed herein is the dominant form in virulent strains of *Mycobacterium tuberculosis*, said isotypes of P30B9 are ideal candidates for diagnostic kits and methods of use for diagnosing a patient as being infected with a virulent strain of the *Mycobacterium tuberculosis*-complex. Furthermore, the engineered IgM and scFv-IgG variants and/or derivatives of A194-01 may be suitable for such a use as they also recognize di-mannose and tri-mannose substituted ManLAM epitopes. Such a patient could have an ongoing or active infection, or the infection could be latent. The strain could be multi-drug resistant (MDR) or could be extensively-drug resistant (XDR). Specifically regarding patients having latent infections, change in LAM concentration in the serum or urine may be of particular importance, as increases in concentrations may signify a change to active infection. Alternatively, a decrease in concentration in an individual who has an active infection may signify that treatment is effective and should be continued, or an increase in concentration during treatment may indicate that the current treatment is not effective and should be eliminated, changed and/or modified.

The methods for diagnosing infection may including contacting a biological sample from said patient, e.g. blood, plasma, urine, sputum, or other bodily fluid, with at least one anti-LAM antibody and/or at least one anti-PIM6/LAM antibody of the present invention, particularly those anti-LAM antibodies that recognize di-mannose substituted ManLAM and those anti-PIM6/LAM antibodies that recognize at least one polymannose structure in the PIM6 mannan domain. These include, for example, IgM and IgA isotypes of P30B9, the engineered IgA, IgM and scFv-IgG isotypes of A194-01, and the various isotypes (IgG, IgM, IgA) of P95C1.

The antibodies used as the detecting reagent may be bound to reporter molecules such as those known in the art. The antibodies may be part of a kit, e.g. bound to a substrate or part of a sandwich assay. The kits may include a first anti-LAM or anti-PIM6/LAM capture antibody, a second anti-LAM or anti-PIM6/LAM detector (detection) antibody which is bound to a reporter molecule, and a support to which the capture anti-LAM or anti-PIM6/LAM antibody is bound. The first and second anti-LAM antibody may bind to the same LAM epitopes which are present in multiple copies on a single LAM molecule, or preferably they may bind to different epitopes present on a single LAM molecule. The LAM and PIM6 epitopes may be any of those described herein. The kits may include a third capture or detector (detection) antibody which binds to a non-competing site of the first and second antibody. This may increase the number of molecules captured and number of detector molecules bound and the strength of the corresponding signal.

The kits may include instructions for use, and may further contain various reagents, solvents, diluents, and/or pharmaceutically acceptable preservatives. The sensitivity of different biotin-labeled anti-LAM monoclonal antibodies in such an assay was conducted [FIG. 7]. In this assay, the murine anti-LAM antibody CS-35 was used to capture ManLAM from solution. This antibody was selected because of its broad specificity. CS-35 (250 ng/well) was used to capture ManLAM from solutions containing differing concentrations, and different biotinylated monoclonal antibodies were then used to probe for the presence of ManLAM in the capture well. Using a cut-off of 3×SD of background, the most sensitive probe was A194-01 IgM, which gave a strong signal (1.8 OD) for the highest dilution of ManLAM (0.016 ng/well). This was superior to the two FIND murine antibodies, which have been previously considered to be the best available probes for this type of assay.

G. Therapeutic Compositions, Methods, Vaccines, and Vectors

One embodiment of the present invention is directed towards pharmaceutical compositions comprising at least one anti-LAM antibody or anti-PIM6/LAM antibody of the present invention, as well as their methods of use in treating a patient in need thereof. The patient may have a latent or active infection by a virulent strain of *Mycobacterium tuberculosis*, and of particular utility, the strain may be multi-drug resistant (MDR) or extensively drug resistant (XDR) to traditional therapies/antibiotics. The anti-LAM and anti-PIM6/LAM antibodies utilized in these compositions and methods may be any anti-LAM antibody or anti-PIM6/LAM antibody of the present invention, but of particular utility may be those anti-LAM antibodies that recognize di-mannose capped ManLAM, particularly di-mannose capped Ara6 residues, e.g. P30B9 IgM or IgA1/IgA2 isotype and pentavalent A194-01 IgM or tetravalent scFv-IgG isotype and various isotypes of P95C1.

A pharmaceutically acceptable anti-LAM antibody and/or anti-PIM6/LAM antibody composition suitable for patient administration will contain an effective amount of the anti-LAM or anti-PIM6/LAM antibody or antibodies in a formulation which both retains biological activity while also promoting maximal stability during storage within an acceptable temperature range. The pharmaceutical compositions can also include, depending on the formulation desired, pharmaceutically acceptable diluents, pharmaceutically acceptable carriers and/or pharmaceutically acceptable excipients, or any such vehicle commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. The amount of an excipient that is useful in the pharmaceutical composition or formulation of this invention is an amount that serves to uniformly distribute the antibody throughout the composition so that it can be uniformly dispersed when it is to be delivered to a subject in need thereof. It may serve to dilute the antibody to a concentration which provides the desired beneficial palliative or curative results while at the same time minimizing any adverse side effects that might occur from too high a concentration. It may also have a preservative effect. Thus, for the antibody having a high physiological activity, more of the excipient will be employed. On the other hand, for any active ingredient(s) that exhibit a lower physiological activity, a lesser quantity of the excipient will be employed.

The pharmaceutically acceptable anti-LAM antibody and/or anti-PIM6/LAM antibody composition may be in liquid form or solid form. A solid formulation is generally lyophilized and brought into solution prior to administration for either single or multiple dosing. The formulations should not be exposed to extreme temperature or PH so as to avoid thermal denaturation. Thus, it is essential to formulate an antibody composition of the present invention within a biologically relevant PH range. A solution buffered to maintain a proper PH range during storage is indicated, especially for liquid formulations stored for longer periods of time between formulation and administration. To date, both liquid and solid formulations require storage at lower temperatures (usually 2-8° C.) in order to retain stability for longer periods. Formulated antibody compositions, especially liquid formulations, may contain a bacteriostat to prevent or minimize proteolysis during storage, including but not limited to effective concentrations (usually <1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antibody formulation, including but not limited to sugars as a cryoprotectant (including but not necessarily limited to polyhydroxy hydrocarbons such as sorbitol, mannitol, glycerol and dulcitol and/or disaccharides such as sucrose, lactose, maltose or trehalose) and, in some instances, a relevant salt (including but not limited to NaCl, KCl or LiCl). Such antibody formulations, especially liquid formulations slated for long term storage, will rely on a useful range of total osmolarity to both promote long term stability at temperature of 2-8° C., or higher, while also making the formulation useful for parenteral injection. An effective range of total osmolarity (the total number of molecules in solution) is from about 200 mOs/L to about 800 mOs/L. It will be apparent that the amount of a cyroprotectant, such as sucrose or sorbitol, will depend upon the amount of salt in the formulation in order for the total osmolarity of the solution to remain within an appropriate range. Therefore a salt free formulation may contain from about 5% to about 25% sucrose, with a preferred range of sucrose from about 7% to about 15%, with an especially preferred sucrose concentration in a salt free formulation being from 10% to 12%. Alternatively, a salt free sorbitol-based formulation may contain sorbitol within a range from about 3% to about 12%, with a preferred range from about 4% to 7%, and an especially preferred range is from about 5% to about 6% sorbitol in a salt-free formulation. Salt-free formulations will of course warrant increased ranges of the respective cryoprotectant in order to maintain effective osmolarity levels. These formulation may also contain a divalent cation (including but not necessarily limited to MgCl2, CaCl2) and MnCl2); and a non-32 ionic surfactant (including but not necessarily limited to Polysorbate-80 (Tween 80®), Polysorbate-60 (Tween 60®), Polysorbate-40 (Tween 40®) and Polysorbate-20 (Tween 20®), polyoxyethylene alkyl ethers, including but not limited to Brij 58®, Brij 35®, as well as others such as Triton X-100®, Triton X 114®, NP40®, Span 85 and the Pluronic series of non-ionic surfactants (e.g., Pluronic 121)). Any combination of such components, including probable inclusion of a bacteriostat, may be useful to fill the antibody-containing formulations of the present invention. The antibody composition of the present invention may also be a "chemical derivative", which describes an antibody that contains additional chemical moieties which are not normally a part of the immunogloblulin molecule (e.g., pegylation). Such moieties may improve the solubility, half-life, absorption, etc. of the base molecule. Alternatively, the moieties may attenuate undesirable side effects of the base molecule or decrease the toxicity of the base molecule.

Specific embodiments include PLGA microspheres, as discussed herein and as further known in the art, as well as polymer-based non-degradable vehicles comprising poly (ethylene-co-vinyl acetate; PEVAc). Additionally, controlled-release and localized delivery of antibody-based therapeutic products is reviewed in Grainger, et al., 2004, Expert Opin. Biol. Ther. 4(7): 1029-1044), hereby incorporated by reference in its entirety. Suitable microcapsules capable of encapsulating the antibody may also include hydroxymethylcellulose or gelatin-microcapsules and polymethyl methacrylate microcapsules prepared by coacervation techniques or by interfacial polymerization. See PCT publication WO 99/24061 entitled "Method for Producing IGF-1 Sustained-Release Formulations," wherein a protein is encapsulated in PLGA microspheres, this reference which is hereby incorporated herein by reference in its entirety. In addition, microemulsions or colloidal drug delivery systems such as liposomes and albumin microspheres, may also be used. Other preferred sustained-release compositions employ a bioadhesive to retain the antibody at the site of administration. As noted above, the sustained-release formulation may comprise a biodegradable polymer into which the antibody is disposed, which may provide for non-immediate release. Non-injectable devices may be described herein as an "implant", "pharmaceutical depot implant", "depot implant", "non-injectable depot" or some such similar term. Common depot implants may include, but are not limited to, solid biodegradable and non-biodegradable polymer devices (such as an extended polymer or coaxial rod shaped device), as well as numerous pump systems also known in the art. Injectable devices are split into bolus injections (release and dissipation of the drug subsequent to injection), and repository or depot injections, which provide a storage reservoir at the site of injection, allowing for sustained-release of the biological agent over time. A depot implant may be surgically tethered to the point of delivery so as to provide an adequate reservoir for the prolonged release of the antibody over time. Such a device will be capable of carrying the drug formulation in such quantities as therapeutically or prophylactically required for treatment over the pre-selected period. The depot implant may also provide protection to the formulation from degradation by body processes (such as proteases) for the duration of treatment. As known in the art, the term "sustained-release" refers to the gradual (continuous or discontinuous) release of such an agent from the block polymer matrix over an extended period of time. Regardless of the specific device, the sustained-release of the anti-LAM antibody and/or anti-PIM6/LAM antibody composition will result in a local biologically effective concentrations of the antibody. A sustained release of the biological agent(s) will be for a period of a single day, several days, a week or more; but most likely for a month or more, or up to about six months, depending on the formulation. Natural or synthetic polymers known in the art will be useful as a depot implant due to characteristics such as versatile degradation kinetics, safety, and biocompatibility. These copolymers can be manipulated to modify the pharmacokinetics of the active ingredient, shield the agent from enzymatic attack, as well as degrading over time at the site of attachment or injection. The artisan will understand that there are ample teachings in the art to manipulate the properties of these copolymers, including the respective production process, catalysts used, and final molecular weight of the sustained-release depot implant or depot injection. Natural polymers include but are not limited to proteins (e.g., collagen, albumin or gelatin); polysaccharides (cellulose, starch, alginates, chitin, chitosan, cyclodextrin, dextran, hyaluronic acid) and lipids. Biodegradable synthetic polymers may include but are not limited to various polyesters, copolymers of L-glutamic acid and gamma ethyl-L-glutamate (Sidman et al., 1983, Biopolymers 22:547-556), polylactides ([PLA]; U.S. Pat. No. 3,773, 919 and EP 058,481), polylactate polyglycolate (PLGA) such as polylactide-co-glycolide (see, for example, U.S. Pat. Nos. 4,767,628 and 5,654,008), polyglycolide (PG), polyethylene glycol (PEG) conjugates of poly($\alpha$-hydroxy acids), polyorthoesters, polyaspirins, polyphosphagenes, vinylpyrrolidone, polyvinyl alcohol (PVA), PVA-g-PLGA, PEGT-PBT copolymer (polyactive), methacrylates, poly(N-isopropylacrylamide), PEO—PPO-PEO (pluronics), PEO—PPO-PAA copolymers, PLGA-PEO-PLGA, polyorthoesters (POE), or any combinations thereof, as described above (see, for example, U.S. Pat. No. 6,991,654 and U.S. Pat. Appl. No. 20050187631, each of which is incorporated herein) by reference in its entirety, hydrogels (see, for example, Langer et al., 1981, J. Biomed. Mater. Res. 15:167-277; Langer, 1982, Chem. Tech. 12:98-105, non-degradable ethylene-vinyl acetate (e.g. ethylene vinyl acetate disks and poly(ethylene-co-vinyl acetate)), degradable lactic acid-glycolic acid copolymers such as the Lupron Depot™, poly-D-(−)-3-hydroxybutyric acid (EP 133,988), hyaluronic acid gels (see, for example, U.S. Pat. No. 4,636,524), alginic acid suspensions, polyorthoesters (POE), and the like. Polylactide (PLA) and its copolymers with glycolide (PLGA) have been well known in the art since the commercialization of the Lupron Depot™, approved in 1989 as the first parenteral sustained-release formulation utilizing PLA polymers. Additional examples of products which utilize PLA and PLGA as excipients to achieve sustained-release of the active ingredient include Amidox (PLA; periodontal disease), Nutropin Depot (PLGA; with HgH), and the Trelstar Depot (PLGA; prostate cancer). Other synthetic polymers included but are not limited to poly(c-caprolactone), poly3-hydroxybutyrate, poly($\beta$-malic acid) and poly(dioxanone)]; polyanhydrides, polyurethane (see WO 2005/013936), polyamides, cyclodestrans, polyorthoesters, n-vinyl alcohol, polyethylene oxide/polyethylene terephthalate, polyphosphate, polyphosphonate, polyorthoester, polycyanoacrylate, polyethylenegylcol, polydihydropyran, and polyacytal. Non-biodegradable devices include but are not limited to various cellulose derivatives (carboxymethyl cellulose, cellulose acetate, cellulose acetate propionate, ethyl cellulose, hydroxypropyl methyl cellulose) silicon-based implants (polydimethylsiloxane), acrylic polymers, (polymethacrylate, polymethylmethacrylate, polyhydroxy(ethylmethylacrylate), as well as polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-a-chloro-p-xylene, polymethylpentene, polysulfone and other related biostable polymers. Carriers suitable for sustained-release depot formulations include, but are not limited to, micospheres, films, capsules, particles, gels, coatings, matrices, wafers, pills or other pharmaceutical delivery compositions. Examples of such sustained-release formulations are described above. See also U.S. Pat. Nos. 6,953,593; 6,946,146; 6,656,508; 6,541,033; and 6,451,346, the contents of each which are incorporated herein by reference. The dosage form must be capable of carrying the drug formulation in such quantities and concentration as therapeutically required for treatment over the pre-selected period, and must provide sufficient protection to the formulation from degradation by body processes for the duration of treatment. For example, the dosage form can be surrounded by an exterior made of a material that has properties to protect against degradation from metabolic processes and the risk of, e.g., leakage, cracking, breakage, or distortion. This can prevent expelling of the dosage form contents in an uncontrolled manner under stresses it would be subjected to during use, e.g., due to physical forces exerted upon the drug release device as a result of normal joint articulation and other movements by the subject or for example, in convective drug delivery devices, physical forces associated with pressure generated within the reservoir. The drug reservoir or other means for holding or containing the drug must also be of such material as to avoid unintended reactions with the active agent formulation, and is preferably biocompatible (e.g., where the dosage form is implanted, it is substantially non-reactive with respect to a subject's body or body fluids). Generally, the respective biological agent(s) is administered to an individual for at least 12 hours to at least a week, and most likely via an implant designed to deliver a drug for at least 10, 20, 30, 100 days or at least 4 months, or at least 6 months or more, as required. The anti-LAM antibody and/or anti-PIM6/LAM antibody can be delivered at such relatively low volume rates, e.g., from about 0.001 ml/day to 1 ml/day so as to minimize tissue disturbance or trauma near the site where the formulation is released. The formulation may be released at a rate of, depending on the specific biological agent(s), at a low dose, e.g., from about 0.01 µg/hr or 0.1 µg/hr, 0.25 µg/hr, 1 μg/hr, generally up to about 200 μg/hr, or the formulation is delivered at a low volume rate e.g., a volume rate of from about 0.001 ml/day to about 1 ml/day, for example, 0.01 micrograms per day up to about 20 milligrams per day. Dosage depends on a number of factors such as potency, bioavailability, and toxicity of the active ingredient (e.g., IgG antibody) used and the requirements of the subject.

For in vivo treatment of human and non-human patients, the patient is administered or provided a pharmaceutical formulation including at least one anti-LAM antibody and/or at least one anti-PIM6/LAM antibody of the present invention. When used for in vivo therapy, the anti-LAM or anti-PIM6/LAM antibodies of the invention are administered to the patient in therapeutically effective amounts (i.e., amounts that eliminate or reduce the total bacterial load). The antibodies are administered to a human patient, in accord with known methods, such as intravenous administration, for example, as a bolus or by continuous infusion over a period of time, by intramuscular, intraperitoneal, intracerobrospinal, subcutaneous, intra-articular, intrasynovial, intrathecal, oral, topical, or inhalation routes. The antibodies can be administered parenterally, when possible, at the target cell site, or intravenously. In some embodiments, antibody is administered by intravenous or subcutaneous administration. Therapeutic compositions of the invention may be administered to a patient or subject systemically, parenterally, or locally. The above parameters for assessing successful treatment and improvement in the disease are readily measurable by routine procedures familiar to a physician.

For parenteral administration, the anti-LAM and anti-PIM6/LAM antibodies may be formulated in a unit dosage injectable form (solution, suspension, emulsion) in association with a pharmaceutically acceptable, parenteral vehicle. Examples of such vehicles include, but are not limited, water, saline, Ringer's solution, dextrose solution, and 5% human serum albumin. Non-aqueous vehicles include, but are not limited to, fixed oils and ethyl oleate. Liposomes can be used as carriers. The vehicle may contain minor amounts of additives such as substances that enhance isotonicity and chemical stability, such as, for example, buffers and preservatives.

The anti-LAM and anti-PIM6/LAM antibodies of the present invention may be administered to the host in any manner, strategy and/or combination available in the art in amounts sufficient to offer a therapeutic treatment against infection by a virulent strain of *Mycobacterium* tuberculosis-complex. These compositions may be provided to the individual by a variety of routes known in the art, especially parenteral routes, including but in no way limited to parenteral routes such as intravenous (IV), intramuscular (IM); or subcutaneous (SC) administration, with IV administration being the norm within the art of therapeutic antibody administration. These compositions may be administered as separate or multiple doses (i.e., administration of the antibody at staggered times by maintaining the sterile condition of the formulation through the treatment regime).

The dose and dosage regimen depends upon a variety of factors readily determined by a physician, such as the nature of the infection, for example, its therapeutic index, the patient, and the patient's history. Generally, a therapeutically effective amount of an antibody is administered to a patient. In some embodiments, the amount of antibody administered is in the range of about 0.01 mg/kg to about 1000 mg/kg of patient body weight, and any range in between. Depending on the type and severity of the infection, about 0.1 mg/kg to about 50 mg/kg body weight (for example, about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art. The above parameters for assessing successful treatment and improvement in the disease are readily measurable by routine procedures familiar to a physician.

These antibodies may also be administered via genetic vectors that express the paired heavy and light chains of a given antibody. This can involve a plasmid the efficiently expresses these genes or a viral vector, such as Adenoviral or Adeno-associated virus (AAV) vectors. These vectors can be delivered by injection into muscle tissue, and, depending on the dose, can secrete relatively large amount of secreted antibody into the circulation over a relatively long period of time.

Other therapeutic regimens may be combined with the administration of the anti-LAM and/or anti-PIM6/LAM antibodies of the present invention, for example, with another anti-LAM antibody, including but not limited to those anti-LAM antibodies known in the art, e.g. murine anti-LAM antibodies or humanized versions thereof, or with a pharmaceutical compound, such as, but not limited to, antibiotics. Antibiotics that are suitable for co-administration with the anti-LAM and/or anti-PIM6/LAM antibodies of the present invention include, but are not limited to, isoniazid, rifampin, rifapentine, ethambutol, pyrazinamide, bedaquiline, capreomycin, cycloserine, dexamethasone, kanamycin, and tinocordin. The combined administration includes co-administration, using separate formulations or a single pharmaceutical formulation, and consecutive administration in either order, wherein preferably there is a time period while both (or all) active agents simultaneously exert their biological activities. Such combined therapy can result in a synergistic therapeutic effect. The above parameters for assessing successful treatment and improvement in the disease are readily measurable by routine procedures familiar to a physician.

According to another embodiment, the present invention provides a passive vaccine or pharmaceutical compositions including at least one anti-LAM and/or anti-PIM6/LAM antibody of the invention and a pharmaceutically acceptable carrier. According to one embodiment, the vaccine or pharmaceutical compositions is a composition including at least one antibody described herein and a pharmaceutically acceptable carrier. The vaccine can include a plurality of the antibodies having the characteristics described herein in any combination and can further include other anti-LAM antibodies, including those of the present invention and those known in the art, e.g. murine anti-LAM antibodies or humanized versions thereof. The passive vaccine may include one or more pharmaceutically acceptable preservatives, carriers, and/or excipients, which are known in the art.

According to another embodiment, the present invention covers an active vaccine or pharmaceutical composition including administering to patient at least one antigenic LAM or PIM6 epitope. The particular epitope to be employed can be determined by testing the therapeutic activity of antibodies described in this patent in an appropriate animal model for TB infection and/or pathogenesis. This model species can be mouse, or guinea pig, or rabbit, or primate. For example, if A194-01 is most protective then a vaccine bearing a form of the A194-01 epitope would be used, whereas if P30B9 is most protective, di-mannose substituted Ara6 residues may be most effective at generating an appropriate humoral response. The active vaccine may include one or more adjuvants, which are known in the art, e.g. alum, aluminum hydroxide, aluminum phosphate, paraffin oil, and cytokines, e.g. IL-1, IL-2, IL-12. The active vaccine may comprise one or more pharmaceutically acceptable preservatives, carriers, and/or excipients, which are known in the art.

In some embodiments, the invention is directed to a recombinant vector, e.g. a plasmid, including a nucleic acid coding for an immunoglobulin heavy chain (Ig VH) of an anti-LAM antibody or an anti-PIM6/LAM antibody, and a second nucleic acid coding for an immunoglobulin light chain (Ig VL). In other embodiments, the first nucleic acid and the second nucleic acid are in two different recombinant vectors. According to another embodiment, the present invention covers a method of treating a tuberculosis infection in an individual including administering to said individual a first nucleic acid coding for an immunoglobulin heavy chain (Ig VH) of an anti-LAM or anti-PIM6/LAM antibody and a second nucleic acid coding for an immunoglobulin light chain (Ig VL) of an anti-LAM or anti-PIM6/LAM antibody wherein each of the nucleic acids is operably linked to a promoter region. The first nucleic acid and the second nucleic acid may be in a same recombinant vector or in two different recombinant vectors. The recombinant vector may be non-replicating viral vectors, e.g. adeno-associated viruses (AAV), or may be plasmids. In certain embodiments, the invention is directed to a cell transformed with one or more vectors disclosed herein. The above described antibodies and antibody compositions, vaccine compositions, and vectors can be administered for the prophylactic and therapeutic treatment of infection by virulent strains of the *Mycobacterium tuberculosis*-complex.

H. Equivalents

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference in their entireties.

As used herein and in the appended claims, the singular forms "a", "and" and "the" include plural references unless the context clearly dictates otherwise The term "about" refers to a range of values which would not be considered by a person of ordinary skill in the art as substantially different from the baseline values. For example, the term "about" may refer to a value that is within 20%, 15%, 10%, 9%, 8%, 7%, 6%, 5%, 4%, 3%, 2%, 1%, 0.5%, 0.1%, 0.05%, or 0.01% of the stated value, as well as values intervening such stated values.

Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

Each of the applications and patents cited in this text, as well as each document or reference, patient or non-patient literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

The following non-limiting examples serve to further illustrate the present invention.

EXAMPLES

EXAMPLE 1—The methods described herein were utilized to culture memory B cells in vitro and to molecularly clone immunoglobulin variable region genes to isolate several novel human monoclonal antibodies (mAbs) specific for LAM. One having ordinary skill in the art will recognize that these methods described herein can be adjusted to selectively identify rare antibodies with very high affinity, which could be present as few as 1 out of 100,000 memory B cells circulating in the blood of the patient.

Monoclonal Antibodies

Murine monoclonal antibodies: Hybridoma cell lines producing LAM-specific murine monoclonal antibodies CS-35 and CS-40 obtained from Dr. Delphi Chatterjee's lab were recloned to homogeneity, and the antibodies were purified by protein A chromatography.

Antibodies 906.41, 906.7, 908.1 and 922.5 were provided by Dr. John Spencer, and FIND25 and FIND170 were provided by Tobias Broger at FIND.

Antigens

*Mycobacterium tuberculosis* derived H37Rv lipoarabinomannan (LAM) (NR-14848) and *Mycobacterium smegmatis* derived LAM (NR-14860) were obtained from Colorado State University through BEI resources. LAM-derived glycoconjugates were synthesized in the Lowary lab.

ELISA Assays

Man-LAM (H37Rv) and PI-LAM (derived from *Mycobacterium smegmatic*) were diluted in CBC buffer (7.5 MM sodium carbonate, 17.4 MM sodium bicarbonate, PH 9.0) and plated at a concentration of 100 ng/well in 96 wells ELISA plates. After overnight incubation of plates at 4° C., wells were washed with PBS, PH 7.4 containing 0.05% Tween-20 (PBST), then blocked with 1% BSA (Sigma) in PBS buffer. PBST-washed plates were incubated for 1 hour at 37° C. with plasma derived from individuals infected with *Mycobacterium tuberculosis* and control plasma diluted in RPMI medium containing 2% FBS. PBST washed plates were then incubated for 1 hour with a 1:1000 dilution of alkaline phosphatase conjugated goat-anti-human IgG (γ-specific) (Millipore), or IgM (μ-specific) (Millipore), or IgA (α-specific). After PBST washing the color was developed with 50 ML of DEA buffer. The OD was measured at 405 nm by spectrophotometer. Titers were defined as the reciprocal dilution which produced an OD after subtracting the background OD taKEn the BSA coated plate, and were determined by exponential interpolation.

Plasma Titrations

The two purified antigens were obtained from the BEI Repository, and were plated overnight at 4° C. on 96 well ELISA plates at a concentration of 2 μg/ml, and the plates were then blocked with 1% BSA in 1×PBS. The LAM-specific titers of plasma were tested by incubating serially diluted samples at 37° C. for 1 hour, followed which the plates were washed three times with PBS+0.1% Tween20. Bound antibody was detected with a mixture of alkaline phosphatase conjugated goat anti-human kappa and goat anti-human lambda at 1:1,000 dilution in 1% BSA in PBS and the signals were developed by adding alkaline phosphate substrate in DEA buffer. Reactivity was measured as OD405 at 30 min.

Human Subjects

Patients with active infection with *Mycobacterium tuberculosis* were enrolled in the Lattimore practice at the Global Tuberculosis Institute. Active infection was defined by culture-proven tuberculosis disease or a diagnosis of clinical tuberculosis. This group included patients with a recent tuberculosis diagnosis, patients who were in the second month of the therapy. Uninfected patients were HIV-sero-negative, tuberculin skin test-negative, healthy volunteers with no history of *Bacillus* Calmette-Guerin (BCG) vaccination and negative for interferon-gamma release assay (IGRA) (Quantiferon Gold In-Tube, Cellestis Inc, Valencia, CA). Informed written consent was obtained from participants, and the study was approved by the Rutgers University Institutional Review Board.

TABLE 4

Clinical characteristics of TB patients used in this study

| Sample ID | Bleed date | Treatment start date | Diagnosis | Level of disease |
| --- | --- | --- | --- | --- |
| TB194 | Mar. 3, 2014 | Jan. 15, 2014 | TST (+), AFB Smear (−), NAAT (+) | Pulmonary TB |
| TB210 | Apr. 2, 2014 | Mar. 12, 2014 | TST (+), AFB Smear (+), Abnormal X-Ray | Pulmonary TB |
| TB256 | Jun. 30, 2014 | May 19, 2014 | TST (+), TBD (+), Abnormal X-Ray | Pulmonary TB |
| TB260 | Jun. 10, 2014 | Jul. 3, 2014 | TBD (+), AFB Smear (+), Abnormal X-Ray | Pulmonary TB |
| HC261 | Jul. 3, 2014 | NA | LTBI (−), TST (−) | LTBI (−), Non-contact |
| TB310 | Nov. 13, 2014 | Oct. 11, 2014 | TBD (−), AFB Smear (−), IGRA (+) | Pulmonary TB |
| TB314 | Nov. 18, 2014 | Oct. 13, 2014 | TBD (−), AFB Smear (−), IGRA (+) | Pulmonary TB |
| TB320 | Dec. 1, 2014 | Oct. 31, 2014 | TBD (+), TST (+), Abnormal X-Ray | Pulmonary TB |
| TB366 | Apr. 10, 2015 | Mar. 17, 2015 | TBD (+), TST (+), Abnormal X-Ray | Pulmonary TB |
| TB372 | Apr. 15, 2015 | Feb. 27, 2015 | TBD (+), TST (+), Abnormal X-Ray | Pulmonary TB |
| TB373 | Apr. 22, 2015 | Mar. 3, 2015 | TBD (+), TST (+), Abnormal X-Ray | Pulmonary TB |
| TB384 | May 5, 2015 | Mar. 6, 2015 | TBD (+), TST (+), Abnormal X-Ray | Pulmonary TB |

Table 4. Demographics of Human Subjects

1. Culture and Isolation of A194-01 (IgG Isotype)

Human monoclonal anti-LAM antibody A194-01, isotype IgG, was isolated from cultured memory B cells obtained from a TB-infected patient, TB-194. A critical component of the in vitro culture system is the presence of suitable feeder cells that can provide stimulation by CD40L, the ligand for CD40, a member of the TNF-receptor superfamily that is expressed on the surface of B cells and plays an essential role in mediating T cell-dependent immunoglobulin class switching and memory B cell development. Memory B cells were seeded on a feeder layer of CD40L-expressing MS40L-low cells. These cells express a low level of CD40L, and have been previously shown to efficiently support the replication of memory B cells and their maturation to plasma cells (Luo, X., et al., Blood, 2009. 113(7). These cells were generated by infecting murine stromal MS5 cells, that provide the B-lineage growth factor IL-7, with FLJW-CID40L, a virus that transduces human CD40L, originally obtained from Origene (Rockville, MD). Memory B cells were isolated with the MACS human memory B cell isolation kit from Miltenyi (Cat. #130-093-546), Non-B cells were excluded from PBMCs by negative selection with magnetic beads containing antibodies against the cell surface marker CD2, CD3, CD14, CD16, CD36, CD43, CD56, CD66b and glycophorin A. To further eliminate naïve B cells, memory B cell subpopulations were positively selected with magnetic beads coupled to antibody against the cell surface marker CD27, a marker for memory B cells that is also expressed in low levels on plasma cells, but not on naïve B cells. In the presence of CD40L-expressing feeder cells, these conditions support the replication of the memory B cells and their differentiation into plasmablasts secreting relatively high titers of Igs into culture supernatants.

Cultures were refed at weekly intervals by replacing half of the culture supernatant with fresh media. After 2-3 weeks there were sufficient B cells to produce ~1-5 µg/ml of secreted antibody. Assuming the presence of 100-1,000 distinct clones in each well, this corresponded to an average concentration of 1-10 ng/ML of Ig per B cell clone. This concentration is fairly low, and therefore this method was biased towards antibodies with relatively high affinities for the target antigens. Approximately 80,000 cells memory B cells were purified from the blood of this patient and cultured in 96 wells of a 96 well culture plate, for an initial density of ~800 cells/well.

Culture supernatants were screened by ELISA for the presence of antibodies against *Mycobacterium tuberculosis*-derived LAM. LAM was coated at a concentration of 2 µg/ML in 50 µL of bicarbonate coating buffer per well of a 96 wells ELISA plate and incubated at 4° C. overnight. The plate was washed with PBST (0.1% Tween 20 in 1×PBS) 4 times, and blocked with 200 µL of 2% nonfat milk in 1×PBS for 1 hour at 37° C. 100 µl of the culture supernatant was added to the corresponding wells of the ELISA plate containing LAM, and incubated for 1 hour at 37° C. After additional washing steps, AP-conjugated mouse anti-human Fab-antibody was added to detect bound human antibody. After half an hour of incubation at 37° C., 100 µL of AP-substrate in DEA buffer was added to the ELISA wells and reactivity was determined colorimetrically by measuring absorbance at 405 nm.

A positive signal (OD of ~1 at 1 hr) was detected in only 1 well out of 96 wells, indicating the rarity of these cells in this sample. Cells from the positive cells were re-cultured at a density of 5-10 cells/well in 10 wells of 96 well plates and rescreened for activity against LAM. This resulted in ~6 positive wells (OD of ~1 at 1 hr), again consistent with the low frequency of LAM-reactive cells and suggesting that the original positive well contained only a single LAM-positive B cell clone. Cells from several of the positive sub-clones were lysed and used to isolate the variable regions of the H and L chains, which were then cloned into H and L chain expression vectors. A total of 10 diverse VH and 9 VL sequences were isolated from these wells, and these were then tested for activity by transfecting individual combinations in 293 cells. Of 90 combinations tested, only a single combination of heavy chain (p9045-IgG1-VH) and light chain (p9044-Vk) gave a positive signal against LAM. Antibodies were expressed by cotransfection of corresponding heavy and light chain plasmids in Expi-292 cells as described by the manufacturer and grown in serum-free media. Antibodies were purified by affinity chromatography on either protein A beads (for IgG) or protein L beads (for IgG), and eluted with low PH buffer. The purified antibodies were concentrated and characterized by SS-PAGE for size and purity.

2. Isolation and Culturing of the IgM Isotype of P30R9

Human monoclonal anti-LAM antibody P30B9, isotype IgM, was isolated from cultured memory B cells obtained from a TB-infected patient, TB-314. PBMCs were isolated from the blood of patient TB-314 by centrifugation on a ficoll gradient, and ~30,000 memory B cells were purified as described above with the MACS human memory B cell isolation kit from Miltenyi. The purified memory B cells were cultured for 14 days by plating at 400 cells/well on monolayers of MS40-L cells grown in 96-well plates, in the presence of IL-21 (100 ng/ML), IL-10 (100 ng/ML), IL-2 (10 ng/ML), IL-4 (2 ng/ML), and CpG (1 µM), and cell supernatants screened by ELISA for binding to H37Rv ManLAM. ManLAM was coated at a concentration of 2 µg/ML in 50 µL of bicarbonate coating buffer per well of a 96 wells ELISA plate and incubated at 4° C. overnight. The plate was washed with PBST (0.1% Tween 20 in 1×PBS) 4 times, and blocked with 100 µL of 1% BSA in 1×PBS for 1 hour at 37° C. 50 µL of the culture supernatant or diluted antibody were added to the corresponding wells of the ELISA plate containing LAM, and incubated for 1 hour at 37° C. After additional washing steps, AP-conjugated goat anti-human IgG (H+L)-antibody was added to detect bound human antibody. After half an hour of incubation at 37° C., 50 µl of AP-substrate in DEA buffer was added to the ELISA wells and reactivity was determined by measuring yellow color at 405 nm. Only 1 out of 78 wells gave a positive signal when probed with a secondary goat anti-human IgG, IgA, IgM, kappa chain reagent. After expansion this well was transduced for BCL6 and Bcl-XL, linked by the self-cleaving porcine teschovirus-1 (P2A) peptide sequence and followed by a GFP reporter gene is driven by IRES. These two genes stabilize memory B cells for long-term replication, and allow the cells to be cultured even after selection of antigen positive cells by engagement of the BCR. The retroviral vectors were pseudotyped with Gibbon ape leukemia virus (GaLV) envelope glycoprotein with the R peptide deleted from the C-terminal TM domain. Successful transduction of primary B cells led to expression of BCL-6, Bcl-XL and the marker protein GFP. Viral titers were determined by counting GFP positive 293T cells under the fluorescent microscope. Activated B cells were transduced with retroviral vector in the presence of polybrene/retronectin.

After further expansion, the transduced cells were subcultured at limiting dilutions in the presence of IL-21 (100 ng/ML) and IL-2 (10 ng/ML). Well B9 on plate 30 (P30B9) was selected based on its strong LAM-binding activity and microscopic demonstration of the presence of a single clone. The P30B9 supernatant bound exclusively to wells coated with H37Rv-LAM, and not with wells coated with LAM derived from *Mycobacterium smegmatic* or alpha crystallin. The cells from this well were lysed and RNA isolated using the rNeasy mini kit (Qiagen) followed by CdnA synthesis with oligo (DT), using the superscript III CdnA synthesis system (Invitrogen). Antibody heavy and light chain variable regions were amplified by using Smith-Tiller's primers, and cloned in human heavy and light chain expression vectors. The heavy chain variable region was initially cloned into a standard IgG vector. However, when combined with the light chain sequence cloned into a human kappa chain expression vector no LAM-binding activity was detected. At that point, the ManLAM-reactive antibodies produced in the original stably transduced polyclonal well were re-probed with isotype-specific reagents, and found to be exclusively IgM. The P30B9 VH sequence was subsequently cloned into an IgM H chain constant region expression vector, and good binding activity was obtained upon co-transfection with the corresponding kappa chain.

3. Characterization of Epitope Specificity of A194-01 IgG and P30B9 IgM and Murine Anti-LAM Antibodies Against LAM A. To define the epitopes recognized by A194-01 IgG and P30B9 IgM, the binding activities of said antibodies were compared to those of a number of murine LAM-specific monoclonal antibodies (CS-35, CS-40, FIND25, FIND170, and the 900 series of monoclonal antibodies represented by 908.1) against a series of 25 glycoconjugates in which synthetic glycans representing different structures present in LAM were conjugated to bovine serum albumin (FIG. 4A-1-4A-4). These ranged in size from 4 to 26 carbohydrate rings and represented the range of structural motifs known to be present in various mycobacterial LAMs, including a number of poly-arabinose structures both uncapped and capped with phosphoinositol, alpha(1→2)-linked mono, di- and tri-Manp mannose structures, and 5-deoxy-5-methylthiopentofuranosyl (MTX) motifs and various capped Ara4 and Ara6 structures.

Figures 2, 4B:
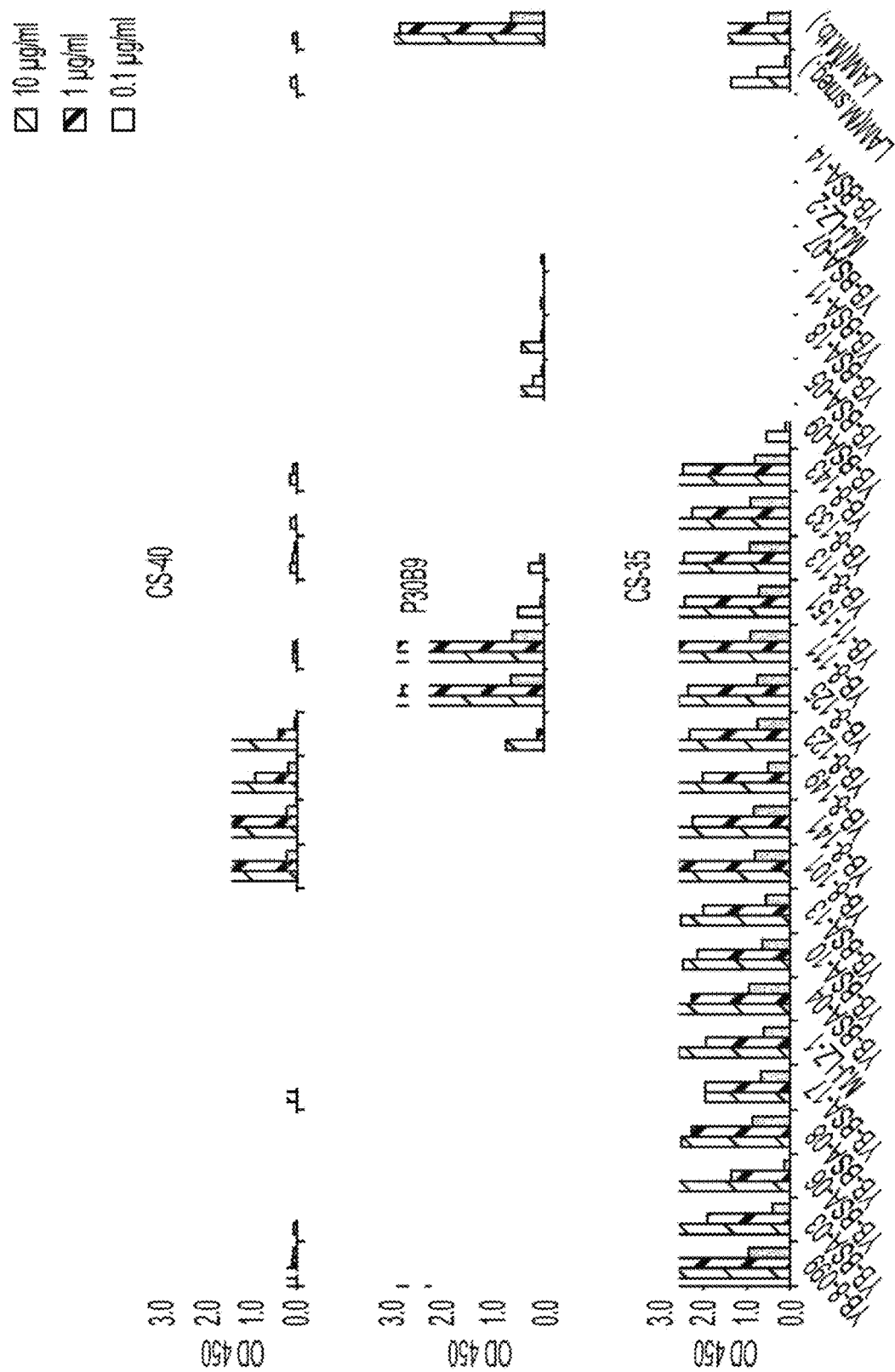
Figures 2, 5C:
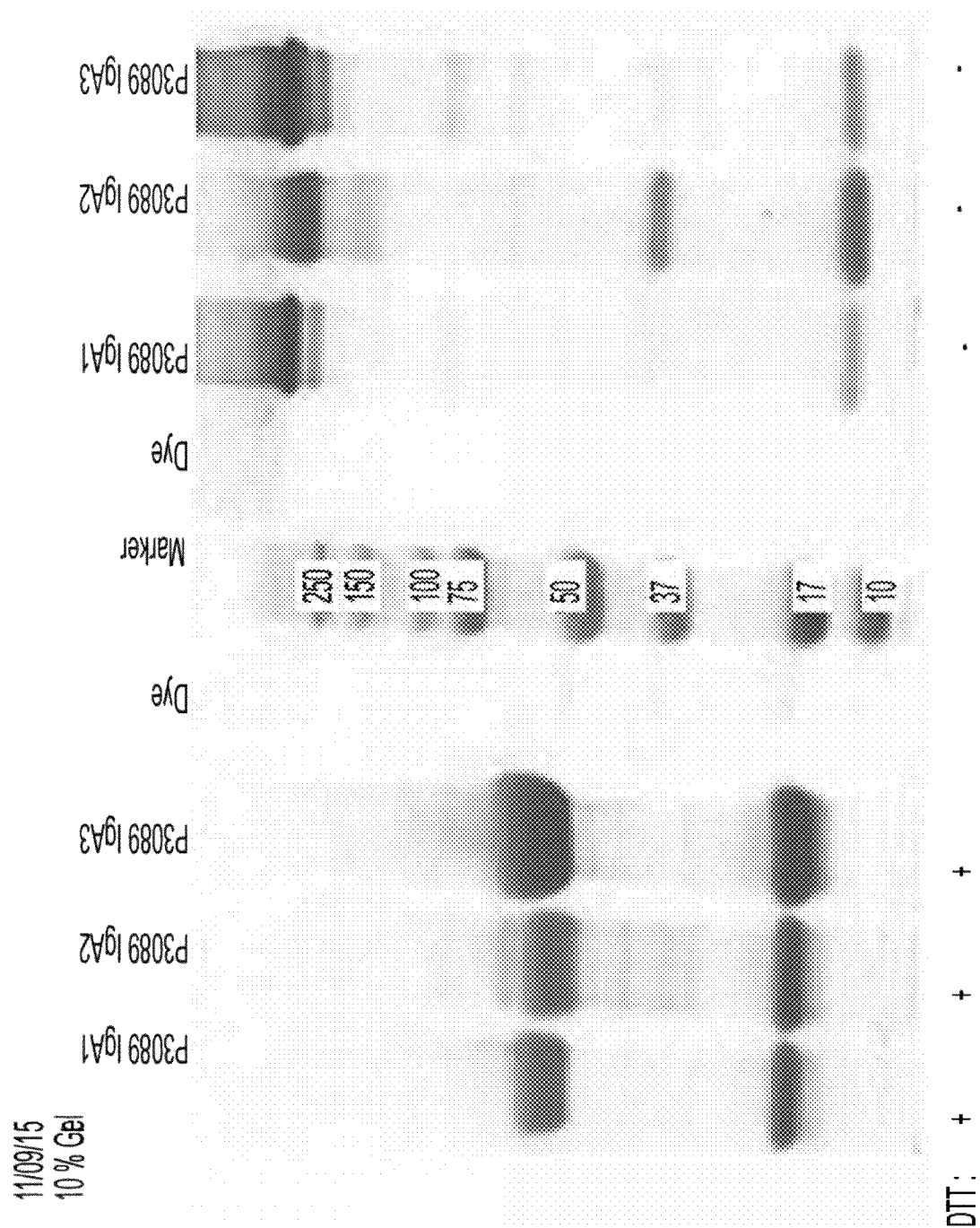

Six distinct reactivity patterns were obtained with this antigenic panel for these monoclonal antibodies (FIG. 4B-1-4B-2). The relative affinities of the monoclonal antibodies for these antigens were indicated by the titration profile; high affinity reactions retain high reactivity at the intermediate dilution, whereas low affinity is indicated by a rapid drop in reactivity. The broadest pattern was seen for mouse mAb CS-35, which reacted with modest affinity with LAM derived from *Mycobacterium tuberculosis* and LAM derived from *Mycobacterium smegmatis*, and recognized both capped or uncapped structures containing the basic Ara4 and Ara6 motifs, consistent with the known specificity of this mAb for the β-D-Araf-(1→2)-α-D-Araf-(1→5)-α-D-Araf-(1→5)-α-D-Araf motif.

The human monoclonal anti-LAM antibody A194-01 IgG also recognized a large fraction of these structures and in many cases possessed the strongest affinity. A109-01 IgG bound strongly to all uncapped Ara4 and Ara6 structures and to the phosphoinositol-capped Ara4 structure, and less strongly to a subset of the mannose-capped structures. A109-01 IgG bound well with mono-mannose capped structures, but very weakly with the di- and tri-mannose structures, although reactivity with the latter structures was enhanced when the MTX substitution was present. Four of the 900 series of mouse monoclonal antibodies (represented by 908.1) reacted with relatively weak affinity with all uncapped Ara4 and Ara6 structures, but not with any of the capped structures. Two mouse monoclonal antibodies from FIND (FIND25, also referred to as KI25), bound strongly with all Ara6 structures, irrespective of the presence of absence of capping, but did not recognize any Ara4 structures. CS-40, known to react specifically with ManLAM, reacted weakly with LAM derived from *Mycobacterium tuberculosis*, and bound preferentially with mono-mannose-capped Ara4 and Ara6 structures.

The human monoclonal anti-LAM antibody P30B9 IgM, reacted strongly and with high specificity with ManLAM derived from *Mycobacterium tuberculosis* and with dimannose-capped Ara4 and Ara6 structures, and with considerably weaker activity to the other mannose-containing structures. Visualization of this residual activity is dependent on the assay conditions, and shows up in some assay formats (e.g., FIGS. 4B, 8) but not in others (e.g., FIGS. 16, 18). Without wishing to be bound by theory, the relative specificity of P30B9 IgM for di-mannose capped structures is potentially clinically relevant, since terminal mannosyl units are known to mediate binding of lipoarabinomannan from virulent strains of the *Mycobacterium tuberculosis*-complex to human macrophages, and, furthermore, di-mannose caps are known to be the dominant modification of LAM derived from *Mycobacterium tuberculosis*.

Similar results were obtained when the epitope specificity of the A104-01 IgG and the P30B9 IgM were further mapped in a microarray assay against a larger panel of carbohydrate antigens. This panel included several additional polymannose structures which were recognized by the P30B9 IgM, but not by any of the other antibodies tested (FIG. 8A-8B-1-8-3). This was consistent with the P30B9 IgM preference for di-mannose capped Ara4 and Ara6 structures, particularly, but not necessarily, those containing Man-α(1→2)-Man-α(1→5) linked to the terminal arabinose. The P30B9 IgM also reacted strongly with a pentamannose structure (59. AS-3-71) that contained the Man-α(1→2)-Man-α(1→6) but only weakly to a similar structure containing the Man-α(1→3)-Man-α(1→6) (50. YB-BSA-18). Despite its preference for the α(1→2) linkage, the P30B9 IgM did not react with AS-2-91, a tetra-mannose structure that contained the Man-α(1→2) linkage along with an additional mannose linked α(1→6) to the second mannose. Without wishing to be bound by theory, this suggests that the specificity of the IgM isotype of P30B9 may require that both sugars of the dimannose motif not contain any additional substitutions.

Figure 9A:
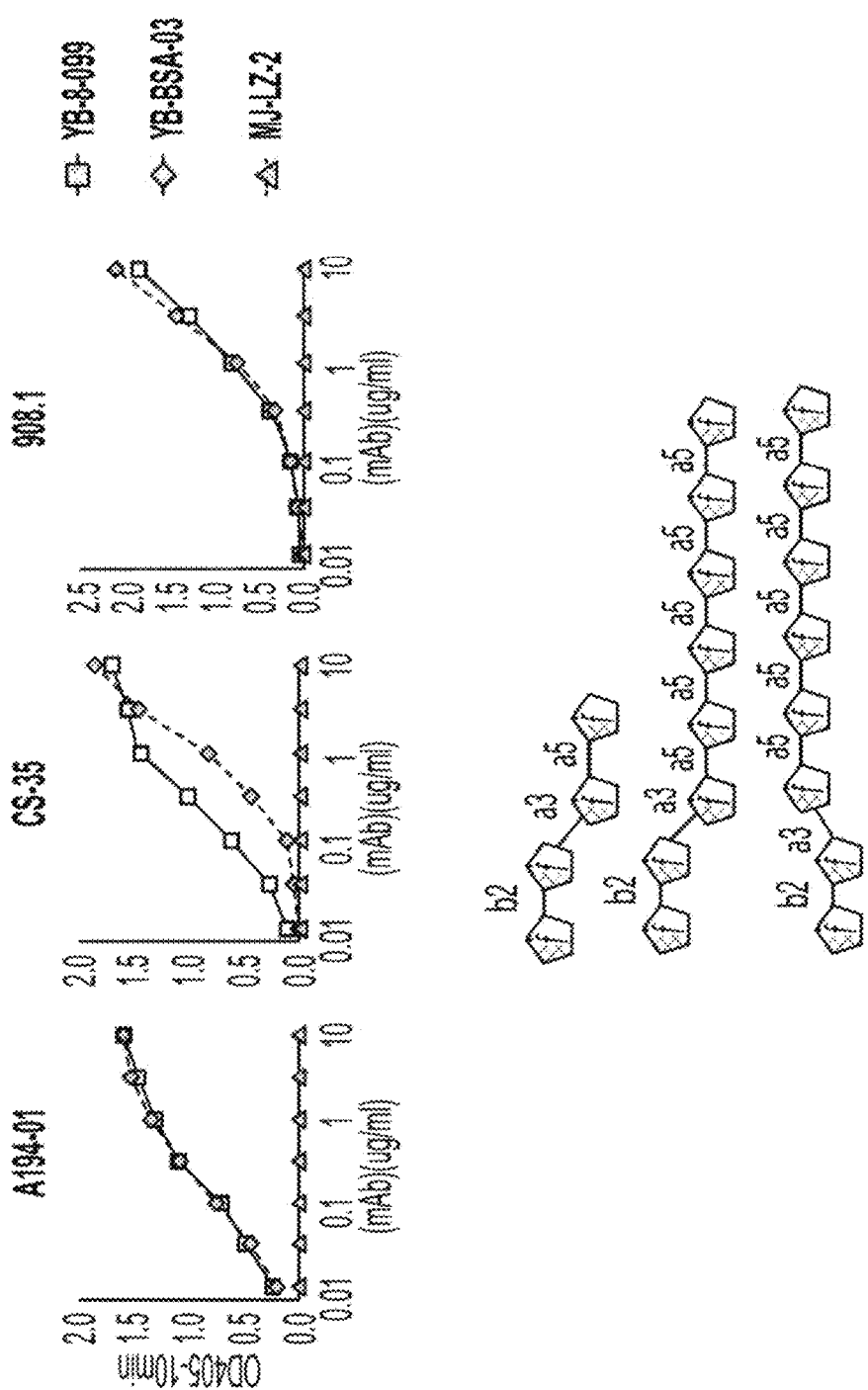

B. A more precise titration to map the fine specificities of these monoclonal antibodies towards the LAM-derived glycans demonstrated the critical role of the terminal β-D-Araf-(1→2)-α-D-Araf-(1→5) disaccharide in antibody recognition of Ara4 structures. The Ara4 structure consists of a β-D-Araf-(1→2)-α-D-Araf-(1→5)-α-D-Araf-(1→5)-α-D-Araf tetrasaccharide, while the Ara6 structure contains an additional β-D-Araf-(1→2)-α-D-Araf-(1→3) disaccharide branch at the second sugar. Three of the monoclonal antibodies bound to both Ara4 and Ara6 structures independent of mannose capping. All three monoclonal antibodies bound to the Ara4 structure (YB-8-099) and to YB-BSA-03, corresponding to the Ara4 structure with four additional α-D-Araf-(1→5) sugars at the reducing end (FIG. 9A). However, none of the monoclonal antibodies bound to a related octasaccharide (MJ-LZ-2) that contained a terminal β-D-Araf-(1→2)-α-D-Araf-(1→3) disaccharide, corresponding to the lower branch of the Ara6 structure. This indicated that the upper branch of the Ara6 structure containing the β-D-Araf-(1→2)-α-D-Araf-(1→5) linkage was recognized by these monoclonal antibodies, and not the lower branch that contained the β-D-Araf-(1→2)-α-D-Araf-(1→3) disaccharide.

Figures 1, 9B:
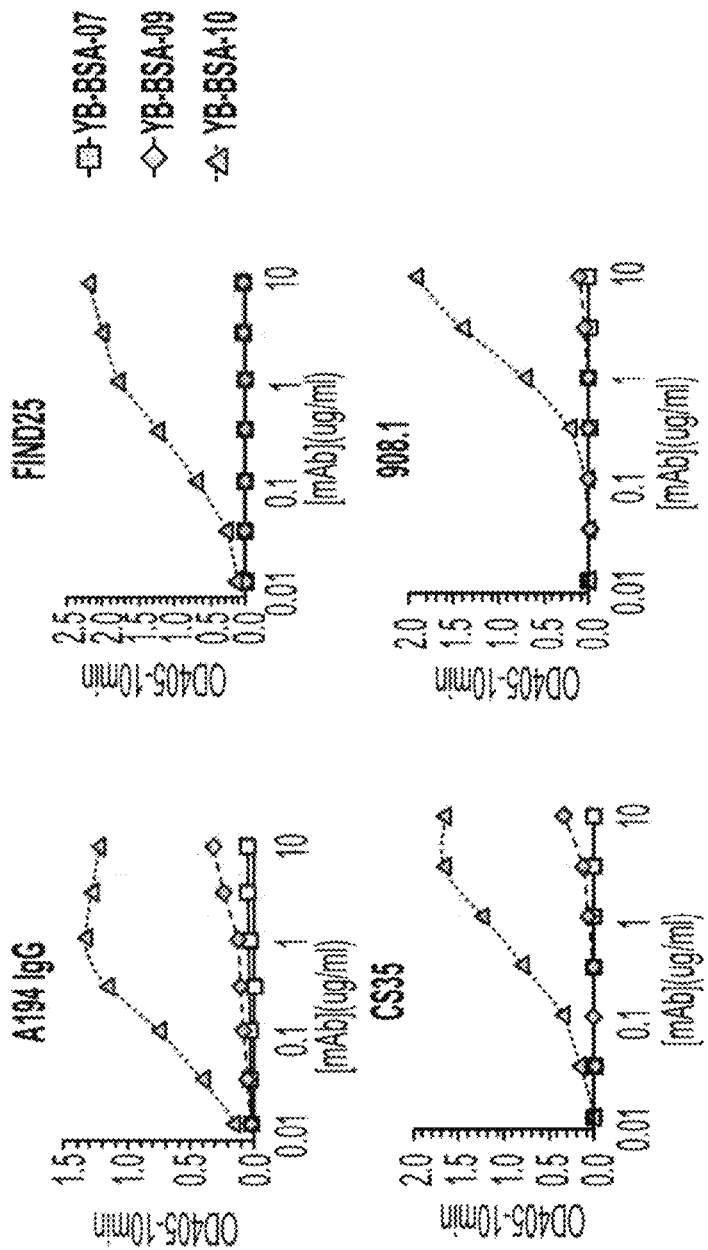
Figures 2, 9B:
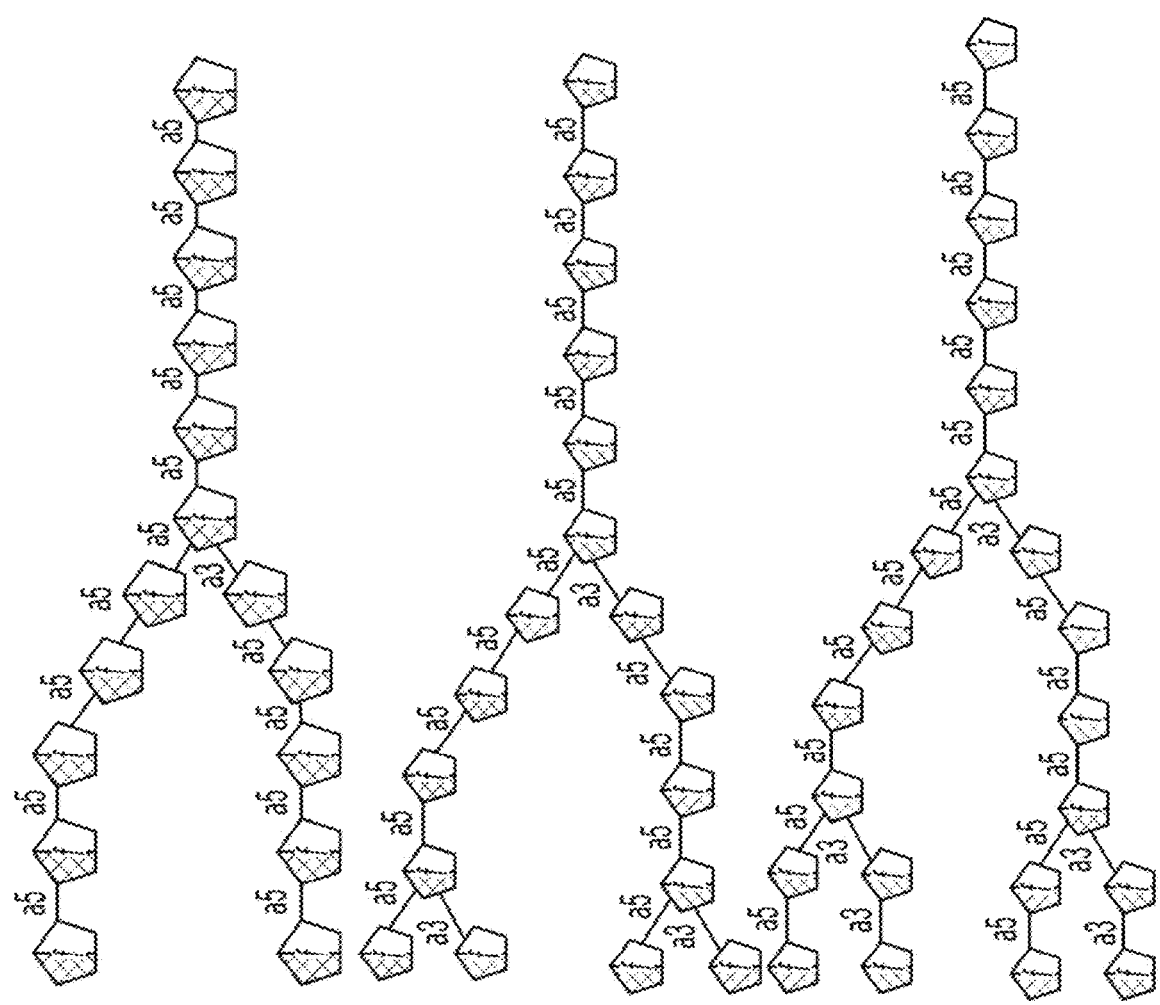

The role of the terminal β-D-Araf-(1→2) linkage in antibody recognition was examined by probing the reactivity of these monoclonal antibodies and the Ara6-dependent FIND25 antibody to three related poly α-D-Araf-(1→5) structures that contained truncated forms of the terminal disaccharide (FIG. 9B-1-9B-2). All three structures also contained an internal α-D-Araf-(1→3) branch. YB-BSA-07 terminated in a linear α-D-Araf-(1→5) structure, and was completely unreactive with all of the anti-LAM antibodies. YB-BSA-09 contained additional α-D-Araf sugars attached via a (1→3) branch at the penultimate sugars of the two longer branches, resembling the structure of the Ara6 branch. This structure was recognized only weakly by the higher concentrations tested of the IgG isotype of A194-01 and by CS-35. YB-BSA-10 included terminal β-D-Araf-(1→2) sugars at each of the branches, forming two complete Ara6 structures at the non-reducing ends of the polysaccharide. This structure was recognized by all of the monoclonal antibodies, with relative binding strengths consistent with their affinities towards the natural LAM antigen. These assays indicated that a terminal β-D-Araf-(1→2)-α-D-Araf-(1→5) disaccharide was a critical component of all of the available Arabinose-reactive LAM-specific monoclonal antibodies.

C. A critical distinction between pathogenic strains of the *Mycobacterium tuberculosis*-complex such as *Mycobacterium tuberculosis* and *Mycobacterium bovis* and non-pathogenic rapidly growing strains such as *Mycobacterium smegmatis* is the presence of mannose-capped termini on the pathogenic strains. As such, monoclonal antibodies that are specific for distinct mannosylated structures could be useful for structural studies and for determining the functional contributions of these modifications. The activities of two of the monoclonal antibodies characterized in this study, CS-35 and FIND25/170, were completely unaffected by the presence or absence of mannose caps. Binding of the 900 series of monoclonal antibodies on the other hand was completely abrogated by mannosylation of any sort (FIG. 4A-1-4A-4, FIG. 4B-1-4B-2). CS-40 on the other hand, bound only weakly with the unmodified Ara4 glycan (YB-8-099) but strongly with Ara4 (YB-8-101) and Ara6 (YB-8-149) structures that contained single mannose caps. This experiment used a modified CS-40 in which the mouse heavy chain domain was substituted with the human IgGI constant sequence, since this resulted in more sensitive detection of binding compared to the natural mouse antibody used in FIG. 4A-1-4A-4, FIG. 4B-1-4B-2. The weak reactivity of CS-40 with the uncapped arabinofuranose structure was reflected in its weak reactivity with *M. smegmatis* LAM, compared to M. tb LAM. Attachment of an α(1→4) linked MSX sugar to the terminal mannose (i.e., YB-8-141 and YB-8-149) had no effect on binding affinity, whereas attachment of a second α(1→2) linked mannose sugar (YB-8-111 and YB-8-125) to generate a dimannose cap completely abrogated CS-40 reactivity (FIG. 16A-16B).

A194-01 possessed a more complex reactivity pattern. A194-01 bound strongly with uncapped arabinofuranosyl side chains and with mono-mannose capped Ara4 (YB-8-101) and Ara6 (YB-8-123) structures, but this mAb reacted only weakly with the dimannose-capped Ara4 (YB-8-111) and even more poorly with tri-mannose capped Ara4 (YB-8-113) and almost not at all for dimannose-capped Ara6 (YB-8-125). As was seen for CS-40, MTX substitution to the monomannose structures (YB-8-141, YB-8-149) did not inhibit binding of A104-01, and of particular interest, MSX addition significantly improved recognition of the dimannose- and trimannose-capped Ara4 structures (YB-8-133, YB-8-143). Consistent with the high selectivity of P30B9 for ManLAM, the mAb bound specifically with dimannose-capped Ara4 (YB-111) and Ara6 (YB-8-125) structures. In contrast to the benign or beneficial effects of MSX substitution on binding of CS-40 and A194-01, this substitution resulted in the complete loss of reactivity of P30B9, as did addition of an additional mannose to form the trimannose capped structures. These results suggested that the different monoclonal antibodies recognized different regions and structural aspects of LAM structure, with some binding solely to the arabinofuranose side chains and others binding with different levels of specificity to the capping motifs.

The relative binding specificities and affinities of the Ara6-reactive antibodies were compared for representative glycoconjugates (FIG. 11) The overall patterns were consistent with those obtained for the natural antigens, PILAM and ManLAM (FIG. 3) and in the preliminary titration against the glyconconjugates (FIG. 4A-1-4A-4, FIG. 4B-1-4B-2). The human A194-01 IgG possessed higher relative affinity for all of the uncapped structures and for the MSX-substituted Ara6-monomannose structure (YB-8-149), reacted with equal affinity with the Ara6 structure with single mannose caps, but did not recognize the structures with di-mannose or tri-mannose caps. FIND25 bound with similar or slightly higher affinity than CS-35 to all structures that bore the standard Ara6 structure, both in capped or uncapped forms, but did not bind to two structures (YB-BSA-06 and YB-BSA-08) in which one of the branches was extended at the non-reducing end away from the branching point. 908.1 bound with weaker affinity to all of the uncapped structures, including the latter two, but did not recognize any of the mannose capped structures4.

Competition Studies Involving Anti-LAM Monoclonal Antibodies a, Overview

The ability of individual antibodies to compete for binding of biotinylated probe mAbs to LAM was titered by ELISA. Typical competition curves are shown in FIG. 16A for four of the anti-LAM antibodies, A194-01, CS-35, FIND25 and P30B9. As expected, the biotinylated antibodies were all competed by their excess amounts of their unlabeled versions. Murine anti-LAM antibodiy 908.6 competed poorly, if at all, against the other antibodies. This was due to some extent to the weak affinity of this antibody, but also reflects the restriction of 908.6 binding to uncapped structures, and suggests that capped structures were the dominant targets in ManLAM recognized by CS-35 and FIND25.

In agreement with its broad reactivity, CS-35 competed fully for binding of all of the probe antibodies, although its competition with biotinylated A194-01 was less potent than A194-01 for itself, consistent with a lower affinity of CS-35 for LAM. Whereas CS-35 competed fully against biotinylated FIND25, FIND25 competed only partially against labeled CS-35 (~74% maximum competition), and even less effectively against A194-01 (~50%). Without wishing to be bound by theory, this result presumably reflects the presence of Ara4 structures that are recognized by A194-01 and CS-35, but not by FIND25, which binds exclusively to the Ara6 motif. The fact that FIND25 competed with the majority of CS-35 binding suggested that Ara6 structures were more common than Ara4 structures. Despite its high affinity, A194-01 competed only against itself, but not against either CS-35 or FIND25, further suggesting that the targets in LAM recognized by the latter two antibodies predominantly consisted of structures (e.g. di-mannose and tri-mannose-capped structures) that are not recognized by A194-01. In contrast to this result, A194-01 did compete fully and efficiently for binding of FIND25 to the un-mannosylated PILAM, consistent with the role for efficient mannose capping of Ara6 structures in the lack of competition in ManLAM.

Competition studies using the antibody P30B9 further supported the conclusion that the great majority of Ara6 structures in ManLAM were capped with di-mannose, and that the bulk of dimannose caps resided on Ara6 structures.

P30B9 competed with ~70% of binding of FIND25 and ~80% of the binding of CS-35 to ManLAM, confirming that the majority of the structures recognized by these mouse mAbs were also recognized by P30B9. P30B9 binding to ManLAM was competed efficiently by itself, and by both CS-35 and FIND25. The level of competition of P30B9 by FIND25 was close to 100%, indicating that essentially all of the dimannose-dependent P30B9 binding sites were located on Ara6 sites, and few on Ara4 structures. As expected, A194-01 competed very poorly for binding of P30B9 to ManLAM, and 908.7 did not compete at all, consistent with the poor recognition of dimannose-capped structures by these antibodies. The inability of the latter antibodies to compete efficiently for binding of P30B9 confirmed that this effect required binding of the competing mAb to the same branch as the probe mAb, and that binding to heterologous epitopes located on an adjacent branch of the same molecule did not lead to effective competition.

B. Relative A194-01 IgG and P30B9 IgM Affinities by Competition Assays

Figure 10A:
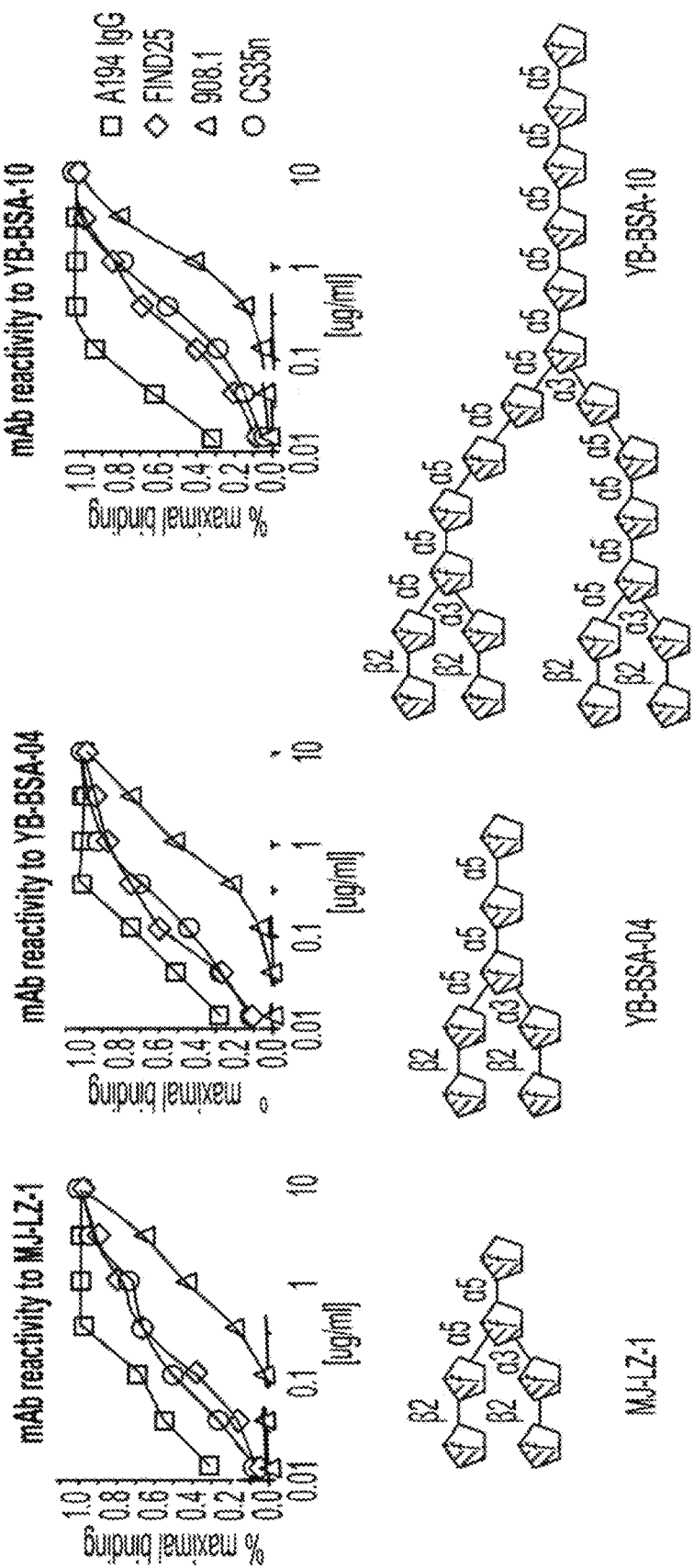
FIG. 10A-10C Binding curves of A194-01 IgG and three murine anti-LAM antibodies against various Ara6-containing glycoconjugates, showing the effect of different capping motifs on antibody reactivity.
Figure 10B:
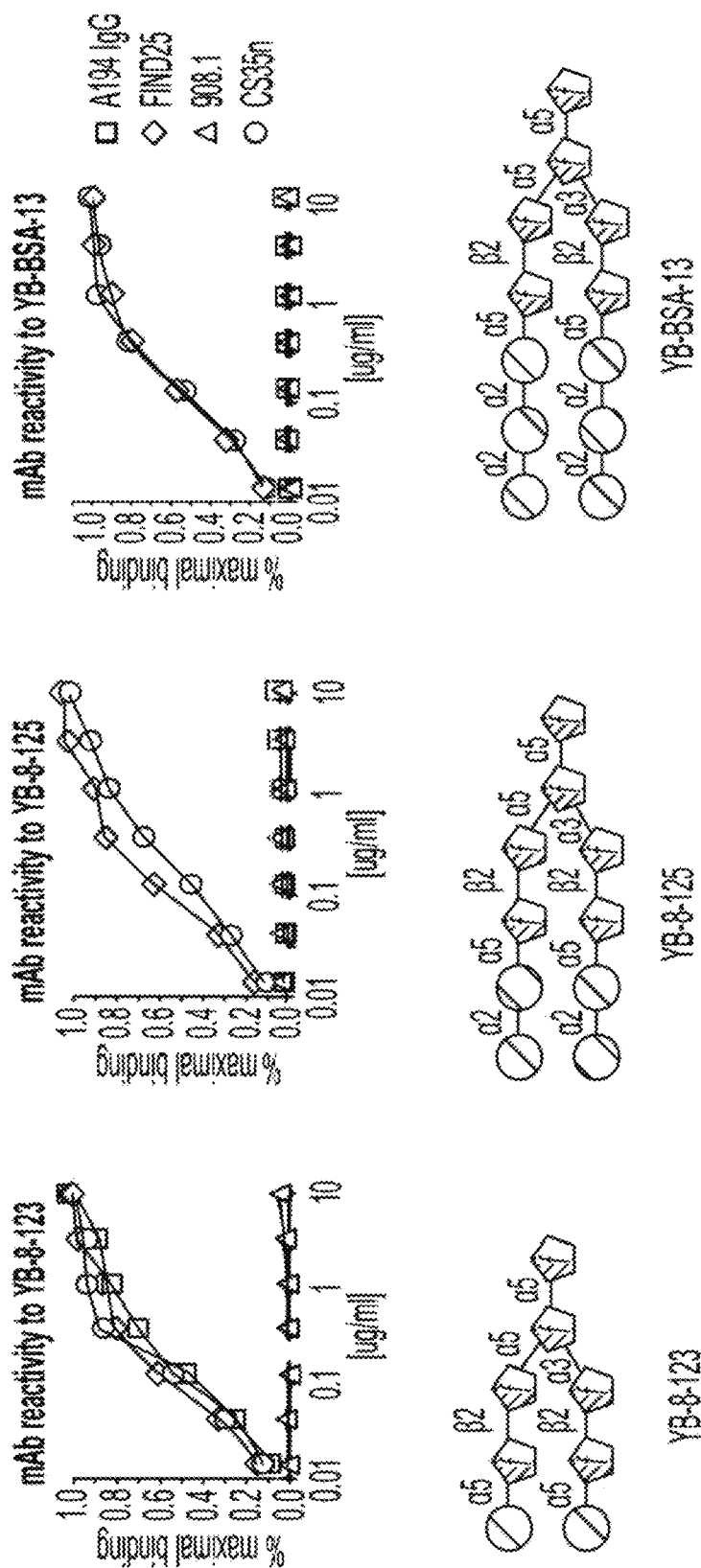
Figure 10C:
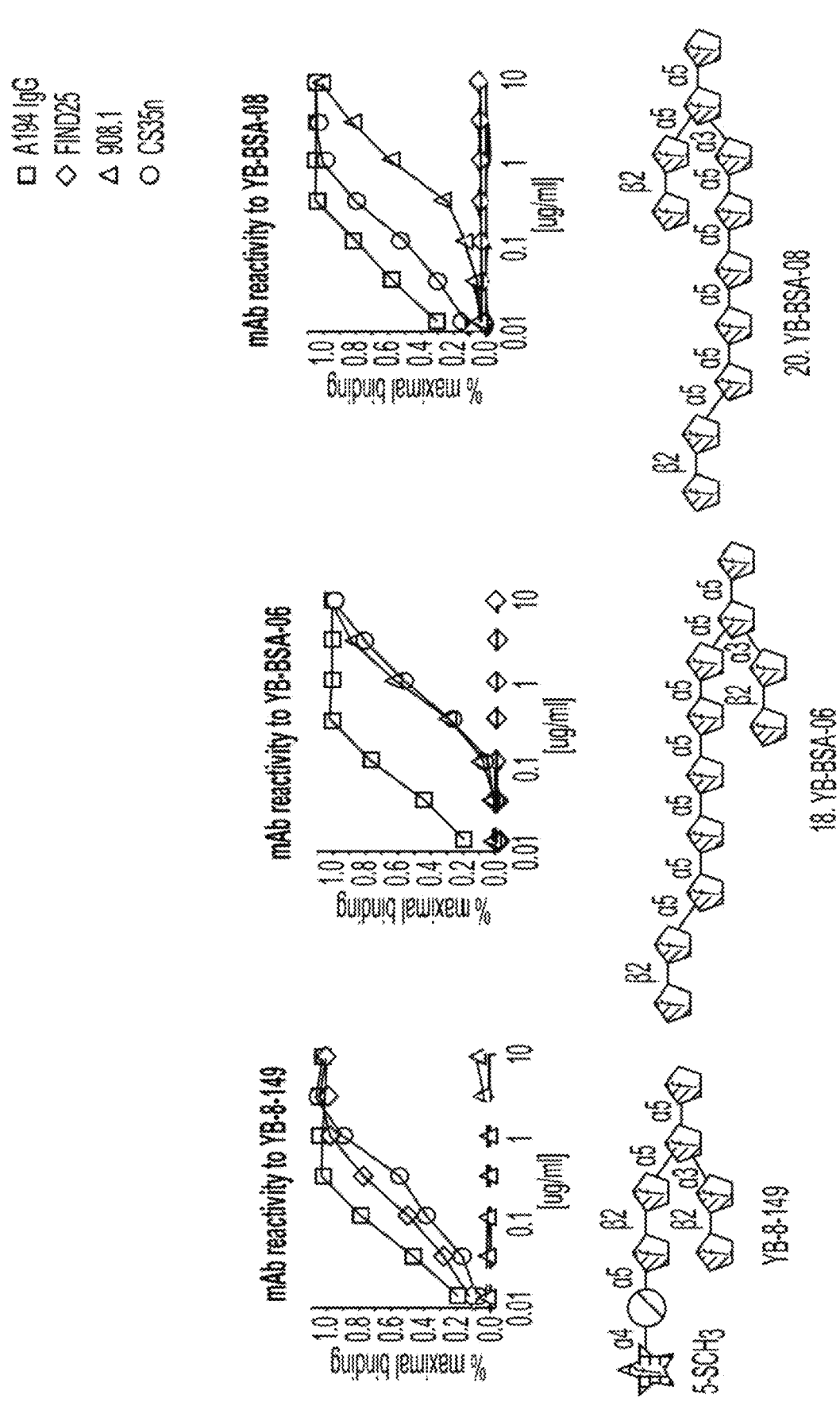
Figure 11:
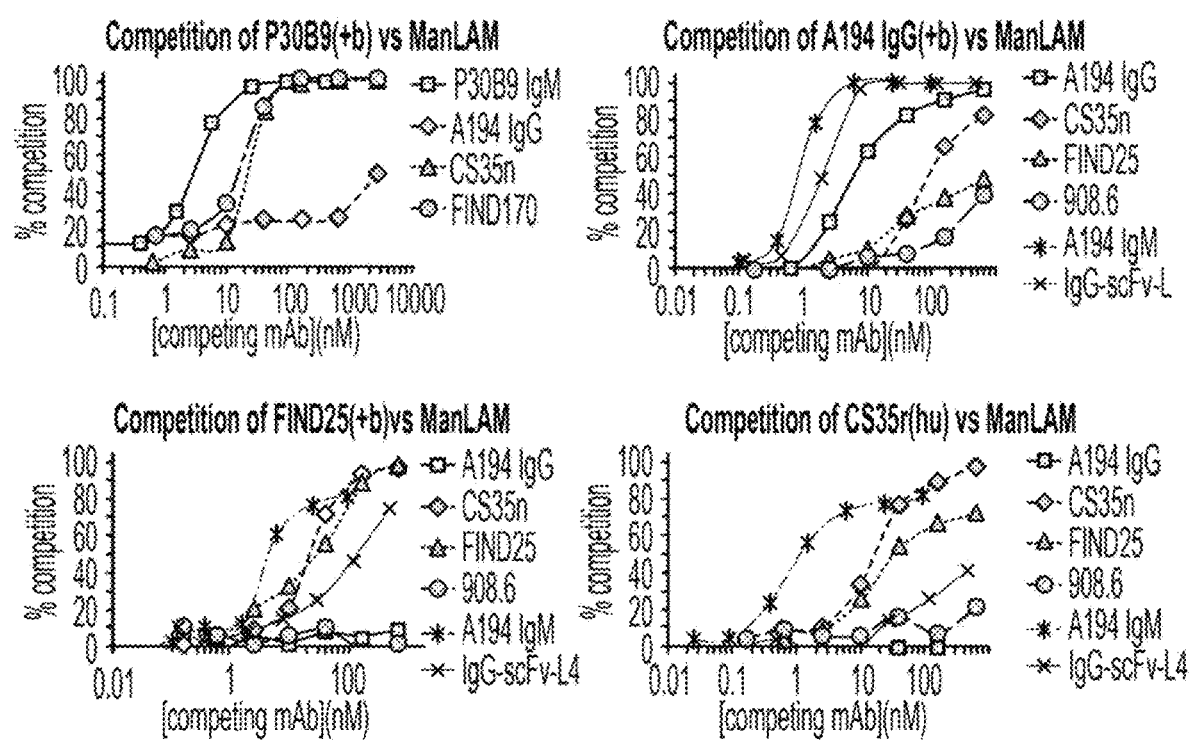
FIG. 11 Binding competition studies to measure the ability of individual anti-LAM antibodies to compete for binding of a probe antibody to the ManLAM antigen.

Mapping the reactivity of individual monoclonal anti-LAM antibodies, including the IgG isotype of A194-01 and the IgM isotype of P30B9, to specific glycan structures allowed for characterization of the distribution of said specific glycan structures in LAM by antibody competition studies (FIG. 10A-10C). These competition assays assumed that in order for one antibody to compete for binding of a second (biotinylated, in cases where they are from the same species) antibody, the two epitopes must be in close proximity to each other in the native molecule, potentially, but not necessarily, on the same or neighboring arabinan branch. This model was supported by asymmetric competition patterns, where for example, biotinylated IgG A194-01, which binds to both uncapped, mono-mannosylated and MSX-substituted Ara4 and Ara6 structures, competed efficiently by itself and by engineered variants and/or derivatives of A194-01, but only partially by murine monoclonal antibody FIND25, which binds only to Ara6 structures. On the other hand, murine monoclonal antibody CS-35, which binds to all Ara4 and Ara6 structures, gives more complete competition, although less efficiently, presumably due to its relatively low affinity.

The results of these assays revealed some surprising and unexpected properties. For example, the IgM isotype of P30B9, which binds to all di-mannose capped ManLAM structures, was competed strongly and completely by itself, CS-35 and FIND170. Without wishing to be bound by theory, the efficient competition of P30B9 by murine monoclonal anti-LAM antibody FIND25 suggests that the di-mannose capped structures in native LAM are largely localized to the Ara6 structures recognized by the FIND antibodies, and not appreciably expressed on Ara4 structures. This heightens the importance of being able to target and specifically bind to di-mannose capped Ara6 residues, as di-mannose capping is believed to be the dominant form of LAM found in virulent strains of the *Mycobacterium tuberculosis*-complex. The highly efficient competition of biotinylated FIND25 by the engineered variant IgM isotype of A194-01 is further evidence for the increased recognition of mannosylated structures by the IgM isotype of A194-01.

C. Competition Studies of A194-01 IgG and P30B9 IgM and Murine Anti-LAM Antibodies to ManLAM and PILAM Binding competition assays between different anti-LAM monoclonal antibodies were used to analyze the distribution of various structural forms in LAM. The IgG isotype of A194-01 recognized both unmodified Ara4 and Ara6 side chains or chains that contained a single mannose cap, but did not bind to side chains with either dimannose or trimannose capping motifs. The two FIND murine antibodies reacted with all forms of Ara6, but not with any Ara4 structures. P30B9 IgM was relatively specific for Ara4 and Ara6 structures that contained dimannose caps.

Consistent with the broadening in reactivity for the A194-01 constructs with increased valencies, these constructs exhibited an increased potency in antibody competition activity. When tested for ability to compete for binding of biotinylated A194-01 IgG against ManLAM, the decameric A194-01 IgM and tetrameric scFv-IgG variants competed more efficiently that the A194-01 IgG isotype itself (FIG. 11), thus signifying an increased potential therapeutic and diagnostic utility, while monomeric Fab and scFv forms competed less effectively (FIG. 1A-iC). The dimeric scFv engineered variant and/or derivative of A194-01 competed equally as well as the A194-01 IgG isotype.

When the epitope specificity of the engineered variants and/or derivatives of A194-01 were compared to that of the A194-01 IgG, it was observed that they possessed broader reactivity (FIG. 14). Whereas the IgG isotype did not bind appreciably to the di-mannose (YB-8-123, YB-8-125) and tri-mannose (YB-BSA-113, YB-BSA-13) substituted structures, the IgM recognized these structures, and the scFv-IgG form possessed increased activity against some of these structures as well. Because di-mannose capping, and especially di-mannose capped Ara6, is the dominant LAM motif in virulent *Mycobacterium tuberculosis*, this suggests a potentially enhanced utility of these engineered forms of A194-01 in therapeutic and diagnostic applications.

Figure 12C:
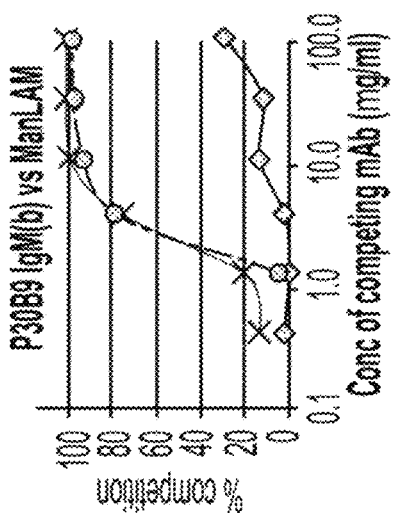
Figure 12B:
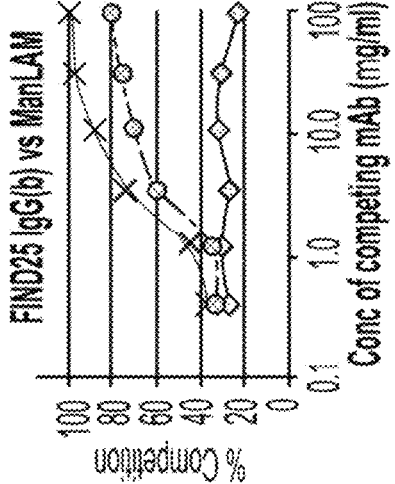
Figure 12A:
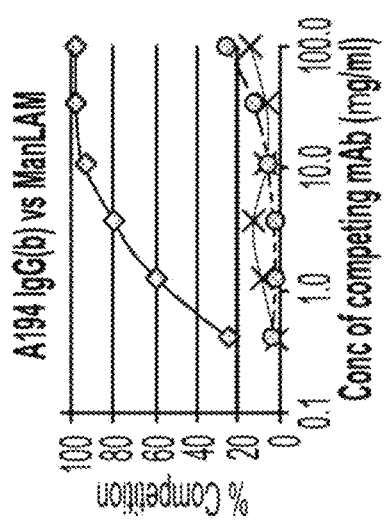
Figure 12E:
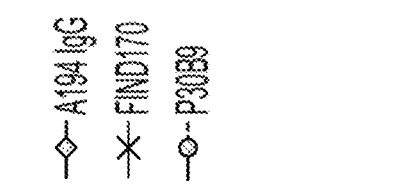
Figure 12E:
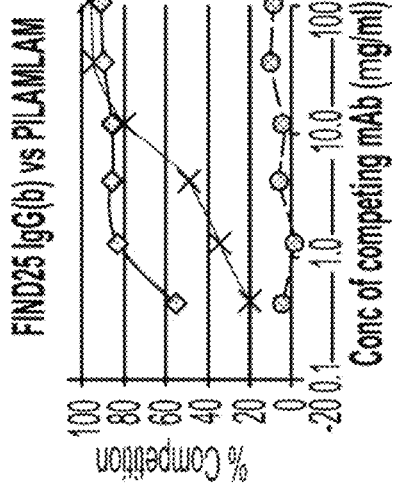
Figure 12D:
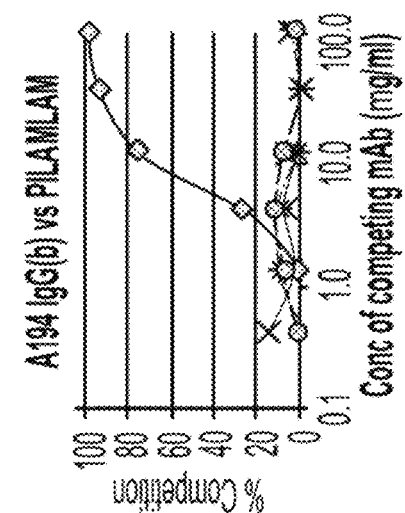

Unlabeled A194-01 IgG competed against binding of biotinylated A194-01 IgG to LAM derived from either *Mycobacterium tuberculosis* (ManLAM) (FIG. 12A) or *Mycobacterium smegmatis* (PILAM) (FIG. 12D), whereas murine monoclonal antibodies FIND170 and P30B9 were not able to compete for A194-01 binding to either antigen (FIG. 12A, 12D). This was consistent with the dominant recognition of Ara4 structures that were recognized by the A194-01 IgG isotype but not by either FIND170, which is specific for Ara6, or P30B9 IgM, which is dependent on dimannose capping residues. Similarly, A194-01 did not compete with binding of either biotinylated FIND25 (FIG. 12B) or P30B9 IgM (FIG. 12C) to ManLAM, consistent with the different epitope specificities for these antibodies. In contrast to the inability of A194-01 IgG fto compete for binding of FIND25 to ManLAM, A194-01 IgG competed strongly with ~90% of the binding of FIND25 to PILAM (FIG. 12E), consistent with the known absence of mannose-capping in PILAM and with the high affinity of A194-01 for the uncapped Ara4 and Ara6 structures.

In contrast to the inefficient competition by A194-01 IgG, P30B9 IgM competed with ~80% binding of FIND25, and FIND170 competed almost completely with binding of P30B9 (FIG. 12B, 12C). This strongly suggested that the great majority of the Ara6 structures recognized by the FIND murine antibodies possessed di-mannose caps, and therefore were also recognized by P30B9 IgM, and that the majority of the dimannose-capped structures recognized by P30B9 were present on Ara6 structures. This suggests that di-mannose capped Ara6 is the dominant immunological motif in LAM motif from virulent *Mycobacterium tuberculosis*.

D. Additional Competition Studies

Additional competition studies were undertaken to highlight the fact that LAM is a complex antigen of undefined heterogeneity. The definition of the different epitope specificities of LAM-reactive monoclonal antibodies allowed the use of binding competition assays to examine the distribution of the various epitopes in native LAMs. The ability of various antibodies to compete for binding of biotinylated probe monoclonal antibodies to LAM and synthetic glycoconjugates was titered by ELISA. Typical competition curves for three monoclonal anti-LAM antibodies, A194-01 IgG, CS-35, and FIND25, are shown in FIG. 13A. The biotinylated probe monoclonal antibodies were competed by their unlabeled versions when present in large excess. The murine monoclonal antibody 908.6 competed poorly, if at all, against the other antibodies. This was due to some extent to the weak affinity of this antibody, but also reflected the restriction of 908.6 binding to uncapped structures, and further suggested that mannose-capped structures were the dominant targets in ManLAM recognized by CS-35 and FIND25. Consistent with its broad reactivity, CS-35 competed for binding of biotinylated A194-01 IgG, although less efficiently than did A194-01 IgG itself, consistent with the higher affinity of A104-01 IgG for LAM. CS-35 also competed fully against biotinylated FIND25, while FIND25 competed only partially against labeled CS-35 (~74% maximum competition) and even less effectively against A194-01 IgG (~50%). This result presumably reflects the presence of Ara4 structures that are recognized by A194-01 IgG and CS-35, but not by FIND25, which binds exclusively to structures containing the Ara6 backbone. Despite its overall high affinity to LAM, A194-01 IgG competed only against itself, but not against either CS-35 or FIND25. This suggested the sites in LAM recognized by the murine monoclonal antibodies were dominated by dimannose and trimannose-capped structures that were not recognized by A194-01 IgG.

Additional competition studies using P30B9 IgM, which binds specifically to di-mannose capped ManLAM, further supported the clinically significant conclusion that the great majority of Ara6 structures in ManLAM were capped with di-mannose, and that the bulk of di-mannose caps resided on Ara6 structures in *Mycobacterium tuberculosis* derived ManLAM. P30B9 IgM competed with ~80% of binding of FIND25 to ManLAM (FIG. 13B), consistent with the majority of the Ara6 structures recognized by FIND25 also being recognized by P30B9 IgM. P30B9 IgM did not compete for FIND25 binding to PTLAM, consistent with the absence of the P30B9 dimannose epitope in PILAAM, due to the lack of mannosylation in PILAM. Furthermore, the A194-01 IgG did not compete for binding of FIND25 to ManLAM, again consistent with the great majority of the Ara6 structures bearing di-mannose caps, which are not recognized by the A194-01 IgG. Confirming the role of mannosylation in this effect, A194-01 IgG competed very efficiently for binding of FIND25 to PTLAM, consistent with the high affinity of A194-01 for PILAM and the absence of mannose capping in this antigen.

Competition data for the binding of biotinylated P30B9 IgM further supported this conclusion. Binding of biotinylated P30B9 IgM was competed most efficiently by itself and with equal efficiency by CS-35 and FIND25, but only weakly and incompletely by A194-01 IgG (FIG. 13C). The level of competition by FIND25 was close to 100%, indicating that essentially all of the di-mannose-dependent P30B9 IgM binding sites were located on Ara6 structures. Consistent with this interpretation, CS-35 also competed for binding of P30B9 to dimannose-capped Ara4 (YB-8-111) and dimannose-capped Ara6 (YB-8-125), whereas FIND170 competed only for the latter antigen and the A194-01 IgG competed for neither. The general similarity between the competition curves for ManLAM and the homogeneous YB-8-125 glycoconjugates indicated that the competition results correlated with the presence or absence of the relevant epitopes on a single carbohydrate side-chain, and that indirect steric effects due to binding of antibodies to more distant heterologous sites played little if any role in competition.

One surprising and unexpected result is the complete lack of competition between A194-01 IgG versus CS-35 and FIND25. The ability of CS-35 to compete for binding of A194-01 IgG to ManLAM was expected due to the recognition of all A194-01 IgG targets by CS-35, and the less efficient competition by CS-35 than by A194-01 IgG itself is consistent with the relative affinities of these antibodies for ManLAM (FIG. 3). Similarly, the incomplete competition of A194-01 IgG binding by FIND25 can be explained by the presence of Ara4 targets recognized by the former but not the latter antibody.

The efficient and complete competition of binding of biotinylated P30B9 IgM by both CS-35 and FIND170 suggests that the di-mannose caps recognized by P30B9 IgM were present almost exclusively of Ara6 structures recognized by the FIND mAb, which is of clinical and diagnostic significance. This was supported by the relatively efficient competition of binding of FIND25 by P30B9 IgM, which blocked ~80% of the binding activity of FIND25 to ManLAM but had no effect for PILAM. This strongly suggests that ~80% of the Ara6 sites in ManLAM recognized by FIND25 contained di-mannose caps, and that essentially all of the di-mannose caps are present on Ara6, and not on Ara4 structures. Taken together with the inability of A194-01 IgG to compete with CS-35 or FIND25, these results demonstrate that di-mannose-substituted Ara6 was the dominant immunogenic structure on ManLAM derived from *Mycobacterium tuberculosis*, and thus represents a highly important antigenic target.

Studies of the LAM-specific antibody responses in patient plasma indicate that the response is dominated by IgG2 isotypes directed against linear Ara4/Ara6 structures, independent of mapping. The efficient competition of P30B9 IgM by IgG monoclonal anti-LAM antibodies specific for arabinofuranose-dependent epitopes such as CS-35 and FIND25, suggests that the dominant IgG2 responses against such epitopes in patient plasma would also compete for di-mannose-dependent any ManLAM-specific antibodies that may be produced in lower titers. Thus, even if the latter class of antibodies might have more effective anti-bacterial activities, it is likely that these effects may be limited by the competition for binding by the dominant, non-functional IgG2 antibodies directed against arabinose-dependent epitopes that are present in patient sera. Without wishing to be bound by theory, the dominant humoral response may actually protect the bacteria against potential effects of rarer antibodies, such as multivalent antibodies like P30B9 IgM, or the engineered variants and/or derivatives of A194-01, such as the pentavalent IgM isotype or the tetravalent scFv-IgG that could provide immune control against infection and pathogenicity.

5. Effects of Valency on A194-01 Binding

The discovery that the reactivity of the dependence of di-mannose-reactive P30B9 on its IgM isotype suggested that multivalency can contribute to the affinity of antibodies towards LAM. Without wishing to be bound by theory, this suggested that a single LAM molecule possessed multiple antibody-binding sites or epitopes, consistent with the known branched structure and complexity of LAM, and that antibodies with higher valencies were able to bind to more sites that divalent antibodies, resulting in greater affinities.

The effect of antibody valency towards binding efficiency to LAM was examined for various engineered variants and/or derivative forms and/or isotypes of the human monoclonal antibody A194-01 in a binding competition assay, using biotinylated A194-01 IgG as the target. The antibody forms included a monovalent single chain scFv in which the VH and VL regions are joined by a flexible peptide linker, a monovalent Fab protein, a dimeric scFv protein in which two scFv domains were joined by a flexible linker, the natural dimeric IgG (FIG. 1A), and two higher valent forms, a tetravalent A194-01 scFv-IgG, and a pentavalent (decavalent for binding sites) IgM isotype (FIG. 1B). Converting the intact divalent IgG to a monovalent Fab resulted in a very large loss of binding activity, with a >100-fold increase in concentration required to compete for 50% of the binding activity of the biotinylated A194-01 IgG, compared to the IgG against itself (FIG. 1C). The single chain also competed inefficiently, with a 33-fold decrease in activity. On the other hand, the scFv dimer competed with similar efficiency as the IgG isotype of A194-01. Without wishing to be bound by theory, this suggested that the efficient binding of the divalent forms of A194-01 to LAM required the attachment of both binding sites to adjacent targets in a single molecule of the antigen. The higher valent forms competed more efficiently, on a molar basis. This may be simply due to the presence of additional binding sites, but may also reflect an increased affinity of the higher valent forms.

The specificity of both the tetrameric scFv-IgG variant and/or derivative of A194-01 and the decameric IgM isotype of A194-01 were compared to that of the IgG isotype of A194-01 against the synthetic glycoconjugate panel described above (FIG. 14). This revealed that both engineered scFv-IgG variant and the engineered IgM isotype possessed broader reactivities with some of the glycans that the IgG isotype recognized only weakly or not at all. Enhanced binding was seen with the di-mannose capped structures (YB-8-111, YB-8-125, YB-8-133) and with some of the tri-mannose capped structures (YB-8-113, YB-8-143, YB-BSA-13) with the engineered IgM isotype of A194-01 possessing the broadest reactivity panel. This has significant diagnostic and therapeutic potential, given the significance of di-mannose capping. Interestingly, enhanced reactivity was also seen for the A194-01 IgM isotype with an arabinose structure that was missing the terminal β-D-Araf-(1→2) linkage (YB-BSA-09), which was not recognized by any of the monoclonal anti-LAM antibodies tested. Without wishing to be bound by theory, this suggested that the increased valency resulted in a strengthening of the avidity of the IgM isotype of A194-01 for its basic arabinose-containing epitope, to the point that inhibitory effects of terminal substitution were overcome.

The reactivity profiles of A194-01 IgG and the engineered IgM and scFv-IgG forms of A194-01 were further analyzed by reciprocal binding competition experiments against either ManLAM or PILAM. Whereas all three forms cross-competed for binding of the biotinylated antibodies to PILAM and for binding of A194-01 IgG to ManLAM, only the higher-valent scFv-IgG and IgM forms of A194-01 competed efficiently with binding of the modified antibodies to ManLAM. These differences in competition activities were consistent with a broader binding profile of the engineered forms, and suggested that they bound to sites on LAM that were not recognized by the IgG form.

This conclusion was further supported by reciprocal competition studies in which the different isotypes of A194-01 competed with binding of biotinylated FIND25 IgG and P30B9 IgM to ManLAM. Whereas the A194-01 IgG did not compete with binding of P30B9 IgM and FIND25 to ManLAM, both the scFv-IgG and IgM forms of A194-01 competed almost completely with binding of these two monoclonal antibodies (FIG. 15A, B). As expected, all three forms of A194-01 competed with binding of FIND25 to PILAM (FIG. 15C) consistent with the absence of mannosylation in PILAM. This enhanced activity suggested that these modifications would enhance the potential utility of this antibody for immunodiagnostic applications, and may also increase the effectiveness of these reagents as immunotherapeutic purposes as well.

EXAMPLE 2—Isolation and characterization of novel human monoclonal antibodies specific for glycolipids of M. tb—Isolation of first mAb specific for an epitope shared by LAM and PIM6.

P95C1 antibody heavy and light chain were isolated from a single B cell clone, by screening for reactivity with ManLAM, from a patient with latent tuberculosis infection (LTBI). P95C1 is an IgM isotype antibody, which binds to both ManLAM and PILAM. This was shown by glycoconjugate binding studies that indicated that P95C1 did not bind to any molecules that expressed various arabinose sidechains, either uncapped or capped with various mannose structures. The only structures recognized were two polymannose structures that possessed structural motifs present in the mannan base that were conserved between PIM6 and various LAMs (FIG. 18A), 18B, 18C-1-18C-7). This LAM-PIM6 crossreactivity was confirmed by a western blot assay showing that whereas A194-01 and P30B9 bound only to LAM, P95C1 also reacted with LAM precursor glycolipids molecules, LM and PIM6 (FIG. 20A, 20B).

Although P95C1, like P30B9, was naturally expressed as an IgM, in contrast to P30B9 it retained reactivity when converted to either the IgA or IgG isotype (FIG. 19). This may be a reflection of the nature of the nature of the epitope or ots location in the mannan region of the LAM molecule, or may be related to the higher number of mutations in the P95C1 variable regions, consistent with a more mature antibody sequence. The variable regions of the P95C1 heavy and light chain have 19 and 13 amino acid point mutations respectively from its closet germline antibody sequence.

It has recently been shown that antibodies made by individuals with latent disease are functionally superior from those with active tuberculosis in promoting phagolysosomal fusion, inflammasome activation, and macrophage killing of internalized mycobacteria (Lu et al. 2016). It is therefore of interest that P95C1 was isolated from a LTBI patient and it has more mutations in its variable region than P30B9 and two other LAM-specific mAbs that were isolated from the same LTBI patient that possess distinct ManLAM epitope specificity.

Little is known about the nature of the human humoral immune response against M. tb infection. Although it is widely known that surface glycolipids of M. tb contribute to inhibition of the activity of macrophages and dendritic cells there is contradictory information about whether mannose-capped lipoarabinomannan (ManLAM) or phosphatidylinositol mannoside 6 (PIM6) is the major immunoinhibitory surface component of M. tb. This question is further complicated by the common contamination of purified preparations of PIM6 by ManLAM, and vice versa. One way of addressing this question is to test the ability of antibodies specific for these two modulators to inhibit these inhibitory activities. However, this has not been possible due to the absence of well-characterized antibodies that are specific for these two antigens. To date, there have been no antibodies reported that recognize PIM6, and this invention describes the first high affinity mAb that recognizes PIM6. The PIMs (PIM2 and PIM4) are precursors for ManLAM, and there is some structural relationship between the mannan domain of ManLAM and the polymannose structure of PIM6.

Antibodies can exert their functions in two ways 1) by direct blocking of host cell invasion and neutralization of bacterial products 2) indirectly through Fc-mediated complement and cell activation mechanisms through Fc receptors. Antibody-mediated effector function are greatly affected by the antibody isotype. A recent study showed human isotype-dependent inhibitory antibody responses against M. tb and demonstrated that IgA, but not IgG, antibodies specific for different M. tb surface antigens can block M. tb uptake by lung epithelial cells independent of the expression of IgA Fc receptors. To test the effect of P95C1 isotypes on LAM binding, the constant region of P95C1-IgM heavy chain was replaced by CH-IgA and CH-IgG to generate P95C1-IgA and P95C1-IgG. The binding affinity of P95C1 isotypes (IgM, IgA, IgG) with ManLAM and PILAM were comparable (FIG. 19).

Other Embodiments

Any improvement may be made in part or all of the antibodies, compositions, kits and methods. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed:

1. A monoclonal anti-PIM6/LAM antibody, or an antigen-binding portion thereof, that specifically binds to an epitope present in lipoarabinomannan (LAM) and phosphatidyl-myo-inositol mannoside 6 (PIM6), the epitope comprising at least one polymannose structure, wherein the anti-PIM6/LAM antibody comprises a CDR1 light chain variable region having at least 80% identity with SEQ ID NO: 13 or antigenic fragments thereof, a CDR2 light chain variable region having at least 80% identity with SEQ ID NO: 14 or antigenic fragments thereof, a CDR3 light chain variable region having at least 80% identity with SEQ ID NO: 15 or antigenic fragments thereof, a CDR1 heavy chain variable region having at least 80% identity with SEQ ID NO: 16 or antigenic fragments thereof, a CDR2 heavy chain variable region having at least 80% identity with SEQ ID NO: 17 or antigenic fragments thereof, and a CDR3 heavy chain variable region having at least 80% identity with SEQ ID NO: 18 or antigenic fragments thereof, having a modified heavy chain variable region and a modified light chain variable region.

2. The monoclonal anti-PIM6/LAM antibody, or antigen-binding portion thereof, of claim 1, wherein the epitope is in PIM6 mannan domain, and is also present in mycobacterial lipomannan (LM).

3. The monoclonal anti-PIM6/LAM antibody, or antigen-binding portion thereof, of claim 1, said antibody comprising a heavy chain variable region comprising the amino acid sequence of SEQ ID NO:47 and a light chain variable region comprising the amino acid sequence of SEQ ID NO: 48.

4. The monoclonal anti-PIM6/LAM antibody or antigen-binding portion thereof of claim 1, wherein the anti-PIM6/LAM antibody is an IgM antibody.

5. The monoclonal anti-PIM6/LAM antibody or antigen-binding portion thereof of claim 1, wherein the anti-PIM6/LAM antibody is an IgA or an IgG antibody.

6. A method of diagnosing an active tuberculosis infection in an individual comprising:
   (a) providing a sample from an individual that comprises or is suspected of comprising lipoarabinomannan (LAM);
   (b) contacting said sample with a first antibody that binds specifically to an epitope on a LAM molecule;
   (c) contacting the sample with a detection antibody that binds specifically to a different binding site in the LAM molecule than the binding site bound by the first antibody;
   (d) detecting binding of the detection antibody to the different binding site in the LAM molecule; and
   (e) diagnosing the patient as having an active tuberculosis infection,
   wherein capture of LAM by the first antibody indicates active tuberculosis infection, and
   wherein at least one of the antibodies is the monoclonal anti-PIM6/LAM antibody of claim 1.

7. The method of claim 6, wherein the detection antibody is the monoclonal anti-PIM6/LAM antibody of claim 1.

8. The method of claim 6, wherein the individual is a human.

9. A method of treating a tuberculosis infection in an individual comprising administering to said individual a therapeutically effective amount of the monoclonal anti-PIM6/LAM antibody of claim 1.

10. The method of claim 9, further comprising administering to said individual a therapeutically effective amount of at least one antibiotic.

11. The method of claim 9, wherein the tuberculosis infection is a multi-drug resistant (MDR-TB) tuberculosis infection.

* * * * *

```
                       SEQUENCE LISTING

Sequence total quantity: 50
SEQ ID NO: 1           moltype = AA  length = 6
FEATURE                Location/Qualifiers
source                 1..6
                       mol_type = protein
                       organism = Homo sapiens
SEQUENCE: 1
RSIRSA                                                                   6

SEQ ID NO: 2           moltype =     length =
SEQUENCE: 2
000

SEQ ID NO: 3           moltype = AA  length = 9
FEATURE                Location/Qualifiers
source                 1..9
                       mol_type = protein
                       organism = Homo sapiens
SEQUENCE: 3
QQYDFWYTF                                                                9

SEQ ID NO: 4           moltype = AA  length = 8
FEATURE                Location/Qualifiers
source                 1..8
                       mol_type = protein
                       organism = Homo sapiens
SEQUENCE: 4
GFNFEDFG                                                                 8

SEQ ID NO: 5           moltype = AA  length = 8
FEATURE                Location/Qualifiers
source                 1..8
                       mol_type = protein
                       organism = Homo sapiens
SEQUENCE: 5
ISWNGANI                                                                 8

SEQ ID NO: 6           moltype = AA  length = 13
FEATURE                Location/Qualifiers
source                 1..13
                       mol_type = protein
                       organism = Homo sapiens
SEQUENCE: 6
IDWYRDDYYK MDV                                                          13

SEQ ID NO: 7           moltype = AA  length = 6
FEATURE                Location/Qualifiers
source                 1..6
                       mol_type = protein
```

```
                              -continued organism = Homo sapiens
SEQUENCE: 7
QSINSN                                                              6

SEQ ID NO: 8        moltype =    length =
SEQUENCE: 8
000

SEQ ID NO: 9        moltype = AA  length = 9
FEATURE             Location/Qualifiers
source              1..9
                    mol_type = protein
                    organism = Homo sapiens
SEQUENCE: 9
QQYKAFKTF                                                           9

SEQ ID NO: 10       moltype = AA  length = 8
FEATURE             Location/Qualifiers
source              1..8
                    mol_type = protein
                    organism = Homo sapiens
SEQUENCE: 10
GGSFSGYY                                                            8

SEQ ID NO: 11       moltype = AA  length = 13
FEATURE             Location/Qualifiers
source              1..13
                    mol_type = protein
                    organism = Homo sapiens
SEQUENCE: 11
FDLGGSITHS RGT                                                     13

SEQ ID NO: 12       moltype = AA  length = 13
FEATURE             Location/Qualifiers
source              1..13
                    mol_type = protein
                    organism = Homo sapiens
SEQUENCE: 12
RGLAMGGTKE FDS                                                     13

SEQ ID NO: 13       moltype = AA  length = 12
FEATURE             Location/Qualifiers
source              1..12
                    mol_type = protein
                    organism = Homo sapiens
SEQUENCE: 13
QNVLDSANNR NY                                                      12

SEQ ID NO: 14       moltype =    length =
SEQUENCE: 14
000

SEQ ID NO: 15       moltype = AA  length = 9
FEATURE             Location/Qualifiers
source              1..9
                    mol_type = protein
                    organism = Homo sapiens
SEQUENCE: 15
TQYHRLPHT                                                           9

SEQ ID NO: 16       moltype = AA  length = 9
FEATURE             Location/Qualifiers
source              1..9
                    mol_type = protein
                    organism = Homo sapiens
SEQUENCE: 16
GGSINTNNW                                                           9

SEQ ID NO: 17       moltype = AA  length = 7
FEATURE             Location/Qualifiers
source              1..7
                    mol_type = protein
                    organism = Homo sapiens
SEQUENCE: 17
IHRHGDT                                                             7

SEQ ID NO: 18       moltype = AA  length = 15
FEATURE             Location/Qualifiers
source              1..15
```

```
                              mol_type = protein
                              organism = Homo sapiens
SEQUENCE: 18
CPLGYCSGDD CHRVA                                                        15

SEQ ID NO: 19           moltype = AA   length = 5
FEATURE                 Location/Qualifiers
source                  1..5
                        mol_type = protein
                        organism = Homo sapiens
SEQUENCE: 19
GGSGG                                                                    5

SEQ ID NO: 20           moltype =     length =
SEQUENCE: 20
000

SEQ ID NO: 21           moltype = AA   length = 96
FEATURE                 Location/Qualifiers
source                  1..96
                        mol_type = protein
                        organism = Homo sapiens
SEQUENCE: 21
QVQLLESGGG VVRPGGSLRL SCAASGFNFE DFGMSWVRQA PGKGLEWVSS ISWNGANIGY        60
VDSVKGRFTI SRDNAKNSLY LQMNSLRAED TALYYC                                 96

SEQ ID NO: 22           moltype = AA   length = 96
FEATURE                 Location/Qualifiers
source                  1..96
                        mol_type = protein
                        organism = Homo sapiens
SEQUENCE: 22
EVQLVESGGG VVRPGGSLRL SCAASGFTFD DYGMSWVRQA PGKGLEWVSG INWNGGSTGY        60
ADSVKGRFTI SRDNAKNSLY LQMNSLRAED TALYHC                                 96

SEQ ID NO: 23           moltype = AA   length = 14
FEATURE                 Location/Qualifiers
source                  1..14
                        mol_type = protein
                        organism = Homo sapiens
SEQUENCE: 23
AIDWYRDDYY KMDV                                                         14

SEQ ID NO: 24           moltype = AA   length = 88
FEATURE                 Location/Qualifiers
source                  1..88
                        mol_type = protein
                        organism = Homo sapiens
SEQUENCE: 24
EIVMTQSPAT LSVSPGERAT LSCRASRSIR SALAWYQHKP GQAPRLLIFG ASTRATGIPA        60
RFSGSGSGTD FTLTVSSIRS EDSAVYYC                                          88

SEQ ID NO: 25           moltype = AA   length = 88
FEATURE                 Location/Qualifiers
source                  1..88
                        mol_type = protein
                        organism = Homo sapiens
SEQUENCE: 25
EIVMTQSPAT LSVSPGERAT LSCRASQSVS SNLAWYQQKP GQAPRLLIYG ASTRATGIPA        60
RFSGSGSGTE FTLTISSLQS EDFAVYYC                                          88

SEQ ID NO: 26           moltype = AA   length = 8
FEATURE                 Location/Qualifiers
source                  1..8
                        mol_type = protein
                        organism = Homo sapiens
SEQUENCE: 26
QQYDFWYT                                                                 8

SEQ ID NO: 27           moltype = AA   length = 101
FEATURE                 Location/Qualifiers
source                  1..101
                        mol_type = protein
                        organism = Homo sapiens
SEQUENCE: 27
QVQLQQWGAG LLKPSETLSL TCAVYGGSFS GYYWSWIRQS PETGLEWLGE FDLGGSITHS        60
RGTNYNPSLK SRVTISGDTS KNQFSLKLTS VTAADTAVYY C                          101

SEQ ID NO: 28           moltype = AA   length = 95
```

```
FEATURE                 Location/Qualifiers
source                  1..95
                        mol_type = protein
                        organism = Homo sapiens
SEQUENCE: 28
QVQLQQWGAG LLKPSETLSL TCAVYGGSFS GYYWSWIRQP PGKGLEWIGE INHSGSTNYN    60
PSLKSRVTIS VDTSKNQFSL KLSSVTAADT AVYYC                              95

SEQ ID NO: 29           moltype = AA   length = 14
FEATURE                 Location/Qualifiers
source                  1..14
                        mol_type = protein
                        organism = Homo sapiens
SEQUENCE: 29
ARGLAMGGTK EFDS                                                     14

SEQ ID NO: 30           moltype = AA   length = 88
FEATURE                 Location/Qualifiers
source                  1..88
                        mol_type = protein
                        organism = Homo sapiens
SEQUENCE: 30
DIQMTQSPDS LSASVGDRIT ITCRASQSIN SNLAWYQQKP GKAPKLLIYK ASDLESGVPS    60
RFSGSGSGTE FTLTISSLQP DDFATYYC                                      88

SEQ ID NO: 31           moltype = AA   length = 88
FEATURE                 Location/Qualifiers
source                  1..88
                        mol_type = protein
                        organism = Homo sapiens
SEQUENCE: 31
DIQMTQSPST LSASVGDRVT ITCRASQSIS SWLAWYQQKP GKAPKLLIYK ASSLESGVPS    60
RFSGSGSGTE FTLTISSLQP DDFATYYC                                      88

SEQ ID NO: 32           moltype = AA   length = 8
FEATURE                 Location/Qualifiers
source                  1..8
                        mol_type = protein
                        organism = Homo sapiens
SEQUENCE: 32
QQYKAFKT                                                             8

SEQ ID NO: 33           moltype = AA   length = 96
FEATURE                 Location/Qualifiers
source                  1..96
                        mol_type = protein
                        organism = Homo sapiens
SEQUENCE: 33
EVQLLESGPG LVRPWGTLSL TCAVSGGSIN TNNWWSWVRQ SPGKGLEWIG EIHRHGDTNY    60
NPSLKRRVSI SMDESMNQFS LRLISVTAAD TAVYYC                             96

SEQ ID NO: 34           moltype = AA   length = 96
FEATURE                 Location/Qualifiers
source                  1..96
                        mol_type = protein
                        organism = Homo sapiens
SEQUENCE: 34
QVQLQESGPG LVKPSGTLSL TCAVSGGSIS SSNWWSWVRQ PPGKGLEWIG EIYHSGSTNY    60
NPSLKSRVTI SVDKSKNQFS LKLSSVTAAD TAVYYC                             96

SEQ ID NO: 35           moltype =      length =
SEQUENCE: 35
000

SEQ ID NO: 36           moltype = AA   length = 94
FEATURE                 Location/Qualifiers
source                  1..94
                        mol_type = protein
                        organism = Homo sapiens
SEQUENCE: 36
DIQMTQSPSS LSVSLGERAT INCKSSQNVL DSANNRNYFG WYQQKPGQPP KLLISWASTR    60
ESGVPDRFSG SGSGTDFTLI ISGLQVEDVA VYYC                               94

SEQ ID NO: 37           moltype = AA   length = 94
FEATURE                 Location/Qualifiers
source                  1..94
                        mol_type = protein
                        organism = Homo sapiens
SEQUENCE: 37
```

```
DIVMTQSPDS LAVSLGERAT INCKSSQSVL YSSNNKNYLA WYQQKPGQPP KLLIYWASTR    60
ESGVPDRFSG SGSGTDFTLT ISSLQAEDVA VYYC                               94

SEQ ID NO: 38           moltype =    length =
SEQUENCE: 38
000

SEQ ID NO: 39           moltype = DNA   length = 1356
FEATURE                 Location/Qualifiers
source                  1..1356
                        mol_type = unassigned DNA
                        organism = Homo sapiens
SEQUENCE: 39
caagtgcagc tgttggagtc tgggggaggt gtggtacggc cggggggtc cctgagactc      60
tcctgtgcag cctctggatt caactttgaa gattttggca tgagctgggt ccgccaagct    120
ccagggaagg ggctggagtg ggtctctagt attagttgga atggtgctaa tataggctat    180
gtagactctg tgaagggccg attcaccatc tccagagaca cgccaagaa ctccctatat     240
ctgcaaatga acagtctgag agccgaggac acggccttat attactgtgc gatagactgg    300
tacagagacg actactacaa gatggacgtc tggggcaaag ggaccacggt caccgtctcc    360
tcagcctcga ccaagggccc atcggtcttc ccgctagcgc cctcctccaa gagcacctct    420
gggggcacag cggccctggg ctgcctggtc aaggactact tccccgaacc tgtgacggtc    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca cccctcatga tctcccggac    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggat   1080
gagctgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaatga                             1356

SEQ ID NO: 40           moltype = AA   length = 451
FEATURE                 Location/Qualifiers
source                  1..451
                        mol_type = protein
                        organism = Homo sapiens
SEQUENCE: 40
QVQLLESGGG VVRPGGSLRL SCAASGFNFE DFGMSWVRQA PGKGLEWVSS ISWNGANIGY     60
VDSVKGRFTI SRDNAKNSLY LQMNSLRAED TALYYCAIDW YRDDYYKMDV WGKGTTVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPELLG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRD    360
ELTKNQVSLT CLVKGFYPSD IAVEWESNGQ PENNYKTTPP VLDSDGSFFL YSKLTVDKSR    420
WQQGNVFSCS VMHEALHNHY TQKSLSLSPG K                                   451

SEQ ID NO: 41           moltype = DNA   length = 642
FEATURE                 Location/Qualifiers
source                  1..642
                        mol_type = unassigned DNA
                        organism = Homo sapiens
SEQUENCE: 41
gaaatagtga tgacgcagtc tccagccacc ctgtctgtct ctccagggga aagagccacc     60
ctctcctgca gggccagtcg gagtattcgc agcgccttag cctggtacca gcacaaacct    120
ggccaggctc ccaggctcct catctttggt gcatccacca gggccactgg tatcccagcc    180
aggttcagtg gcagtgggtc tgggacagac ttcactctca ccgtcagcag catacgtgtc    240
gaggattctg cagtttatta ctgtcagcag tatgattttt ggtacacttt tggccagggg    300
accaagctgg agatcaaacg aactgtggct gcaccatctg tcttcatctt cccgccatct    360
gatgagcagt tgaaatctgg aactgcctct gttgtgtgcc tgctgaataa cttctatccc    420
agagaggcca agtacagtgg aaggtcgac aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgtt ag                       642

SEQ ID NO: 42           moltype = AA   length = 213
FEATURE                 Location/Qualifiers
source                  1..213
                        mol_type = protein
                        organism = Homo sapiens
SEQUENCE: 42
EIVMTQSPAT LSVSPGERAT LSCRASRSIR SALAWYQHKP GQAPRLLIFG ASTRATGIPA     60
RFSGSGSGTD FTLTVSSIRS EDSAVYYCQQ YDFWYTFGQG TKLEIKRTVA APSVFIFPPS    120
DEQLKSGTAS VVCLLNNFYP REAKVQWKVD NALQSGNSQE SVTEQDSKDS TYSLSSTLTL    180
```

```
SKADYEKHKV YACEVTHQGL SSPVTKSFNR GEC                               213

SEQ ID NO: 43           moltype = AA  length = 115
FEATURE                 Location/Qualifiers
source                  1..115
                        mol_type = protein
                        organism = Homo sapiens
SEQUENCE: 43
QVQLQQWGAG LLKPSETLSL TCAVYGGSFS GYYWSWIRQS PETGLEWLGE FDLGGSITHS  60
RGTNYNPSLK SRVTISGDTS KNQFSLKLTS VTAADTAVYY CARGLAMGGT KEFDS      115

SEQ ID NO: 44           moltype = AA  length = 96
FEATURE                 Location/Qualifiers
source                  1..96
                        mol_type = protein
                        organism = Homo sapiens
SEQUENCE: 44
DIQMTQSPDS LSASVGDRIT ITCRASQSIN SNLAWYQQKP GKAPKLLIYK ASDLESGVPS  60
RFSGSGSGTE FTLTISSLQP DDFATYYCQQ YKAFKT                           96

SEQ ID NO: 45           moltype = DNA  length = 379
FEATURE                 Location/Qualifiers
source                  1..379
                        mol_type = unassigned DNA
                        organism = Homo sapiens
SEQUENCE: 45
caggtgcagc tacagcagtg gggcgcagga ctgttgaagc cttcggagac cctgtccctc  60
acctgcgctg tctatggtgg gtccttcagt ggttactact ggagctggat ccgccagtcc 120
ccagagacgg ggctggagtg gcttggcgaa ttcgatcttg gtggaagcat cactcatagt 180
agaggcacca actacaaccc gtcgctcaag agtcgagtca ccatctcagg agacacgtcc 240
aagaaccagt tctccctgaa actgacctct gtgaccgccg cggacacggc tgtctattac 300
tgtgcgagag gtttagcaat gggtggaact aaggagtttg actcctgggg ccagggaacc 360
ctggtcaccg tctcctcag                                             379

SEQ ID NO: 46           moltype = DNA  length = 319
FEATURE                 Location/Qualifiers
source                  1..319
                        mol_type = unassigned DNA
                        organism = Homo sapiens
SEQUENCE: 46
gacatccaga tgacccagtc tccagactcc ctgtctgcat ctgtaggaga cagaatcacc  60
atcacttgcc gggccagtca gagtattaat agtaatttgg cctggtatca gcagaaaccg 120
gggaaagccc ctaagctcct gatctataag gcgtctgatt tagaaagtgg ggtcccatca 180
aggttcagcg gcagtggatc tgggacagaa ttcactctca ccatcagcag cctgcagcct 240
gatgattttg caacttatta ttgccaacag tataaagcat tcaagacgtt cggccacggg 300
accaaggtgg aaatcaaac                                              319

SEQ ID NO: 47           moltype = AA  length = 111
FEATURE                 Location/Qualifiers
source                  1..111
                        mol_type = protein
                        organism = Homo sapiens
SEQUENCE: 47
EVQLLESGPG LVRPWGTLSL TCAVSGGSIN TNNWWSWVRQ SPGKGLEWIG EIHRHGDTNY  60
NPSLKRRVSI SMDESMNQFS LRLISVTAAD TAVYYCCPLG YCSGDDCHRV A          111

SEQ ID NO: 48           moltype = AA  length = 103
FEATURE                 Location/Qualifiers
source                  1..103
                        mol_type = protein
                        organism = Homo sapiens
SEQUENCE: 48
DIQMTQSPSS LSVSLGERAT INCKSSQNVL DSANNRNYFG WYQQKPGQPP KLLISWASTR  60
ESGVPDRFSG SGSGTDFTLI ISGLQVEDVA VYYCTQYHRL PHT                   103

SEQ ID NO: 49           moltype = DNA  length = 367
FEATURE                 Location/Qualifiers
source                  1..367
                        mol_type = unassigned DNA
                        organism = Homo sapiens
SEQUENCE: 49
gaggtgcagc tcttggagtc gggcccagga ctggtgaggc cttggggac tctgtccctc   60
acctgcgctg tctctggtgg ctccatcaat actaataact ggtggagttg ggtccgccag 120
tccccgggga aggggctgga gtggattgga gaaatccatc gtcatgggga caccaactac 180
aacccgtcac tcaagaggcg agtctccata tcgatggacg agtccatgaa ccagttctct 240
ctgaggctta tctctgtgac cgccgcggac acggccgtgt attactgttg tccctagga  300
tattgtagtg gtgatgactg tcaccgagtt gcctggggcc ggggaatcct ggtcaccgtc 360
tcttcag                                                           367
```

```
SEQ ID NO: 50          moltype = DNA  length = 340
FEATURE                Location/Qualifiers
source                 1..340
                       mol_type = unassigned DNA
                       organism = Homo sapiens
SEQUENCE: 50
gacatccaga tgacccagtc tccatcctcc ctgtctgtgt ctctgggcga gagggccacc   60
atcaactgca agtccagcca gaatgtttta gacagcgcca acaataggaa ctacttcggt  120
tggtaccagc agaaaccagg gcagcctcct aagctgctca tttcctgggc atctacacgg  180
gaatccgggg tccctgaccg attcagtggc agcggctctg ggacagactt cactctcatc  240
atcagcggcc tgcaggttga agatgtggca gtttattact gtacacagta tcatagactt  300
cctcacacct tcggccaagg gacacgactg gaaattaaac                        340
```